US012583965B2

(12) United States Patent
  Tsai et al.

(10) Patent No.: US 12,583,965 B2
(45) Date of Patent: Mar. 24, 2026

(54) POLYMERIZATIONS IN SUPERCRITICAL CARBON DIOXIDE, PRODUCTS OF SAME, AND USES THEREOF

(71) Applicant: CORNELL UNIVERSITY, Ithaca, NY (US)

(72) Inventors: Wen-Chyan Tsai, Ithaca, NY (US); Yadong Wang, Ithaca, NY (US)

(73) Assignee: Cornell University, Ithaca, NY (US)

( * ) Notice: Subject to any disclaimer, the term of this patent is extended or adjusted under 35 U.S.C. 154(b) by 472 days.

(21) Appl. No.: 18/009,718

(22) PCT Filed: Jun. 14, 2021

(86) PCT No.: PCT/US2021/037274
  § 371 (c)(1),
  (2) Date: Dec. 10, 2022

(87) PCT Pub. No.: WO2021/253009
  PCT Pub. Date: Dec. 16, 2021

(65) Prior Publication Data
  US 2023/0250225 A1    Aug. 10, 2023

Related U.S. Application Data

(60) Provisional application No. 63/040,252, filed on Jun. 17, 2020, provisional application No. 63/038,612, filed on Jun. 12, 2020.

(51) Int. Cl.
  *C08G 63/20* (2006.01)
  *A61L 31/06* (2006.01)
  (Continued)

(52) U.S. Cl.
  CPC .............. *C08G 63/20* (2013.01); *A61L 31/06* (2013.01); *A61L 31/16* (2013.01); *B65D 65/466* (2013.01);
  (Continued)

(58) Field of Classification Search
  None
  See application file for complete search history.

(56) References Cited

U.S. PATENT DOCUMENTS 4,925,790 A    5/1990   Blanch et al.
5,478,910 A    12/1995  Russell et al.
    (Continued)

FOREIGN PATENT DOCUMENTS

CN    109750083 A    5/2019
CN    109852641 A    6/2019
WO    2008045516 A1  4/2008

OTHER PUBLICATIONS

Cooper, A., "Polymer Synthesis and Processing using Supercritical Carbon Dioxide," J. Mater. Chem., 2000, 10, all enclosed pages cited.

(Continued)

*Primary Examiner* — Megan McCulley
(74) *Attorney, Agent, or Firm* — Young Basile Hanlon & MacFarlane, P.C.

(57)    ABSTRACT

In various examples, methods of forming a polymer (e.g., a condensation polymer including but not limited to a polyester), include the steps of forming a mixture comprising one or more monomer(s), one or more biocatalyst(s), and carbon dioxide. In various examples, the methods are at least partially carried out in sub critical carbon dioxide or supercritical carbon dioxide. In various examples, a polymer is a condensation polymer. In various examples, a fabricated article, which may be a medical article, includes one or more polymer(s).

21 Claims, 44 Drawing Sheets

(51) Int. Cl.
    *A61L 31/16*           (2006.01)
    *B65D 65/46*         (2006.01)
    *C08G 63/81*         (2006.01)
    *C08G 63/82*         (2006.01)

(52) U.S. Cl.
    CPC ............. *C08G 63/81* (2013.01); *C08G 63/82*
        (2013.01); *C08G 2230/00* (2013.01)

(56) References Cited

U.S. PATENT DOCUMENTS

| | | | |
|---|---|---|---|
| 5,783,627 A | 7/1998 | Kao et al. | |
| 7,081,486 B2 | 7/2006 | Imai et al. | |
| 2004/0242831 A1 | 12/2004 | Tian et al. | |
| 2006/0069223 A1 | 3/2006 | Lee et al. | |
| 2012/0136082 A1* | 5/2012 | Daiss | C08F 255/00 |
| | | | 526/279 |
| 2012/0231165 A1 | 9/2012 | Belcheva | |

OTHER PUBLICATIONS

Said-Galiyev, et al., "Supercritical Carbon Dioxide and Polymers," Polymer Science, Ser. C, vol. 46, No. 1, 2004, all enclosed pages cited.
Loeker, et al., "Enzyme-Catalyzed Ring-Opening Polymerization of E-Caprolactone in Supercritical Carbon Dioxide," Macromolecules 2004, 37, all enclosed pages cited.
Kobayashi, S., "Lipase-catalyzed polyester synthesis—A green polymer chemistry," Proc. Jpn. Acad., Ser. B 86 (2010), all enclosed pages cited.
Jiang, et al., "Enzymatic Synthesis of Biobased Polyesters and Polyamides," Polymers, 2016, 8, 243; all enclosed pages cited.

* cited by examiner glycerol          sebacic acid

Lipases

SC-CO$_2$          SC-CO$_2$
+
H$_2$O

OX   (X = H or polymer chain, R)

**synthesized *l*-PGS**

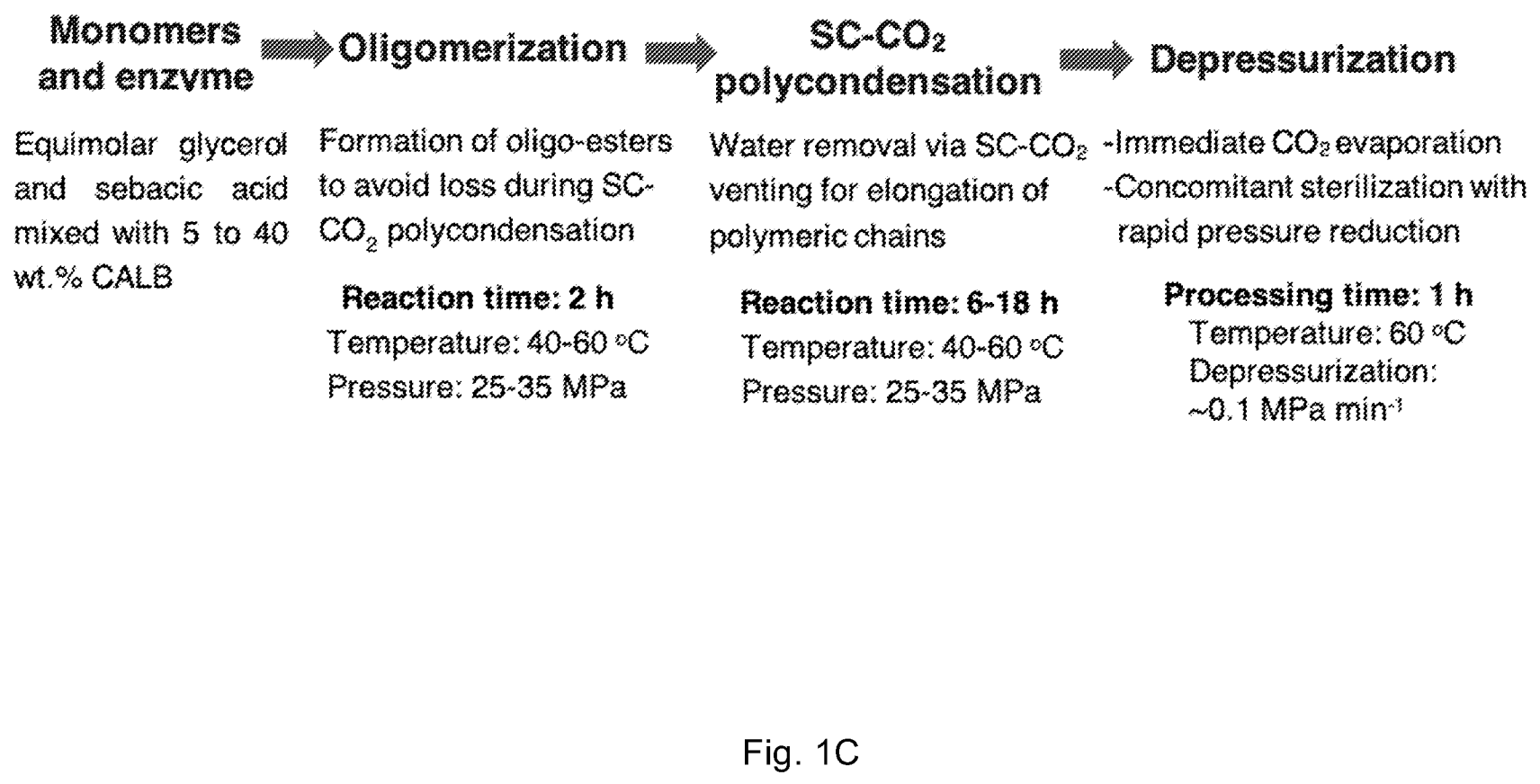

Monomers and enzyme $\Longrightarrow$ Oligomerization $\Longrightarrow$ SC-CO$_2$ polycondensation $\Longrightarrow$ Depressurization

Equimolar glycerol and sebacic acid mixed with 5 to 40 wt.% CALB

Formation of oligo-esters to avoid loss during SC-CO$_2$ polycondensation

Water removal via SC-CO$_2$ venting for elongation of polymeric chains

-Immediate CO$_2$ evaporation
-Concomitant sterilization with rapid pressure reduction

Reaction time: 2 h
Temperature: 40-60 °C
Pressure: 25-35 MPa

Reaction time: 6-18 h
Temperature: 40-60 °C
Pressure: 25-35 MPa

Processing time: 1 h
Temperature: 60 °C
Depressurization:
~0.1 MPa min$^{-1}$

Fig. 1C

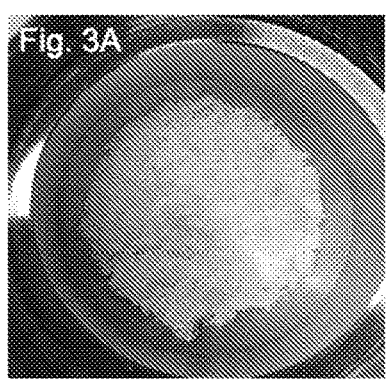
Fig. 3A
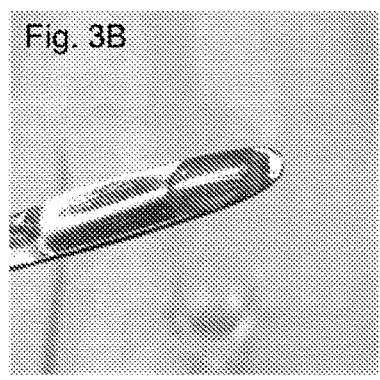
Fig. 3B
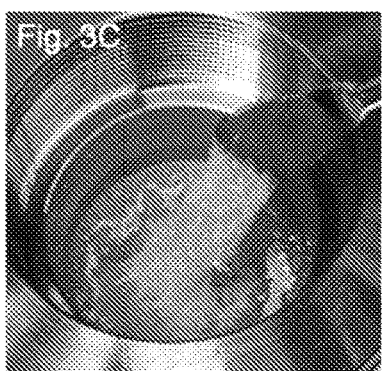
Fig. 3C
Fig. 3D
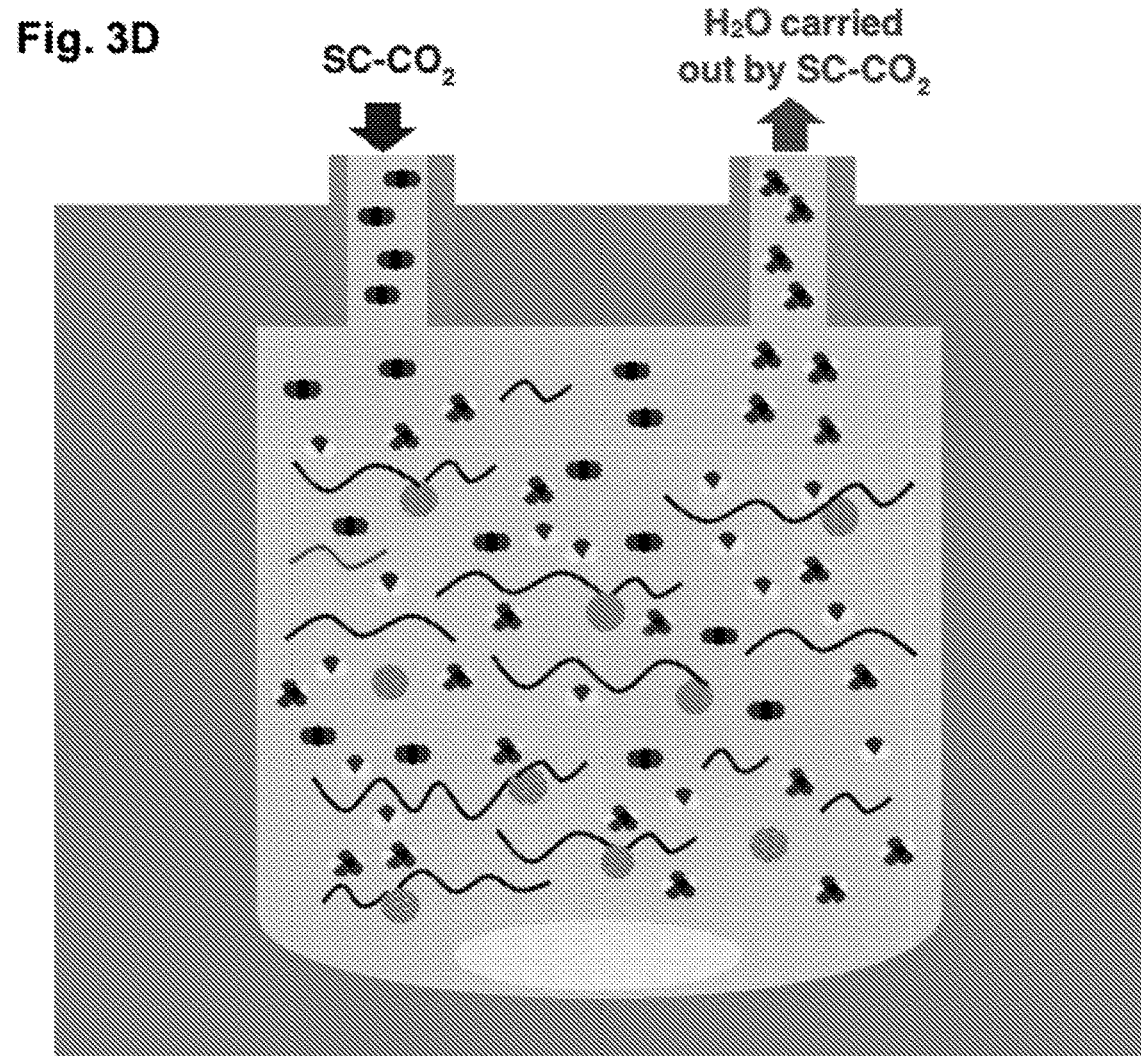
SC-$CO_2$
$H_2O$ carried out by SC-$CO_2$
⬤ : lipase
⬤ : carbon dioxide
● : water molecules
〜 : ∠PGS

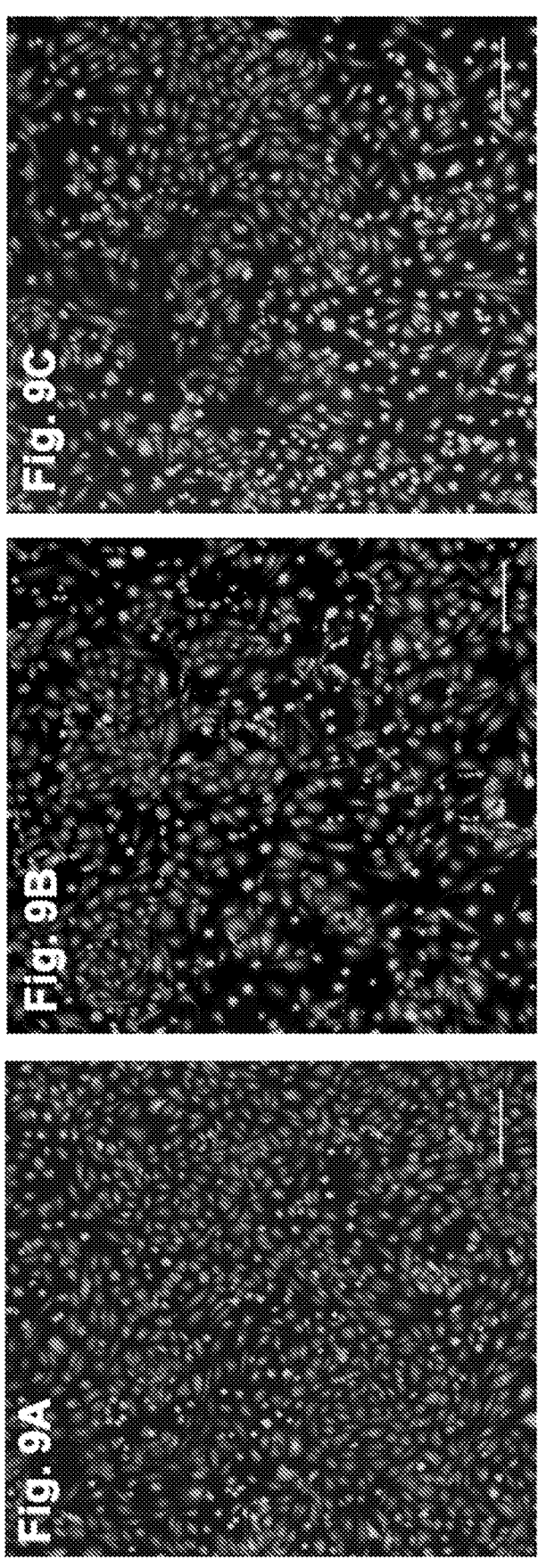

POLYMERIZATIONS IN SUPERCRITICAL CARBON DIOXIDE, PRODUCTS OF SAME, AND USES THEREOF

CROSS-REFERENCE TO RELATED APPLICATIONS

This application is a U.S. national phase entry of International Application No. PCT/US2021/037274 filed Jun. 14, 2021, which claims the benefit of U.S. Provisional application Nos. 63/038,612 filed Jun. 12, 2020, and 63/040,252 filed Jun. 17, 2020, the contents of the above-identified applications are hereby fully incorporated herein by reference in their entirety.

BACKGROUND OF THE DISCLOSURE

Aliphatic polyesters can be synthesized by esterification between hydroxy and carboxyl groups through polycondensation. Polyesters have been widely employed in biomedical applications as materials for scaffolding, biomolecule encapsulation, and surface coating. Conventional melt polycondensation typically proceeds under high temperature, high vacuum, and requires long reaction time. Metal catalysts and organic solvents necessary to drive the reaction forward often introduce toxicity concerns in solvent-based polycondensation. Moreover, conventional polycondensation reactions produce polyesters with low molecular weight (MW) and intrinsically crosslinked and branched structures when using polyols and polyacids as monomers. These structural constraints limit the physicochemical properties, mechanical strength, and form stability of the resultant polyesters.

SUMMARY OF THE DISCLOSURE

In an aspect, the present disclosure provides methods of forming a polymer. The methods are at least partially carried out in subcritical carbon dioxide or supercritical carbon dioxide. The polymerizations may be condensation polymerizations. In various examples, methods of forming a polymer comprise forming a mixture of one or more monomer(s), one or more biocatalyst(s), and carbon dioxide. A polymer is formed in the mixture. Various types and combinations of monomer/monomer(s) can be used. In various examples, a monomer/monomer(s) is/are diacid monomers, polyol monomers, amino alcohol monomers, or the like, or a combination thereof. In various examples, a monomer/monomer(s) is/are amino acids, hydroxy acids, or the like, or a combination thereof. Various forms of a biocatalyst/biocatalyst(s) can be used. In various examples, a biocatalyst/biocatalyst(s) is/are selectively catalyze(s) a primary hydroxyl group over a secondary hydroxyl group in an esterification reaction with a carboxylic acid group. In various examples, a biocatalyst/biocatalyst(s) is/are selectively catalyze(s) a primary hydroxyl group over a secondary hydroxyl group of a polyol monomer in an esterification reaction with a carboxylic acid/acetate group of a diacid monomer. In various examples, a biocatalyst/biocatalyst(s) is/are an enzyme/enzyme(s). In various examples, an enzyme/enzyme(s) is/are a lipase/lipase(s). Various forms of a carbon dioxide can be used. A carbon dioxide may be a supercritical carbon dioxide fluid or a subcritical carbon dioxide liquid.

In an aspect, the present disclosure provides polymers and compositions. A composition may comprise one or more polymer(s) of the present disclosure. In various examples, a polymer is made by a method of the present disclosure. In various examples, a polymer is made using a system of the present disclosure. A polymer may be a condensation polymer or the like. A composition may comprise one or more condensation polymer(s). A polymer may be crosslinked. In various examples, a polymer, which may be a condensation polymer, is crosslinked.

In an aspect, the present disclosure provides fabricated articles. A fabricated article comprises (or is made from) one or more polymer(s) of the present disclosure, one or more or all of which may be condensation polymer(s). In various examples, the fabricated article is in the form of a molded article, an extruded article, a spun article, or a woven article. In various examples, the fabricated article is in the form of a flake, a pellet, a powder, a granule, a bar, a monolith, a sheet, a film, a fiber, a textile, a foam, or the like. In various examples, the fabricated article is in the form of a medical article, where the medical article may be implantable, biocompatible, resorbable, or a combination thereof. In various examples, the medical article is designed to replace, support, enhance, or the like, a biological structure. In various examples, the medical article is a tissue scaffold, a stent, or the like. In various examples, the medical article is a drug delivery device. In various examples, the drug delivery device is in the form of a monolith, a ring, a disc, particle, a bead, a microsphere, a nanosphere, a surface coating, or the like. In various examples, the fabricated article is a packaging material. In various examples, the packaging material is biodegradable.

In an aspect, the present disclosure provides systems for performing methods of the present disclosure. In various examples, systems are configured to carry out methods of the present disclosure and/or make polymers or compositions of the present disclosure.

BRIEF DESCRIPTION OF THE FIGURES

For a fuller understanding of the nature and objects of the disclosure, reference should be made to the following detailed description taken in conjunction with the accompanying figures herein.

FIGS. 1A-1C illustrate polycondensation for a polyester synthesis in supercritical carbon dioxide (SC-$CO_2$). (1A), Reaction scheme for a synthesis of linear poly(glycerol sebacate) ($\ell$ PGS). (1B), Schematic diagram. (1C), a SC-$CO_2$ polycondensation for a synthesis of a $\ell$ PGS. HPP: high pressure pump; FPR: forward pressure regulator; C: check valve; MV: metering valve; BV: ball valve; P: pressure indicator; T: temperature indicator; S: safety valve.

FIGS. 3A-3D illustrate control of a solid state polycondensation of $\ell$ PGS with lipase catalysis in SC-$CO_2$. (3A), Glycerol, sebacic acid, and immobilized CALB. (3B), Low $M_w$ of a $\ell$ PGS synthesized at 35 MPa and 40° C. with a reaction time of 6 h (h=hour(s)). (3C), High $M_w$ of a $\ell$ PGS synthesized at 35 MPa and 60° C. with a reaction time of 18 h. (3D), Proposed mechanism of a lipase-catalyzed polycondensation in SC-$CO_2$.

FIGS. 9A-9D illustrate live/dead and MTT assays for human umbilical vein endothelial cells cultured on the coatings of $\ell$ PGS and controls, TCPS and Regenerez®. Live/dead images: (9A) TCPS, (9B) Regenerez®, and (9C) a $\ell$ PGS (M$_n$=102,000 Da, Đ=2.63). (9D), MTT assay for metabolic activities of HUVECs. A $\ell$ PGS was synthesized in SC-CO$_2$ at 35 MPa and 60° C. for 18 h with 10 wt. % CALB. Crosslinked PGS elastomers were cured at 150° C. under 4 Pa (>99.999% vacuum) for 20 h. Data represent mean±SD (n=4). Based on linear mixed-model analysis (p<0.05), no significant difference was observed among controls and $\ell$ PGS. Scale bar: 200 μm.

DETAILED DESCRIPTION OF THE DISCLOSURE

Figure 1A:
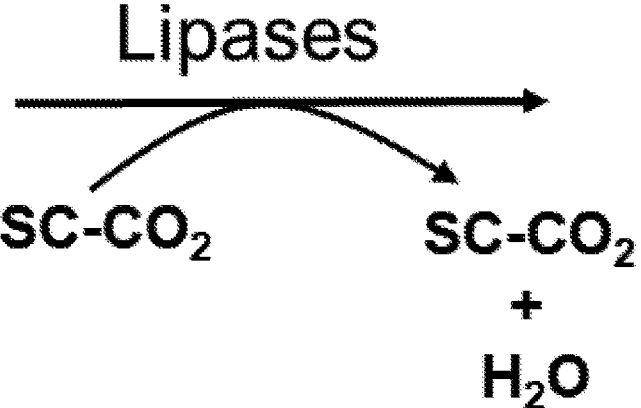

Although claimed subject matter will be described in terms of certain examples, other examples, including examples that may not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include the lower limit value, the upper limit value, and all values between the lower limit value and the upper limit value, including, but not limited to, all values to the magnitude of the smallest value (either the lower limit value or the upper limit value) of a range.

As used herein, unless otherwise stated, the term "group" refers to a chemical entity that is monovalent (i.e., has one terminus that can be covalently bonded to other chemical species), divalent, or polyvalent (i.e., has two or more termini that can be covalently bonded to other chemical species). The term "group" also includes radicals (e.g., monovalent and multivalent, such as, for example, divalent radicals, trivalent radicals, and the like). Illustrative examples of groups include:

As used herein, unless otherwise stated, the term "M$_w$" or "weight average molecular weight" is the molecular weight of a polymeric chain in determining contributions to the molecular weight average.

As used herein, unless otherwise stated, the term "M$_n$" or "number average molecular weight" is the statistical average molecular weight of all the polymer chains in the sample.

As used herein, unless otherwise stated, the term PDI or Polydispersity index refers to the ratio of the weight average molecular weight (M$_w$) the number average molecular weight (M$_n$), calculated as PDI=M$_w$/M$_n$.

The present disclosure provides methods of forming a polymer. The present disclosure also provides polymers and uses of the polymers.

In an aspect, the present disclosure provides methods of forming a polymer. The methods are at least partially carried out in subcritical carbon dioxide or supercritical carbon dioxide. In various examples, the polymerizations are condensation polymerizations or the like. Non-limiting examples of methods are provided herein. In various examples, methods of the present disclosure are used to make a polymer of the present disclosure.

The newly developed processes (examples of which include polycondensation in SC-CO$_2$ and the like) can be employed for synthesis of various polymers, such as, for example, aliphatic polyesters and the like. Non-limiting examples of polymers are provided herein.

Described in various examples herein are methods of forming a polymer comprises forming a mixture. A mixture can form a polymer. In various examples, a mixture comprises one or more monomer(s), one or more biocatalyst(s), and a carbon dioxide. In various examples, the carbon dioxide is a supercritical carbon dioxide fluid or a subcritical carbon dioxide liquid. In various examples, the mixture forms a polymer (e.g., after holding the mixture for a time and/or at a temperature, or the like). In various examples, methods of forming a polymer comprise forming a mixture comprising: one or more monomer(s); one or more biocatalyst(s); and a supercritical carbon dioxide fluid or a subcritical carbon dioxide liquid, wherein the polymer is formed.

Various types and combinations of a monomer/monomer(s) can be used. A mixture may include two or more monomers. In various examples, a monomer/monomer(s) is/are diacid monomer(s), polyol monomer(s), amino alcohol monomer(s), or the like, or a combination thereof. In various examples, a monomer/monomer(s) is/are amino acid(s), hydroxy acid(s), or the like, or a combination thereof.

In various examples, a diacid monomer is sebacic acid, succinic acid, suberic acid, adipic acid, malonic acid, glutaric acid, azelaic acid, or the like, or a combination thereof. In various examples, a polyol monomer is a diol, triol, or the like, or a combination thereof. In various examples, a diol is a 1,3-propylene diol, a 1,4-butane diol, a hydroxyl terminated oligoethylene glycol, a hydroxyl terminated polyethylene glycol, or the like, or a combination thereof. In various examples, a triol is a glycerol, a sugar, or the like, or a combination thereof. In various examples, an amino alcohol is an ethanolamine, a serinol, a sphingosine, or the like, or a combination thereof.

In various examples, an amino acid is an essential amino acid, a nonessential amino acid, or the like, or combinations thereof. In various examples, a hydroxy acid is an α-hydroxy acid, a β-hydroxy acid, or the like, or a combination thereof.

A monomer or monomers can be present in the mixture in various amounts. In various examples, two or more monomers are independently present at equimolar amounts based on the total mixture. In various examples, two or more monomers are independently present at: equimolar amounts (or relative ratios) (e.g., 0.015 mole to 0.015 mole), including +/−10%, +/−5%, or +/−1% of equimolar amounts, based on the total mixture. In various examples, two or more monomers independently include diacid monomers and polyol monomers present at equimolar amounts, including +/−10%, +/−5%, or +/−1% of equimolar amounts, based on the total mixture. In various examples, two or more monomers independently include equimolar amounts, including +/−10%, +/−5%, or +/−1% of equimolar amounts, of sebacic acid monomers and glycerol monomers based on the total volume.

Various forms of a biocatalyst/biocatalyst(s) can be used. In various examples, a biocatalyst/biocatalyst(s) selectively catalyze(s) a primary hydroxyl group over a secondary hydroxyl group in an esterification reaction with a carboxylic acid group. In various examples, a biocatalyst/biocatalyst(s) selectively catalyze(s) a primary hydroxyl group over a secondary hydroxyl group of a polyol monomer in an esterification reaction with a carboxylic acid/acetate group of a diacid monomer. In various examples, a biocatalyst/biocatalyst(s) does/do not catalyze or substantially catalyze (e.g., no detectible reaction) reaction of secondary hydroxyl group(s) (e.g., secondary hydroxyl group(s) of a polyol monomer) and a carboxylate group (e.g., acid/acetate group of a diacid monomer). In various examples, such a biocatalyst/biocatalyst(s) forms/form linear polymers.

Various biocatalysts can be used. A biocatalyst or biocatalysts may be an enzyme/enzyme(s). In various examples, a biocatalyst/biocatalyst(s) is/are chosen from enzymes and combinations thereof. In various examples, a biocatalyst/biocatalyst(s) is/are chosen from lipases and combinations thereof. In various examples, the biocatalyst/biocatalyst(s) is/are chosen from *Candida antarctica* lipase B (CALB), *Candida antarctica* Lipase A (CALA), *Thermomyces lanuginosus* lipase, *Aspergillus oryzae* Lipase, *Rhizomucor miehei* lipase, Porcine pancreatic lipase, *Pseudomonas cepacia* lipase, *Burkholderia cepacia* lipase, *Aspergillus niger* lipase, *Mucor miehei* lipase, *Pseudomonas fluorescens* lipase, *Burkholderia cepacia* lipase, *Candida rugosa* lipase, and the like, and combinations thereof.

Non-limiting examples of lipase(s) include serine hydrolases (such as, for example, *Candida antarctica* lipase B (CALB), *Candida antarctica* Lipase B, *Candida antarctica* Lipase A, *Thermomyces lanuginosus* lipase, *Aspergillus oryzae* Lipase, *Rhizomucor miehei* lipase, and the like, and combinations thereof) and the like, and combinations thereof. In various examples, a biocatalyst/biocatalyst(s) is/are chosen from the non-limiting examples of a lipase(s) listed in Table 1, and the like, and combinations thereof.

TABLE 1

| Example of lipases. | | |
| --- | --- | --- |
| Enzymes | Reaction technique | Solvent |
| *Candida antarctica* Lipase B | polycondensation/ROP | bulk/SC—CO₂ |
| Porcine pancreatic lipase | free radical polymerization/ Knoevenagel condensation | dioxane |
| *Pseudomonas cepacia* lipase | ROP | bulk |
| *Burkholderia cepacia* lipase | esterification | SC—CO₂ |
| *Aspergillus niger* lipase | Knoevenagel condensation | DMSO |
| *Mucor miehei* lipase | esterification | propanol |
| *Pseudomonas fluorescens* lipase | ROP | bulk |
| *Rhizomucor miehei* lipase | esterification | bulk |
| *Burkholderia cepacia* lipase | polycondensation | bulk |
| *Candida rugosa* lipase | polycondensation | toluene |
| *Thermomyces lanuginosus* lipase | polycondensation/ emulsion polymerization | bulk/ cyclohexane |

ROP: ring opening polymerization

In various examples, a biocatalyst/biocatalyst(s) is/are organic solvent stable, organic solvent active (examples of which are known in the art), or the like, or a combination thereof.

In various examples, the biocatalyst/biocatalyst(s) is/are chosen from homogeneous biocatalyst(s), heterogeneous biocatalyst(s) (such as, for example particle supported biocatalyst(s) and the like, and combinations thereof), and the like, and combinations thereof. In various examples, a particle supported biocatalyst/biocatalyst(s) include/includes a plurality of biocatalysts conjugated to a particle. In an example, at least a portion of or all of a biocatalyst/biocatalyst(s) is/are an enzyme/enzyme(s) is/are fixed on a bead/bead(s) of the appropriate type of resin.

Various amounts of biocatalyst(s) can be used. In various examples, a biocatalyst/biocatalyst(s) is/are present at 0.5 to 60 wt. % (e.g., 1 to 60% wt. % or 10 to 40 wt. %), including all 0.1 wt. % values and ranges therebetween, based on the weight of the monomer(s) or the weight of the biocatalyst(s) and monomer(s). In various examples, a biocatalyst/biocatalyst(s) is/are present at 0.5 to 6 wt. %, based on the weight of the monomer(s) or the weight of the biocatalyst(s) and monomer(s). In various examples, a biocatalyst/biocatalyst(s) is/are present in a mixture at 1 to 4 wt. %, based on the weight of the monomer(s) or the weight of the biocatalyst(s) and monomer(s). In various examples, a particle supported biocatalyst/biocatalyst(s) is/are loaded with a biocatalyst/biocatalyst(s) (e.g., at 5-20 wt. % biocatalyst/biocatalyst(s), 10 wt. % or more biocatalyst/biocatalyst(s), or the like). In various examples, a particle supported biocatalyst/biocatalyst(s) (e.g., including a particle/particle(s)) is/are present in a mixture at 5-60 wt. % (e.g., 10-40 wt. %), corresponding to 0.5-6 wt. % (e.g., 1-4 wt. %) biocatalyst(s) (e.g. not including a particle/particle(s)), based on the weight of the monomer(s) or the weight of the biocatalyst(s) and monomer(s).

Various forms of carbon dioxide may be used. In various examples, a carbon dioxide is a supercritical carbon dioxide fluid or a subcritical carbon dioxide liquid. In various examples, a supercritical carbon dioxide fluid has a critical temperature above 31° C. and critical pressure above 7.4 MPa.

In various examples, methods further comprise heating and/or pressurizing a carbon dioxide gas, where a supercritical carbon dioxide fluid or a subcritical carbon dioxide liquid is formed, which may be prior to forming a mixture. In various examples, heating and/or pressurizing a carbon dioxide gas forms a supercritical carbon dioxide fluid or a subcritical carbon dioxide liquid having a density of 0.47 g/m³ or more (e.g., 0.6 g/m³ or more, or 0.47 to 0.95 g/m³, including all 0.01 g/m³ values and ranges therebetween). In various examples, heating and/or pressurizing a carbon dioxide gas forms a supercritical carbon dioxide fluid or a subcritical carbon dioxide liquid having a density of 0.7 g/m³ or more.

The mixture may comprise or exclude further additives. In various examples, a mixture does not initially contain water, organic solvent(s), metal catalyst(s), metal(s) thereof, or a combination thereof, and/or the monomer(s) are not initially molten. In certain examples, a mixture is initially anhydrous. In various examples, a mixture generates water, alcohol, or other polymerization byproducts. In various examples, a mixture initially comprises water. In various examples, a mixture absorbs water from the environment. The amount of water or byproducts in a mixture (initially and/or during the polymerization reaction) may be selected. Without intending to be bound by any particular theory, it is considered that an amount of water or byproducts in the mixture can be used to control the reaction rate or extent of reaction (e.g., conversion %). In various examples, at least a portion of, substantially all, or all of water, if present, is removed from a mixture during a polymerization reaction. In various examples, a total water content in the mixture is maintained at less than 3 wt. % in favor of a biocatalyst/biocatalyst(s) (e.g., a lipase/lipase(s)) to catalyze polymerization (e.g., polycondensation).

In various examples, a mixture does not comprise an organic solvent. Non-limiting examples of organic solvent(s) include those typically used in polymerizations described herein (e.g., condensation polymerizations and the like), and the like, and combinations thereof. In various examples, a mixture is not a melt. In various examples, a mixture does not initially contain metal catalyst(s), and/or metal(s) thereof.

Various reaction conditions may be used. In various examples, a mixture is held a temperature of or a temperature of a mixture is 35 to 70° C.; and/or a mixture is held at pressure of or a pressure of a mixture is 10 to 40 MPa. In various examples, a mixture is held at a temperature of or a temperature of a mixture is 35 to 70° C., including all 0.1° C. values and ranges therebetween. In various examples, a mixture is held at a temperature of or a temperature of a mixture is 40 to 60° C., including all 0.1° C. values and ranges therebetween. In various examples, a mixture is held at a pressure of or a mixture pressure is 10 to 40 MPa, including all 0.1 MPa values and ranges therebetween. In various examples, a mixture is held at a pressure of or a mixture pressure is 25 to 35 MPa, including all 0.1 MPa values and ranges therebetween. In various examples, a monomer/monomer(s) and a biocatalyst/biocatalyst(s) is/are contacted in a mixture for a desired time and/or a desired temperature. In various examples, a monomer/monomer(s) and a biocatalyst/biocatalyst(s) is/are contacted in a mixture for 6 to 24 hours. In various examples, a monomer/monomer(s) and a biocatalyst/biocatalyst(s) is/are contacted in a mixture for 6 to 24 h, including all 0.1 hour values and ranges therebetween. In various examples, a desired time is 12 to 18 h, including all 0.1 hour values and ranges therebetween. In various examples, a mixture has a temperature of 60° C., a pressure (e.g., a carbon dioxide pressure) of 35 MPa, a density of 0.7 g/cm³, and a contact time of 12 to 18 h.

Methods can be carried in various modes of operation. In various examples, methods may be carried out in a batch mode, a semi-continuous mode, a continuous mode, or the like.

Various optional steps may be added or excluded. In various examples, methods further comprise heating and/or pressurizing a monomer/monomer(s) and a biocatalyst/biocatalyst(s) to a temperature and/or pressure of a mixture prior to forming a mixture. In various examples, methods include heating a monomer/monomer(s) and a biocatalyst/biocatalyst(s) to a desired blend temperature prior to forming a mixture. In various examples, methods include pressurizing a blend of a monomer/monomer(s) and a biocatalyst/biocatalyst(s) to a desired blend pressure prior to forming a mixture. In various examples, a desired blend temperature is 35 to 70° C., including all 0.1° C. values and ranges therebetween. In various examples, a desired blend temperature is 40 to 60° C., including all 0.1° C. values and ranges therebetween. In various examples, a desired blend pressure is 10 to 40 MPa, including all 0.1 MPa values and ranges therebetween. In various examples, a desired blend pressure is 25 to 35 MPa, including all 0.1 MPa values and ranges therebetween.

In various examples, methods further comprise continuously venting carbon dioxide (e.g., continuously venting a portion of the supercritical carbon dioxide or the subcritical carbon dioxide in the mixture) out of a mixture. In various examples, continuously venting carbon dioxide out of a mixture removes at least a portion of, substantially all, or all of water or byproducts, if present, in a mixture. In various examples herein, continuously venting carbon dioxide out of a mixture maintains a total water content of a mixture at less than 3 wt. %.

In various examples, the monomer(s) and the biocatalyst(s) are contacted in the mixture prior to continuously venting a portion of a carbon dioxide out of the mixture. In various examples, a monomer(s) and a biocatalyst(s) may be contacted for 2 h in a closed reaction vessel prior to continuously venting a portion of a carbon dioxide out of the mixture.

In various examples, methods further comprise separating the as-produced polymer from at least a portion of an unreacted monomer/monomer(s), if present, a biocatalyst/biocatalyst(s), and/or a carbon dioxide in the mixture. In various examples, an as-produced polymer may be separated from at least a portion of, substantially all, or all of a carbon dioxide by depressurizing a mixture. In various examples, a biocatalyst/biocatalyst(s) is/are separated from at least a portion of, substantially all, or all of an as-produced polymer by dissolving and filtering an as-produced polymer.

In various examples, methods further comprise crosslinking at least a portion of the polymer. The crosslinking may be thermal crosslinking. In various examples, methods further comprise thermal crosslinking at least a portion of the polymer.

A polymer can have various molecular weights. In various examples, the polymer comprises: a molecular weight ($M_w$ and/or $M_n$) of 20,000 g/mol or more; and/or a polydispersity index (PDI) of 5 or less. In various examples, a polymer has a molecular weight ($M_w$) of 20,000 g/mol or more (e.g., 30,000 g/mol or more, 20,000 to 500,000 g/mol 30,000 to 500,000 g/mol, or 40,000 to 500,000 g/mol) including all integer g/mol values and ranges therebetween; and/or a polydispersity index (PDI) of 5 or less (e.g., 2.5 or less, 5 to 1, or 2.5 to 1), including all 0.1 PDI values and ranges therebetween. The $M_w$ and/or $M_n$ of a polymer may be measured by methods known in the art. Non-limiting examples of methods of measuring $M_w$ and/or $M_n$ of a polymer are described herein.

A polymer can have various structures, In various examples, a polymer has a desirable structure selected/controlled based on a choice of a monomer/monomer(s), a biocatalyst/biocatalyst(s), a reaction condition/condition(s), etc. In various examples, a polymer is a linear polymer comprising 40% or less branching. In various examples, a polymer is a linear polymer having 40% or less branching (e.g., 35% or less, 30% or less, or 25% or less branching, or no branching). Branching may be determined by NMR spectroscopy or the like.

In various examples, a polymer is an elastomer. In various examples, an elastomer is a polyester elastomer, such as for example, an aliphatic polyester elastomer, such as a linear aliphatic polyester elastomer, or the like. The polymer may be biodegradable.

In various examples, a polymer is a copolymer (e.g., a random copolymer or the like), or the like. In various examples, a polymer is not a homopolymer.

Methods may be performed to various percent conversion of monomer. In various examples, the % conversion of a monomer(s) (based on the weight % or mol % of a monomer(s)) is 80% or more, 90% or more, 95% or more, 99% or more, 99.5% or more, or 100%. In various examples, % conversion of monomer is determined by NMR spectroscopy (e.g., ${}^1$H NMR spectroscopy or the like).

In various examples, a polymer is formed by a condensation polymerization reaction or a ring-opening polymerization reaction. In various examples, a polymer is a polyester, a polyamide, or a polyester amide. In various examples, a polyester is an aliphatic polyester. In various examples, aliphatic groups of an aliphatic polyester are, independently, $C_1$ to $C_{20}$ groups (e.g., a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{14}$, $C_{15}$, $C_{16}$, $C_{17}$, $C_{18}$, $C_{19}$, or $C_{20}$ group). Non-limiting examples of polymers include poly(glycerol sebacate) (PGS) and the like.

In various examples, a polymer comprises a plurality of unreacted secondary hydroxy groups. In various examples, a polymer is a polyester with a plurality of unreacted secondary hydroxy groups. In various examples, a polymer has a plurality of groups with linkages formed via primary hydroxyl groups (e.g., a polyester comprising a plurality of 1,3-glyceride groups, which may be 1,3-disubstituted glyceride groups). In various examples, the polymer has 50% or more, 60% or more, 70% or more, 80% or more, or 90% or more groups with linkages formed via primary hydroxyl groups (e.g., a polyester comprising 50% or more, 60% or more, 70% or more, 80% or more, or 90% or more 1,3-glyceride groups, which may be 1,3-disubstituted glyceride groups). In various examples, primary hydroxyl groups are groups formed from a polyol monomer/monomer(s).

In various examples, a polymer is crosslinked. In various examples, the polymer is a crosslinked polyester with a plurality of crosslinked secondary hydroxy groups.

In various example, a method has one or more or all of the following features:

Produces desirably high molecular weight aliphatic polyesters and/or controlled linearity of aliphatic polyester synthesis.

Continuous removal of byproducts, such as water molecules, during polymerization (e.g., polycondensation and the like) in SC-CO$_2$, which may be carried out using a system of the present disclosure.

Control of polymer chain and molecular weight by adjusting operating temperature, pressure, and processing time.

Maintaining molar ratio of monomers accurately during polymerization (e.g., polycondensation and the like) in SC-CO$_2$.

Improved plasticization and reduced matrix viscosity by SC-CO2 to facilitate the polymerization (e.g., condensation and the like) reaction.

Mild operating temperature of 40 to 60° C. and inert CO$_2$ medium desirable for use of biocatalysts, such as, for example, lipases.

Accelerated reaction achieved within, for example, 12-18 hours.

A solvent-free process without extra cost and treatments for solvent removal

Scalable capacity for industrial scale production

An improved solid state polymerization (e.g., polycondensation and the like) employing efficient diffusivity and swelling capability of SC-CO$_2$.

Concomitant sterilization of synthesized polymers during depressurization.

In various examples, methods comprise condensation polymerization in supercritical (SC)-CO$_2$ using a system comprising a high-pressure pump (HPP) and a supercritical fluid reservoir connected to a high-pressure reaction vessel. In various examples, CO$_2$ is pressurized and heated to a supercritical state in the reservoir and is introduced into the reaction vessel. In various examples, the methods comprise sample mixing and loading (e.g., diacid(s), polyol(s), and lipase(s), etc.), oligo-ester formation, polycondensation, and depressurization. In various examples, after an initial incubation period (e.g., about 2 h) and oligo-esters and water formation, a small amount of SC-CO$_2$ is continuously flowed to the vent, removing water with it during polycondensation (e.g., for about 6-18 h). In various examples, the reaction setup is depressurized for reaction termination and polymer harvest (isolation). In various examples, the methods are performed using one or more or all of the polymerization(s), system component(s), and reaction condition(s) of a system of the present disclosure (e.g., a system of FIGS. 1A-1C).

In an aspect, the present disclosure provides polymers and compositions. A composition may comprise one or more polymer(s) of the present disclosure. In various examples, a polymer is made by a method of the present disclosure. In various examples, a polymer is made using one or more of or all of the polymerization(s), system component(s), and reaction condition(s) of a system of the present disclosure (e.g., a system of FIGS. 1A-IC). Non-limiting examples of polymers provided herein.

A polymer may be a condensation polymer or the like. A composition may comprise one or more polymers, one or more or all of which may be condensation polymers. In various examples, the polymer is crosslinked.

A polymer can have various molecular weights, polydispersity values, and degrees of branching. In various examples, a polymer has a molecular weight ($M_w$ and/or $M_n$) of 20,000 g/mol or more; the polymer has a polydispersity index (PDI) of 5 or less; and/or the polymer comprises 40% or less branching. In various examples, a condensation polymer has a molecular weight ($M_w$) of 30,000 g/mol or more, 30,000 to 500,000 g/mol, or 40,000 to 500,000 g/mol; a polydispersity index (PDI) of 2.5 or less, 5 or less, 5 to 1, or 2.5 to 1; and/or 40% or less, 35% or less, 30% or less, or 25% or less branching. In various examples, the $M_w$ and/or $M_n$ of a polymer may be measured by methods known in the art. Non-limiting examples of methods of measuring $M_w$ and/or $M_n$ of a polymer are described herein.

A polymer can have various properties. In various examples, the polymer sustains (e.g., does not fail after) 100 cycles or more at 70% tensile strain; the polymer exhibits a strain at fracture of 200% or more; the polymer exhibits an ultimate tensile stress (UTS) of 1.2 MPa or more; and/or the polymer exhibits a Young's Modulus of 1.2 MPa or less. In various examples, a condensation polymer may: sustain 100 cycles or more, 200 cycles or more, 300 cycles or more, 400 cycles or more, or 500 cycles or more at 70% tensile strain; exhibit a strain at fracture of 200% or more, 250% or more, 300% or more, 350% or more, or 370% or more; exhibit a UTS of 1.2 MPa or more, 1.4 MPa or more, or 1.6 MPa or more; and/or exhibit a Young's Modulus of 1.2 MPa or less, 1 MPa or less, 0.8 MPa or less, 0.6 MPa or less, or 0.4 MPa or less.

A polymer may be a polyester, a polyamide, or a polyester amide. A polymer may be poly(glycerol sebacate) (PGS).

A polymer may be a polyester where the ester bonds are mostly (for example over 80 or over 90%) derived primary alcohols. A very small amount (for example, less than 20% or less than 10%) of the ester bonds may be derived from secondary or tertiary alcohols.

In various examples, an as-produced polymer, which may be a condensation polymer or the like, is not subjected to post-synthesis purification and/or separation processes. In various methods, an as-produced polymer does not contain a substantial amount (e.g., a detectable amount) of an organic solvent(s), a metal catalyst(s), and/or a metal(s) thereof. Non-limiting examples of a metal catalyst(s) or a metal(s) of a metal catalyst(s) include those typically used in polymerizations described herein (e.g., condensation polymerizations and the like), and the like, and combinations thereof. The presence or absence metal catalyst(s) or metal(s) of a metal catalyst(s) may be measured by methods known in the art. Non-limiting examples of organic solvent(s) include those typically used in polymerizations described herein (e.g., condensation polymerizations and the like), and the like, and combinations thereof. The presence or absence metal catalyst(s) or metal(s) of a metal catalyst(s) may be measured by methods known in the art.

In various examples, an as-produced polymer is separated from at least a portion of, substantially all, or all of an unreacted monomer/monomer(s), if present, a biocatalyst/biocatalyst(s), and/or a carbon dioxide.

In various examples, a polymer may be an elastomer. In various examples, an elastomer is a polyester elastomer, such as for example, an aliphatic polyester elastomer, such as a linear aliphatic polyester elastomer. The polymer may be biodegradable.

In various examples, a polymer is a copolymer (e.g., a random copolymer or the like), or the like. In various examples, a polymer is not a homopolymer.

In various examples, a polymer is a polyester, a polyamide, or a polyester amide. In various examples, a polyester may be an aliphatic polyester. In various examples, the aliphatic groups of an aliphatic polyester are, independently, $C_1$ to $C_{20}$ groups (e.g., a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{14}$, $C_{15}$, $C_{16}$, $C_{17}$, $C_{18}$, $C_{19}$, or $C_{20}$ group). Non-limiting examples of polymers include poly(glycerol sebacate) (PGS) and the like.

In an aspect, the present disclosure provides fabricated articles. A fabricated article comprises (or is made from) one or more polymer(s) of the present disclosure, one or more or all of which may be condensation polymer(s). Non-limiting examples of fabricated articles are provided herein.

In various examples, a fabricated article is in the form of a molded article, an extruded article, a spun article, a woven article, or the like. In various examples, a fabricated article is in the form of a flake, a pellet, a powder, a granule, a bar, a monolith, a sheet, a film, a fiber, a textile, a foam, or the like. In various examples, a fabricated article is in the form of a medical article, which may be implantable, biocompatible, resorbable, or a combination thereof.

In various examples, a medical article is designed to replace, support, enhance, or the like, a biological structure. In various examples, a medical article is a tissue scaffold, a stent, or the like. In various examples, a medical article is a drug delivery article or the like, such as, for example, a drug delivery device. In various examples, a medical article is in the form of a monolith, a ring, a disc, particle, a bead, a microsphere, a nanosphere, a surface coating, or the like.

In various examples, a fabricated article is a packaging material. In various examples, a packaging material is biodegradable.

In an aspect, the present disclosure provides systems for performing the methods of the present disclosure. In various examples, a system is configured to carry out a method of the present disclosure and/or make a composition or polymer of the present disclosure. Non-limiting examples of systems are disclosed herein.

A system can have various components. In various examples, a system, which is a system for polymerization, such as, for example, condensation polymerization in supercritical (SC)-$CO_2$, comprises a high-pressure pump (HPP) and a supercritical fluid reservoir connected to (e.g., in fluid connection with) a high-pressure reaction vessel. In various examples, a supercritical fluid reservoir is configured to pressurize and/or heat $CO_2$ to, a supercritical or sub-critical state in the reservoir and introduce supercritical or sub-critical $CO_2$ into the reaction vessel. In various examples, a high-pressure reaction vessel is configured to load and/or mix reactant(s) (e.g., monomer(s), such as, for example, diacid(s), polyol(s), and the like, or a combination thereof), lipase(s), etc.) and/or pressurization and/or depressurization and/or venting (such as, for example, continuously venting) $CO_2$. In various examples, the system comprises one or more of or all of the polymerization(s), system component(s), and reaction condition(s) of a system of the present disclosure (e.g., the system of FIGS. 1A-1C).

The following Statements describe various examples of methods of forming polymers, polymers, cross-linked polymers, and compositions of the present disclosure.

Statement 1. A method of forming a polymer comprising (or consisting essentially of or consisting of): forming a mixture (which may be referred to as a reaction mixture) comprising: one or more (e.g., two or more) monomer(s); one or more biocatalyst(s); and carbon dioxide (e.g., carbon dioxide gas that is supercritical carbon dioxide gas (also known as supercritical carbon dioxide fluid) or subcritical carbon dioxide gas (also known as subcritical carbon dioxide liquid) (e.g., carbon dioxide gas having a density of 0.6 $g/m^3$ or more), wherein the polymer is formed.

Statement 2. A method according to Statement 1, wherein the method further comprises separating at least a portion of, substantially all, or all of one or more of the unreacted monomer(s), if present, and/or at least a portion of, substantially all, or all of the carbon dioxide from at least a portion of, substantially all, or all of the polymer.

Statement 3. A method according to Statement 1 or 2, wherein the one or more (e.g., two or more) monomer(s) are chosen from diacids (such as, for example, sebacic acid, succinic acid, suberic acid, adipic, malonic, glutaric, and azelaic acid, and the like, and combinations thereof), polyols (such as, for example, glycerol, ethylene glycol, propylene glycol, sucrose, and the like, and combinations thereof), amino alcohols (such as, for example, ethanolamine, serinol, sphingosine, and the like, and combinations thereof), and the like, and combinations thereof.

Statement 4. A method according to any one of the preceding Statements, wherein the one or more (e.g., two or more) monomer(s) is/are independently present in an equimolar amount (e.g., at 0.015 mole to 0.015 mole) (based on the total mixture, which may be a reaction mixture), including all 0.001 mole values and ranges therebetween, and/or a +/−10%, 5%, or 1% (independently) of an equimolar amount (or relative ratio).

Statement 5. A method according to any one of the preceding Statements, wherein the one or more biocatalyst(s) is/are chosen from enzymes, or the like, or a combination thereof.

Statement 6. A method according to any one of the preceding Statements, wherein the one or more biocatalyst(s) is/are present at 1 to 60% wt. % (e.g., 10 to 40 wt. %), including all 0.1 wt % values and ranges therebetween.

Statement 7. A method according to any one of the preceding Statements, wherein a polymer is a polyester, a polyamide, a polyester amide, or the like, or a combination thereof.

Statement 8. A method according to any one of the preceding Statements, wherein the polymer has a molecular weight ($M_w$) of 20,000 or more (e.g., 20,000-500,000 g/mol, including all integer g/mol values and ranges therebetween, such as, for example, 30,000-350,000 g/mol or 40,000-500,000 g/mol) and/or a polydispersity index (PDI) of 5 or less (e.g., 2.5 or less, 5-1, or 2.5-1).

Statement 9. A polymer (which may be made by a method of any one of Statements 1-8) or a composition comprising a polymer.

Statement 10. A polymer or composition comprising a polymer according to Statement 9, wherein the polymer is a polyester, a polyamide, polyester amide, or the like, or a combination thereof.

Statement 11. A polymer or composition comprising a polymer according to any one of Statements 9 or 10, wherein the polymer has a molecular weight ($M_w$ and/or $M_n$) 30,000 or more (e.g., 30,000-500,000 g/mol, including all integer g/mol values and ranges therebetween, such as, for example, 30,000-350,000 g/mol or 40,000-500,000 g/mol) and/or a polydispersity index (PDI) of 5 or less (e.g., 2.5 or less, 5-1, or 2.5-1).

Statement 12. A polymer or composition comprising a polymer according to any one of Statement 9-11, where the ester bonds are mostly (for example over 80 or over 90%) derived primary alcohols, with very small amount derived from secondary or tertiary alcohols.

Statement 13. A polymer or composition comprising a polymer according to any one of Statements 9-11, wherein the polymer exhibit one or more or all of the following: the polymer does not have: any substantial amount (e.g., a detectible amount) of a metal catalyst(s) or metal(s) of a metal catalyst(s), wherein the as-produced polymer is not subjected to any post-synthesis purification and/or separation process; any substantial amount (e.g., a detectible amount) of an organic solvent(s), wherein the as-produced polymer is not subjected to any post-synthesis purification and/or separation process.

The steps of the methods described in the various embodiments and examples disclosed herein are sufficient to produce a polymer of the present disclosure or carry out methods of the present disclosure. Thus, in various embodiments, methods consist essentially of a combination of the steps of the methods disclosed herein. In various other embodiments, methods consist of such steps.

The following examples are presented to illustrate the present disclosure. These examples are not intended to be limiting in any manner.

Example 1

The following are examples of methods and polymers of the present disclosure.

In an example, poly(glycerol sebacate) (PGS), a representative elastomer for polyester polyols prepared by polycondensation between a polyol and a diacid, is synthesized by the methods of the present disclosure.

Polycondensation can use simple and readily available monomers; however, it is difficult to produce high molecular weight polymers. A sustainable process was designed using a continuous flow reactor with supercritical carbon dioxide ($SC\text{-}CO_2$) as a solvent and lipase as a biocatalyst for polycondensation between 40 and 60° C. within 18 hours, much milder and shorter than conventional syntheses usually conducted at temperature higher than 100° C. for reaction time longer than 72 h. The continuous flow of $SC\text{-}CO_2$ extracts the byproduct (water), driving the reaction forward (FIG. 1A). Poly(glycerol sebacate) (PGS), a representative elastomer for polyester polyols prepared by polycondensation between a polyol and a diacid, is synthesized with molecular weight approximately 30-fold of those made by conventional polycondensation. Enzymatic catalysis produces polyesters with a more defined structure, in sharp contrast to conventional PGS with ~45% branching structure. Improved size, uniformity, and linearity of the polymers can be controlled with adjusting operating conditions (temperature, pressure, lipase content, and reaction time), which makes a profound impact on mechanical properties of the crosslinked elastomers.

The challenges of conventional polycondensation are overcome by using an enzyme in supercritical carbon dioxide (SC-CO$_2$) to produce high MW linear polyesters from a polyol and a diacid. Under anhydrous conditions, the lipase specifically catalyzes reactions between primary hydroxy groups and carboxyl groups while avoiding secondary hydroxy groups, thereby enabling formation of linear polyesters when polyols are monomers. A serine hydrolase, *Candida antarctica* lipase B (CALB), is widely preferred as a nontoxic catalyst to synthesize polyesters. However, existing lipase-based reactions generate polyesters with MW<30,000 Da.

Figure 1B:
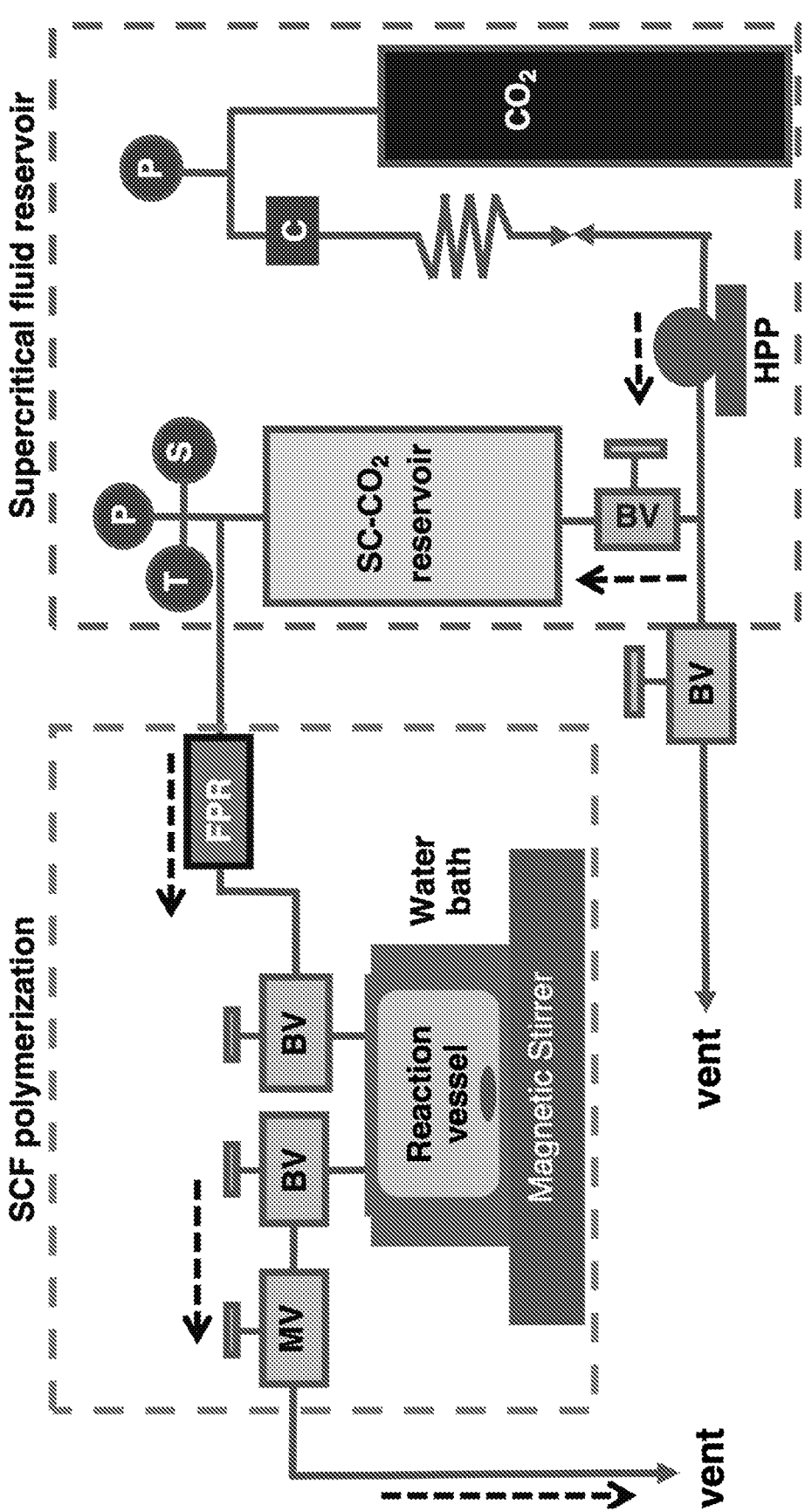

Here, a continuous flow reaction platform to drive condensation forward by removing water, the byproduct, was used. Pressurized above its critical point at 7.39 MPa and 31.1° C., CO$_2$ enters a supercritical state, a homogeneous phase possessing gas-like diffusivity and tunable solvation strength, with its inert nature and sustainability as additional benefits. Water dissolves in SC-CO$_2$ at 0.1 mol %, but not in CO$_2$ under the ambient condition. Instead of using a conventional closed reaction vessel, continuous bleeding out of a small amount of SC-CO$_2$ that carries water out of the reaction mixture was performed. This bleeding has little impact on polymer yield because the aliphatic polyesters with M$_w$>20,000 Da exhibit immiscibility with SC-CO$_2$ at 30 MPa and 35° C. Instead, the latter diffuses into the polymer matrix, significantly plasticizing and swelling the polymer melt, thereby allowing continuous esterification.

degradation profiles, serves as a representative model for polycondensation between a polyol and a diacid (FIG. 1A). The reaction platform consisted of a high-pressure pump (HPP) and a supercritical fluid reservoir connected to a 50-ml high-pressure reaction vessel (FIG. 1B). CO$_2$ was pressurized and heated to a supercritical state in the reservoir and introduced into the reaction vessel, as indicated by the blue dashed arrows. After an initial incubation period of 2 h when oligo-esters and water formed, a small amount of SC-CO$_2$ continuously flowed to the vent, removing water. The total processing time was 9-21 h (FIG. 1C), shorter than typical polycondensation reactions which usually require the reaction time longer than 72 h at a temperature higher than 100° C.

The polymers synthesized using this new reaction system is effectively linear, thus referred to as ℓ PGS. ℓ PGS produced in SC-CO$_2$ with ≥10 wt. % CALB loading ℓ exhibited higher MW than PGS synthesized by conventional methods including the commercially sourced and those prepared in-house (Table 2). A quick round of optimization produced ℓ PGS with M$_n$ of 102,000 Da and a dispersity index (Đ) of 2.63 for a reaction time of 18 h, approaching to the theoretical Đ value of 2 derived from the Carothers theory and Flory's equal reactivity principle.

TABLE 2

Molecular weights, dispersity indexes, and thermal properties of ℓ PGS synthesized using SC—CO$_2$ polycondensation in optimized conditions.

| Synthesis of ℓ PGS | M$_w$ (Dalton, Da) | M$_n$ (Dalton, Da) | Đ | T$_{m1}$$^a$ (° C.) | T$_{m2}$$^b$ (° C.) | T$_c$ (° C.) | T$_g$ (° C.) |
|---|---|---|---|---|---|---|---|
| Regenerez ® | 7,200 | 2,700 | 2.63 | 9.2 | 25.8 | −11.2 | −17.4 |
| In-house conventional method$^c$ | 22,000 | 4,100 | 5.31 | 7.1 | 24.2 | −12.2 | −16.5 |
| ℓ PGS with 10 wt. % CALB$^d$ | 185,000 | 13,000 | 14.74 | 8.6 | | −14.8 | −18.3 |
| ℓ PGS with 20 wt. % CALB$^d$ | 145,000 | 29,000 | 4.94 | 10.8 | | −6.0 | −16.6 |
| ℓ PGS with 40 wt. % CALB$^d$ | 195,000 | 56,000 | 3.46 | 15.1 | | −11.2 | −17.8 |
| ℓ PGS with 10 wt. % CALB for 18 h$^e$ | 269,000 | 102,000 | 2.63 | 7.5 | | −13.8 | −24.6 |

$^a$Melting point at lower temperature
$^b$Melting point at higher temperature
$^c$Melt polycondensation at 120° C. for 72 h under vacuum
$^d$35 MPa, 60° C. and the reaction time of 12 h in SC—CO$_2$
$^e$35 MPa, 60° C. and the reaction time of 18 h in SC—CO$_2$
$^f$All molecular weight data were measured using GPC under the identical condition.
$^g$CALB is immobilized on the acrylic-resin beads with 10 wt. % loading efficiency. The listed weight includes that of the beads.

The resultant polymers reach M$_n$ as high as 102,000 Da with >75% linearity, much more improved than reported polyesters produced using conventional techniques.

Results and discussion. Poly(glycerol sebacate) (PGS), an elastomeric polyester with high biocompatibility and linear Temperature, pressure, catalyst amount, and reaction time controlled the molecular weight of the synthesized ℓ PGS (Tables 2 and 3). With higher temperature and pressure, SC-CO$_2$ enhanced its solvation strength and diffusivity for improving plasticization in polymer matrix.

TABLE 3

Molecular weights and dispersity indexes of ℓ PGS synthesized in SC—CO$_2$ for process optimization.

| No. | Pressure (MPa) | Temperature (° C.) | Time (h) | CALB (wt. %) | M$_w$ (Dalton, Da) | M$_n$ (Dalton, Da) | Đ |
|---|---|---|---|---|---|---|---|
| 1 | 35 | 60 | 6 | 10 | 5,500 | 3,500 | 1.57 |
| 2 | 35 | 60 | 12 | 10 | 185,000 | 13,000 | 14.74 |
| 3 | 35 | 60 | 18 | 10 | 269,000 | 102,000 | 2.63 |
| 4 | 35 | 60 | 6 | 20 | 5,000 | 3,200 | 1.55 |
| 5 | 35 | 60 | 12 | 20 | 145,000 | 29,000 | 4.94 |
| 6 | 35 | 60 | 18 | 20 | 22,000 | 9,200 | 2.34 |
| 7 | 35 | 60 | 12 | 40 | 195,000 | 56,000 | 3.46 |
| 8 | 35 | 60 | 12 | 5 | 3,000 | 2,400 | 1.24 |

TABLE 3-continued

| | | | | | Molecular weights and dispersity indexes of ⅄ PGS synthesized in SC—CO$_2$ for process optimization. | | |
| No. | Pressure (MPa) | Temperature (° C.) | Time (h) | CALB (wt. %) | M$_w$ (Dalton, Da) | M$_n$ (Dalton, Da) | Đ |
|---|---|---|---|---|---|---|---|
| 9 | 35 | 50 | 6 | 10 | 1,600 | 1,600 | 1.06 |
| 10 | 35 | 40 | 4 | 8 | 1,200 | 1,200 | 1.00 |
| 11 | 35 | 40 | 8 | 8 | 3,300 | 2,500 | 1.31 |
| 12 | 35 | 40 | 18 | 8 | 6,600 | 3,000 | 2.16 |
| 13 | 35 | 40 | 24 | 8 | 12,000 | 3,100 | 3.89 |
| 14 | 25 | 60 | 6 | 10 | 1,700 | 1,500 | 1.12 |
| 15 | 25 | 60 | 12 | 20 | 78,000 | 10,000 | 7.80 |

The increase in MW of ⅄ PGS was pronounced with elevation of the operating pressure (Table 4).

TABLE 4

| | | | | Effects of operating pressure on molecular weights of ⅄ PGS synthesized in SC—CO$_2$. | | |
| Pressure (MPa) | Temperature (° C.) | Time (h) | CALB (wt. %) | M$_w$ (Da) | M$_n$ (Da) | Đ |
|---|---|---|---|---|---|---|
| 25 | 60 | 6 | 10 | 1,700 | 1,500 | 1.12 |
| 35 | 60 | 6 | 10 | 5,500 | 3,500 | 1.57 |
| 25 | 60 | 12 | 20 | 78,000 | 10,000 | 7.80 |
| 35 | 60 | 12 | 20 | 145,000 | 29,000 | 4.94 |

Figure 2:
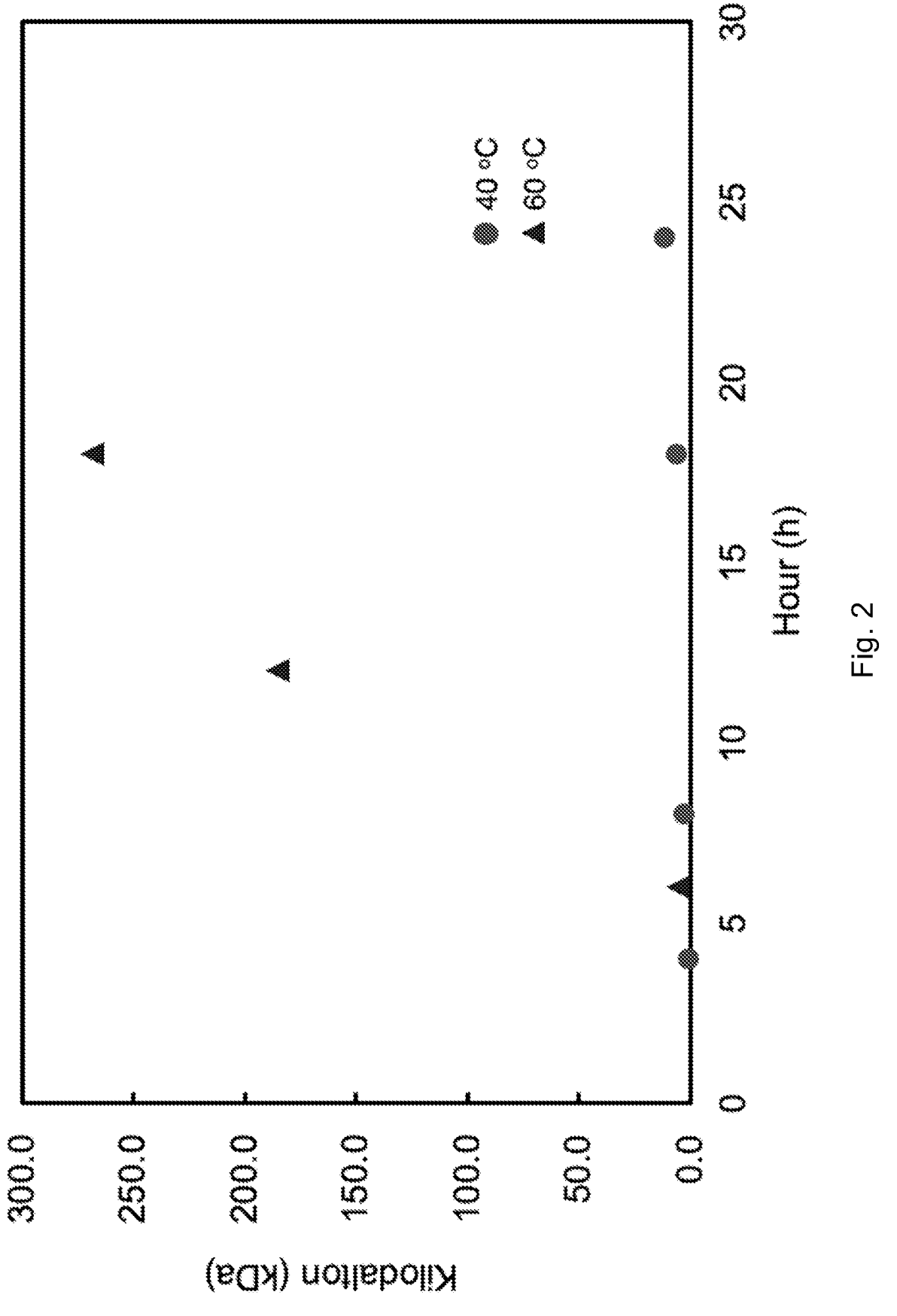
FIG. 2 illustrates weight-average molecular weight (MW) variations of $\ell$ PGS synthesized in SC-$CO_2$ at 35 Megapascal (MPa) and 10 wt. % *Candida antarctica* lipase B (CALB) with different operating temperatures and reaction times.

Raising the reaction temperature from 40 to 60° C. improved M$_w$ of the polymer 40-fold (FIG. 2). However, both offered limited benefits and increased risk beyond a certain point. In this case, the pressure was limited to 35 MPa to minimize potential leaking during reaction. The reaction temperature was set at 60° C. for maximum catalytic activity of CALB, based on our optimization study. Raising enzyme loading also generally increased M$_w$ and M$_n$ and decreased the Đ value (Table 5).

TABLE 5

| | Effects of lipase contents on molecular weights of ⅄ PGS synthesized in SC—CO$_2$. | | |
| CALB (wt. %) | M$_w$ (Da) | M$_n$ (Da) | Đ |
|---|---|---|---|
| 5 | 3,000 | 2,400 | 1.24 |
| 10 | 185,000 | 13,000 | 14.74 |
| 20 | 145,000 | 29,000 | 4.94 |
| 40 | 195,000 | 56,000 | 3.46 |

⅄ PGS was synthesized in SC—CO$_2$ at 35 MPa and 60° C. for 12 h.

Nevertheless, the immobilization beads constrained the overall reaction volume. Furthermore, extending reaction time improved MW while maintaining Đ (Table 6); thus enzyme-carrying bead loading at 10 wt. % was focused on, corresponding to 1 wt. % immobilized CALB.

TABLE 6

| | Effects of reaction time on molecular weights of ⅄ PGS synthesized in SC—CO$_2$. | | |
| Reaction time (h) | M$_w$ (Da) | M$_n$ (Da) | Đ |
|---|---|---|---|
| 6 | 5,600 | 3,500 | 1.59 |
| 12 | 185,000 | 13,000 | 14.74 |
| 18 | 269,000 | 102,000 | 2.63 |

⅄ PGS was synthesized in SC—CO$_2$ at 35 MPa and 60° C. with 10 wt. % CALB.

Polymerization transformed the reaction mixture from white powder (FIG. 3A) to viscous liquid or resilient elastomer (FIGS. 3B-3C) depending on the reaction parameters. The proposed mechanism of lipase-catalyzed polycondensation in SC-CO$_2$ was depicted in FIG. 3D. The polymerization strategy newly developed in this study significantly increases polymer size, maintains dispersity, and decreases reaction temperature and time, while reducing negative impacts on the environment and human health. For conventional techniques, the highest molecular weight PGS reported with M$_w$ of 23,000 Da and a Đ value of 3.5 was synthesized employing melt polycondensation at 120° C. in argon followed by vacuum with a total reaction time of 53 h. Another melt polycondensation at 120° C. for 72 h generated PGS with M$_n$ of 792 Da and Đ of 7.91. CALB-catalyzed synthesis of PGS in anhydrous toluene at 100° C. for 72 h yielded the resultant polymer with M$_w$ of 4,670 Da and Đ of 2.13.

Figure 4A:
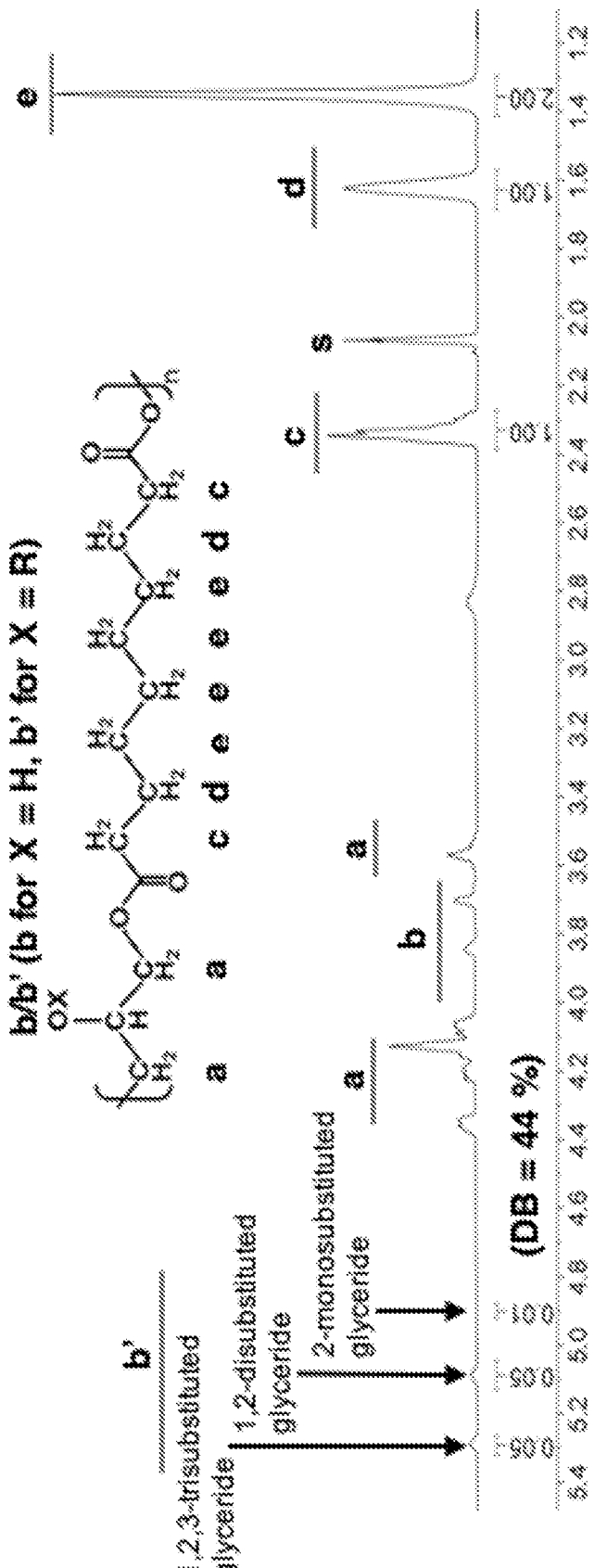
FIGS. 4A-4C illustrate polymer structure analyses using nucleic magnetic resonance spectroscopy (NMR) and Fourier-transform infrared spectroscopy (FTIR). $^1$H NMR spectra of (4A) Regenerez® and (4B) a $\ell$ PGS (number-average molecular weight ($M_n$)=102,000 Da, polydispersity (Đ)=2.63). (4C), FTIR spectra. A signal of acetone-d$_6$ (S) appears at 2.08 ppm in NMR spectra. DB refers to degree of branching.
Figure 4B:
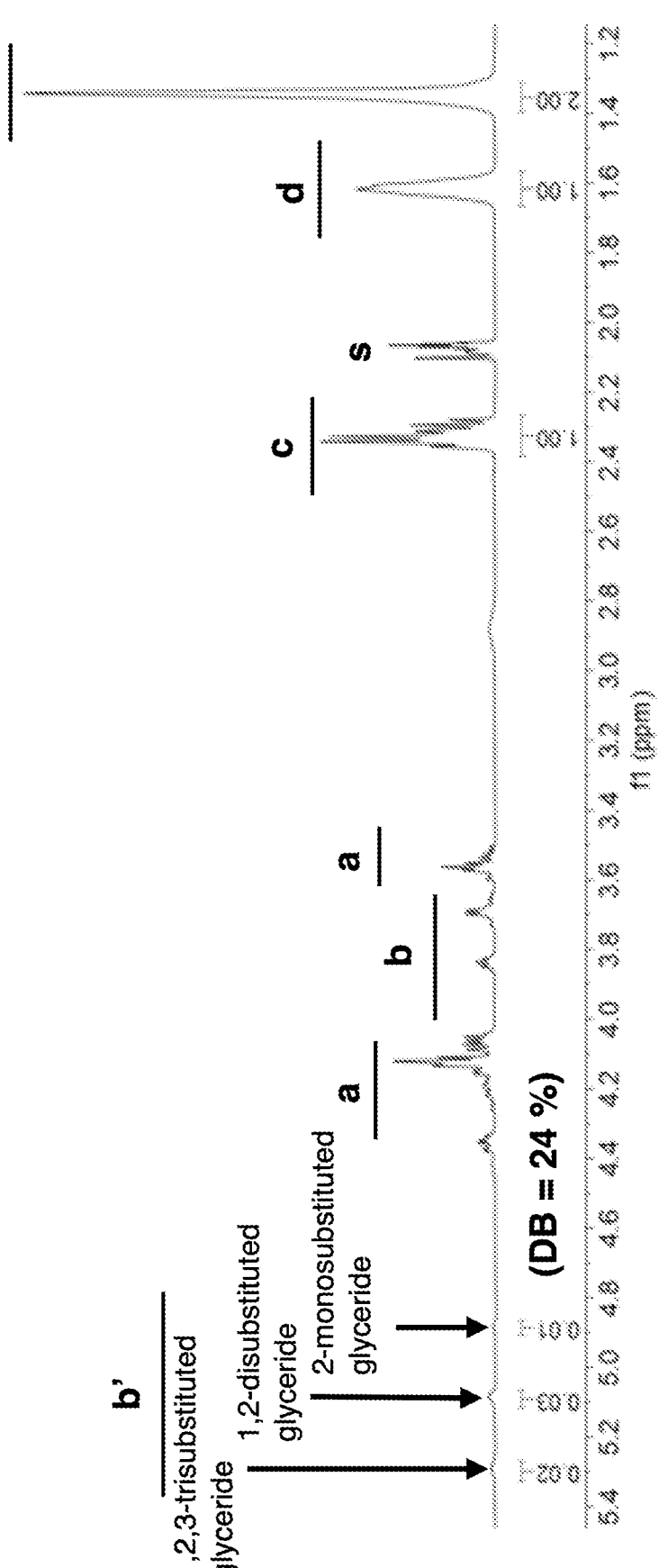
Figure 4C:
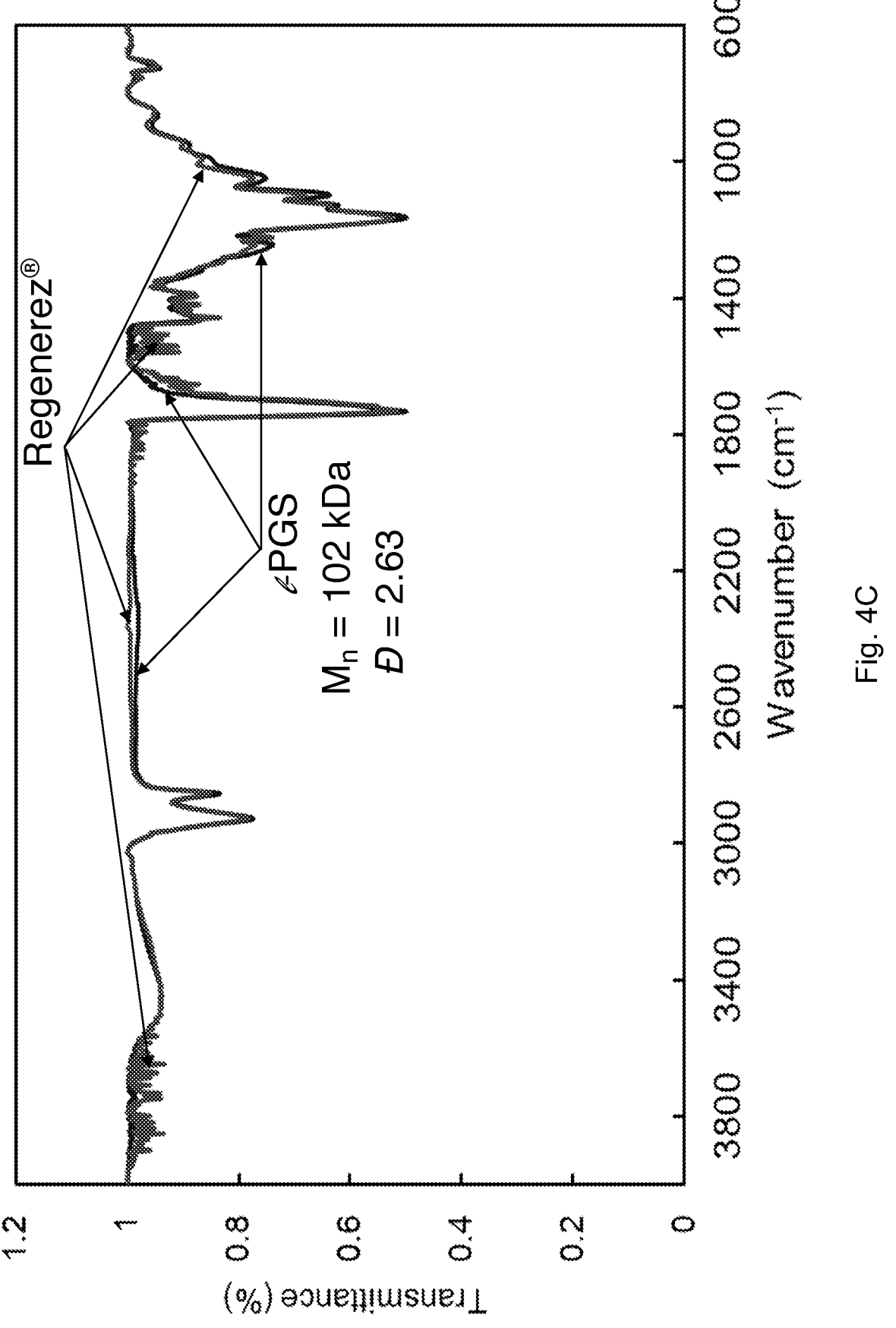
Figure 5A:
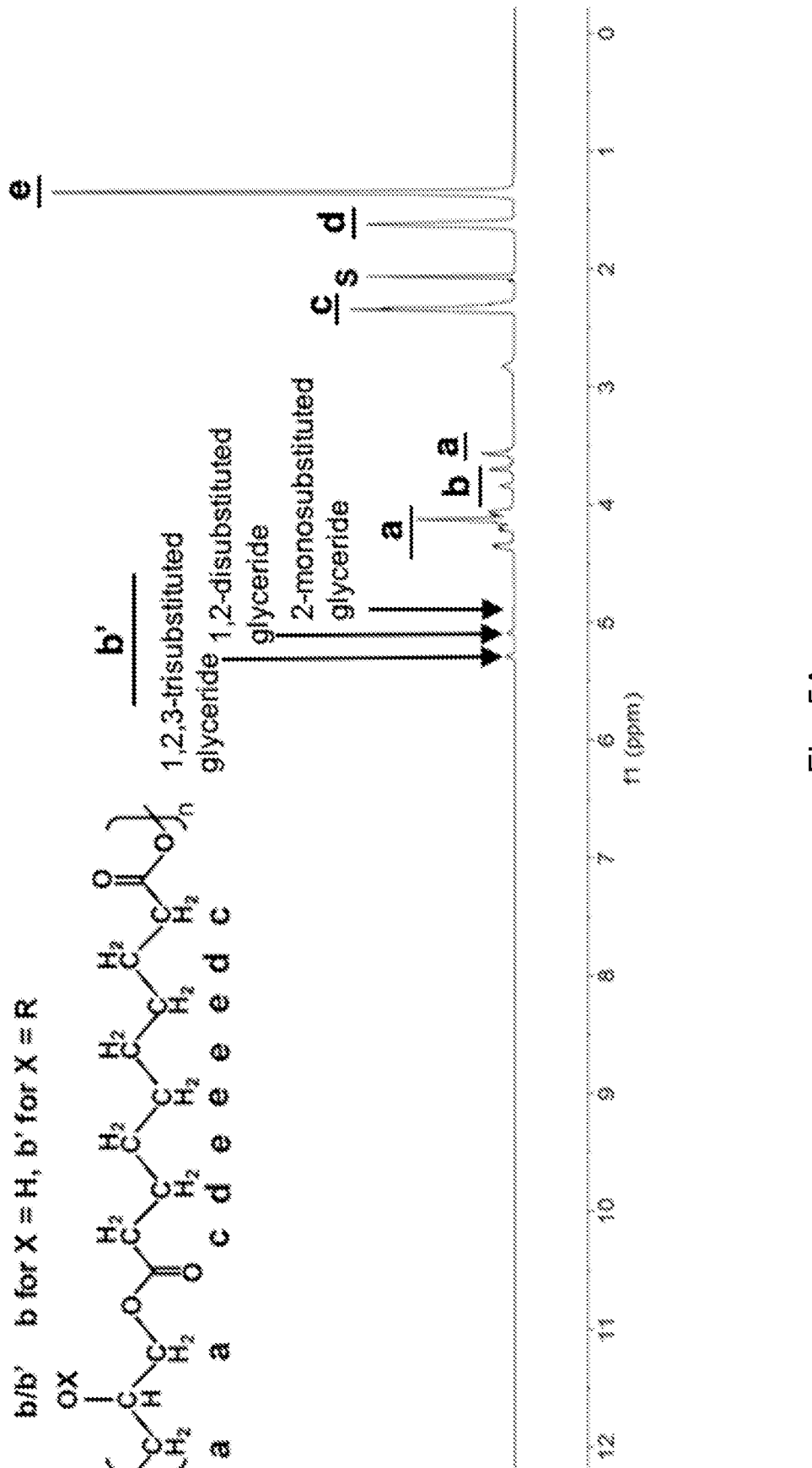
FIGS. 5A-5B illustrate full spectra of $^1$H NMR for (5A) Regenerez® and (5B) a $\ell$ PGS (M$_n$=102,000 Da, Đ=2.63). A signal of acetone-d$_6$ (S) appears at 2.08 ppm.
Figure 5B:
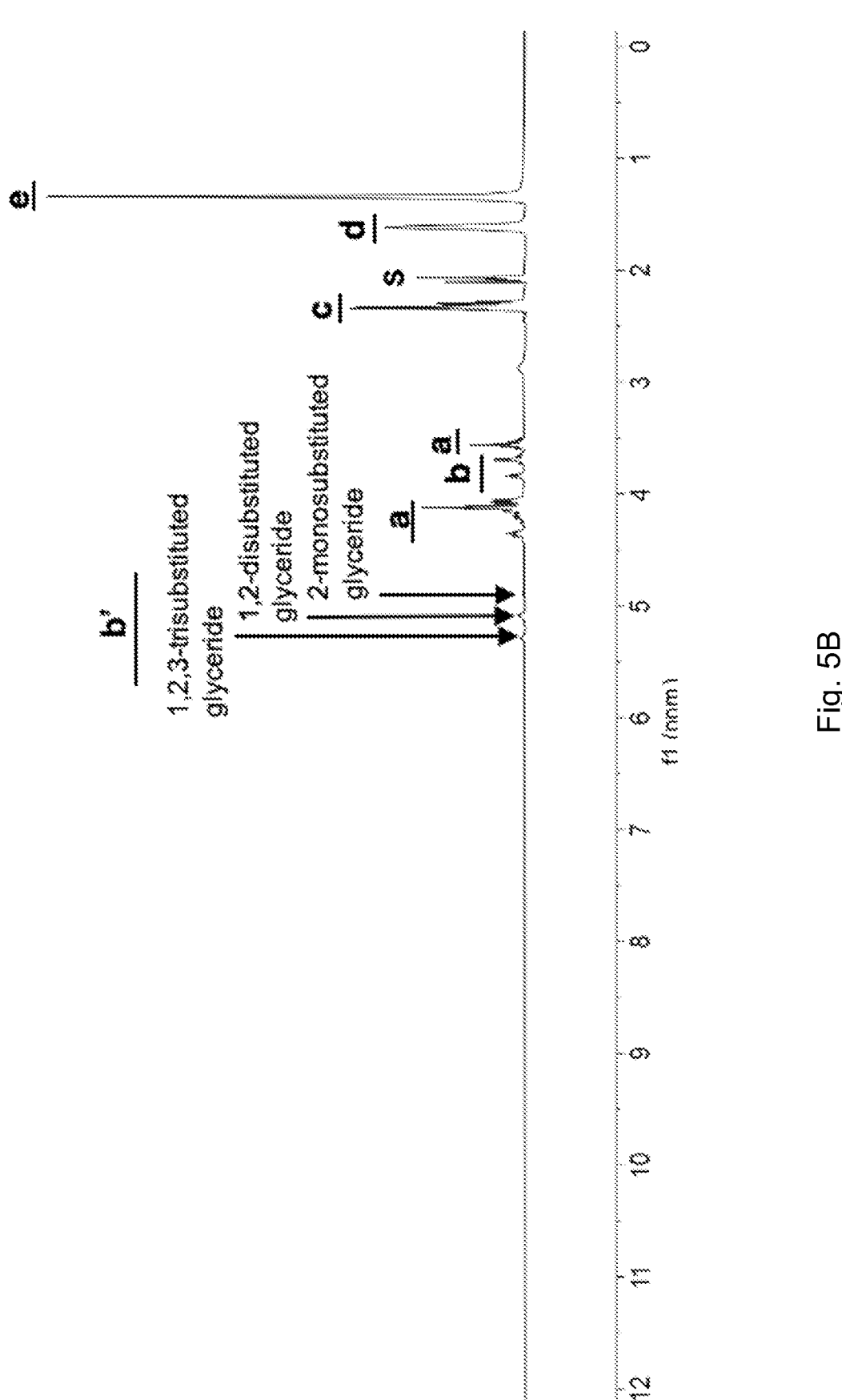

Polymer structures and thermal properties. Lipase prefers primary alcohols; thus, the secondary alcohol of glycerol can be reserved as free hydroxy groups in the polymer for further functionalization without the protection-deprotection strategy. $^1$H NMR spectra revealed that >75% of the ester bonds were of 1,3-disubstituted glycerides in as-synthesized ⅄ PGS. All glyceride protons were detected between 3.5 and 4.5 ppm. The peaks at 4.88, 5.08, and 5.29 ppm, corresponding to the methine protons of 2-monosubstituted, 1, 2-disubstituted, and trisubstituted glycerol units, indicated that <25% of secondary hydroxy groups in glycerol were esterified during SC-CO$_2$ polycondensation (FIG. 4B), compared to 44% of those in the PGS control made using melt polycondensation (FIG. 4A). The three signals marked at 1.34, 1.62, and 2.34 ppm were from the protons of sebacoyl moieties in the backbone chain, respectively. The broad peak between 2.8 and 3.0 ppm indicated the presence of hydroxy groups. Full spectra of $^1$H NMR for the control (FIG. 5A) and ⅄ PGS (FIG. 5B) showed no carboxyl groups (10 to 11 ppm in free sebacic acid), indicating a high degree of conversion. Key functional groups of PGS by FTIR (FIG. 4C) were analyzed. Generally, PGS exhibited the peaks for methylene groups (—CH$_2$) at 2854 and 2926 cm$^{-1}$, respectively. The intense stretches for the C—O bonds at 1162 cm$^{-1}$ and for the C=O bonds at 1732 cm$^{-1}$ confirmed the formation of ester bonds. The broad O—H stretch from 3350 to 3550 cm$^{-1}$ was attributed to free hydroxy groups of the glycerol moieties in the backbone chain. The reaction produced well defined polymer structure with free secondary hydroxy groups in the polymer chain and low degree of branching (DB). Mechanical strength of the crosslinked polymer should be enhanced with the regular arrangement of polymeric network. Further advantage of the regular structure is potentially more precise functionalization through the secondary alcohol, which will be examined in the future.

Thermal properties of ℓ PGS, as examined by differential scanning calorimetry (DSC), exhibited sharp crystallization and melting temperatures with subtle glass transition (FIG. 6B and Table 2). ℓ PGS ($M_n$=102,000 Da and Đ=2.63) only showed one melting temperature ($T_m$), 7.5° C. However, PGS made by the conventional method displayed two $T_m$ at 9.2 and 25.8° C. respectively (FIG. 6A), revealing a polymer with multiple molecular structures. This was consistent with the NMR analyses showing esterification of secondary hydroxy groups in conventional PGS at a higher percentage of ~45%. The crystallization temperature ($T_c$) of ℓ PGS at −13.8° C. was lower than those of conventional PGS at −11 to −12° C., consistent with the former being a larger molecule. The presence of exothermic peak at approximately −14° C. and endothermic peak at ~7.5° C. indicates that ℓ PGS is semicrystalline and completely becomes amorphous above 37° C., consistent with previous reports.

Figure 7:
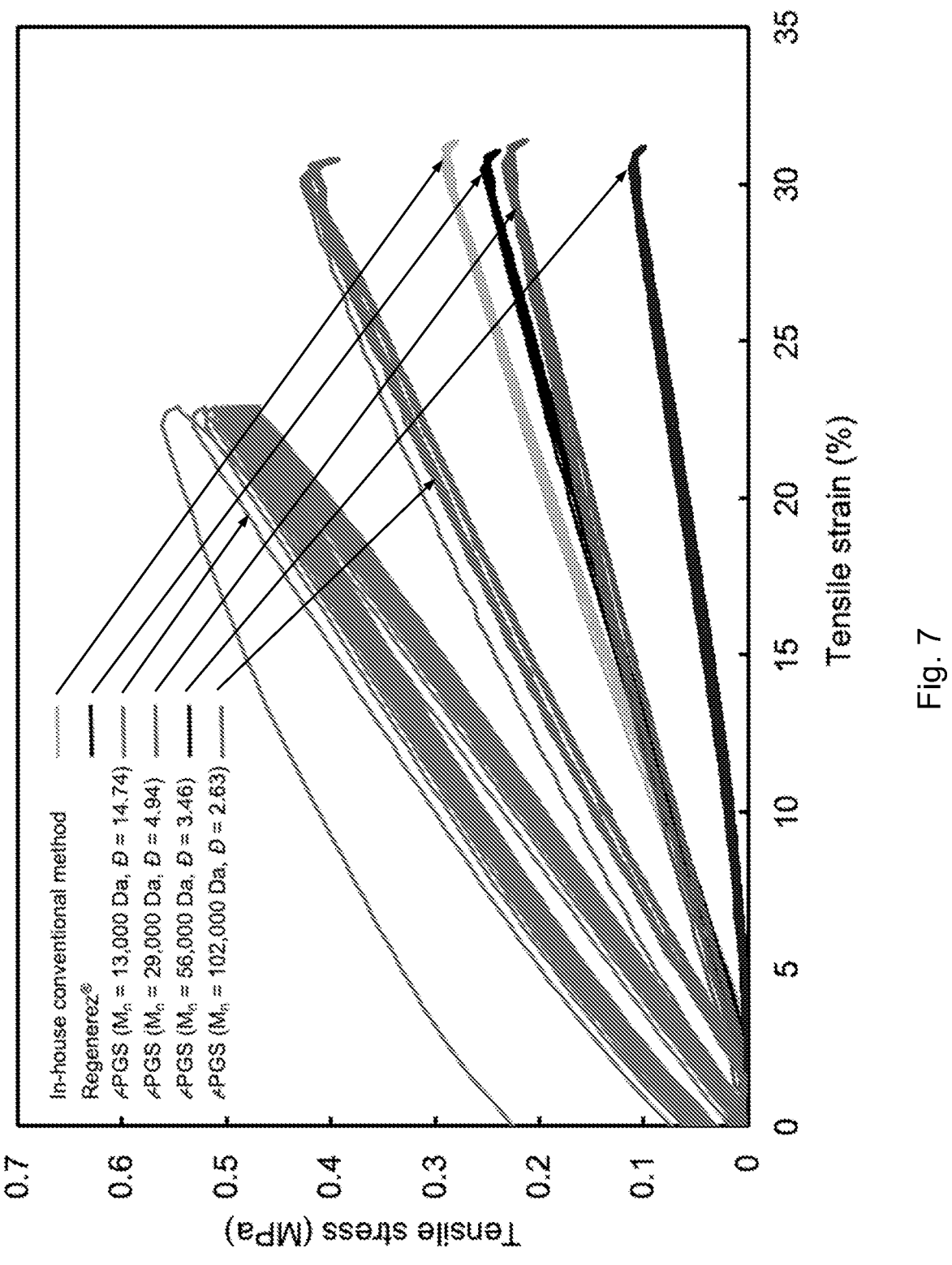
FIG. 7 illustrates cyclic tensile tests at 30% strain for 500 cycles for crosslinked PGS elastomers made by SC-CO$_2$ and conventional melt polycondensation (n=3).
Figure 8A:
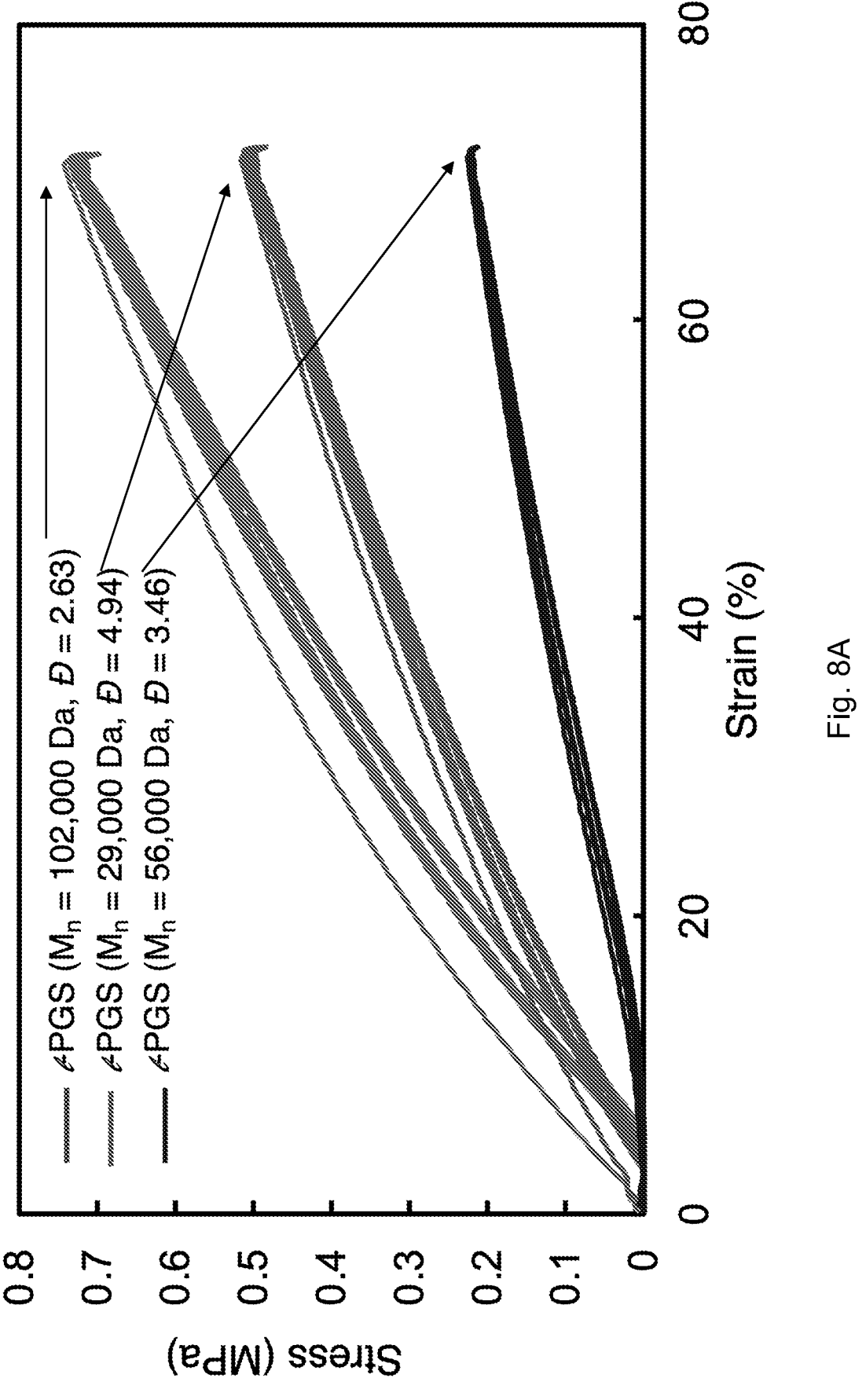
FIGS. 8A-8D illustrate comparisons of mechanical properties of crosslinked PGS elastomers made by SC-CO$_2$ and conventional melt polycondensation. (8A), Cyclic tensile tests at 70% strain for 500 cycles (n=3). (8B), Strain at fracture (n=4). (8C), Ultimate tensile stress (UTS, MPa; n=4). (8D), Young's modulus (E, MPa; n=4). Data represent mean±SD. One-way ANOVA was performed with Tukey's pairwise comparison tests. Different letters denote a significant difference (p<0.05).

Mechanical properties of the crosslinked ℓ PGS elastomers. Critical to the performance of an elastomer is plastic deformation in load-unload cycles. ℓ PGS and conventional PGS controls were cured under identical conditions: 150° C., 4 Pa (>99.999% vacuum), and 20 h. Cyclic tensile tests of the crosslinked ℓ PGS and controls were conducted at 30% and 70% strains respectively for 500 cycles under identical tensile elongation (FIGS. 7-8A). All the samples exhibited elastic behavior with narrow hysteresis loops, except for the crosslinked ℓ PGS ($M_n$=13,000 Da) with a high Đ of 14.7. Three types of elastomers made of ℓ PGS ($M_n$=29,000 Da, Đ=4.94; $M_n$=56,000 Da, Đ=3.46; $M_n$=102,000 Da, Đ=2.63) could sustain 500 cycles of 70% tensile strain (FIG. 8A). Samples of the two conventional PGS controls and one ℓ PGS ($M_n$=13,000 Da, Đ=14.74) snapped within the first 100 cycles when subjected to 70% strain. Therefore, a larger and uniform ℓ PGS contributed to a more resilient elastomer, likely because of the ordered network of crosslinking. Loading stress could be dissipated efficiently by the organized polymeric structure, enabling the elastomers to last for an extended period of cyclic stress with low plastic deformation.

Figure 8B:
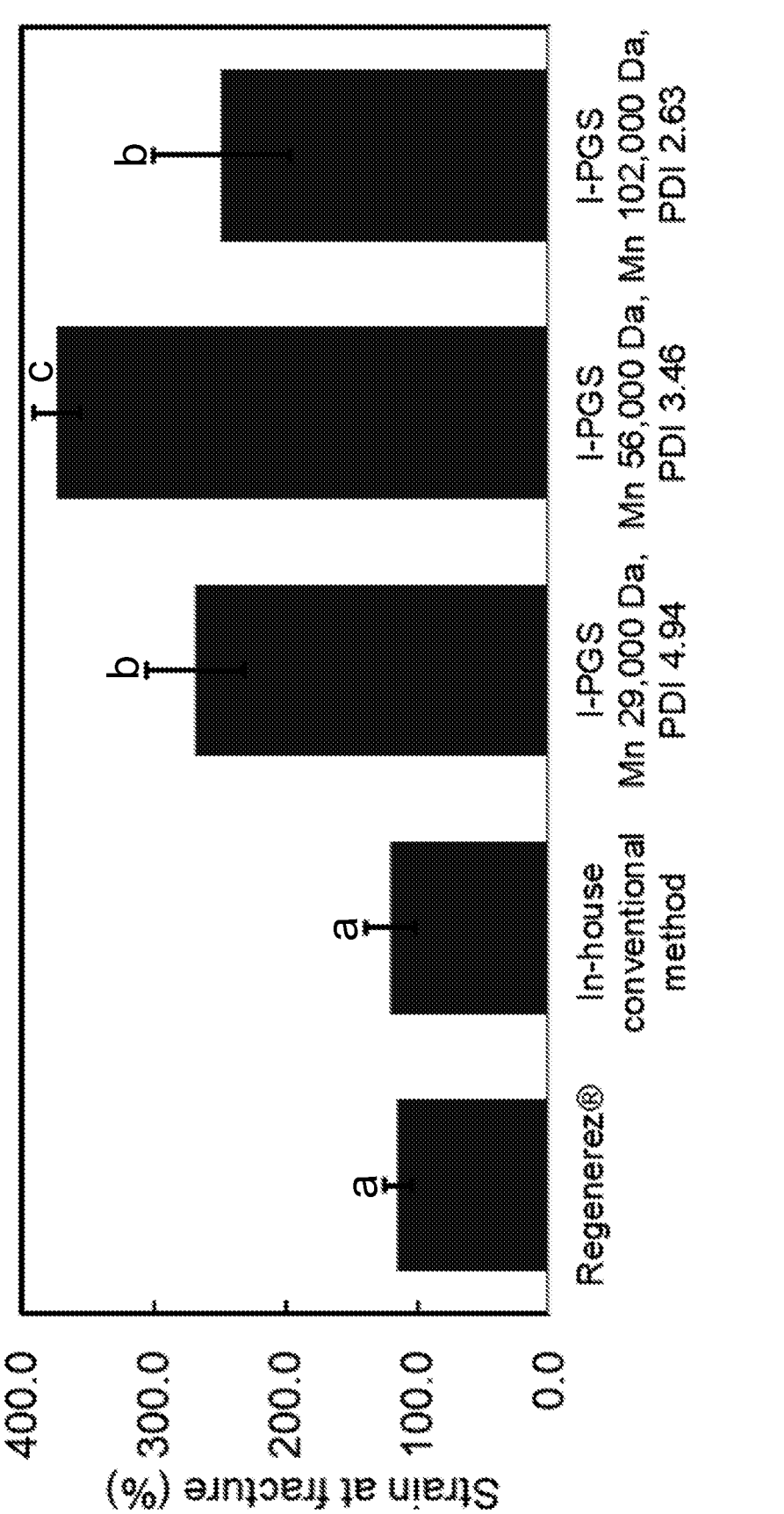
Figure 8C:
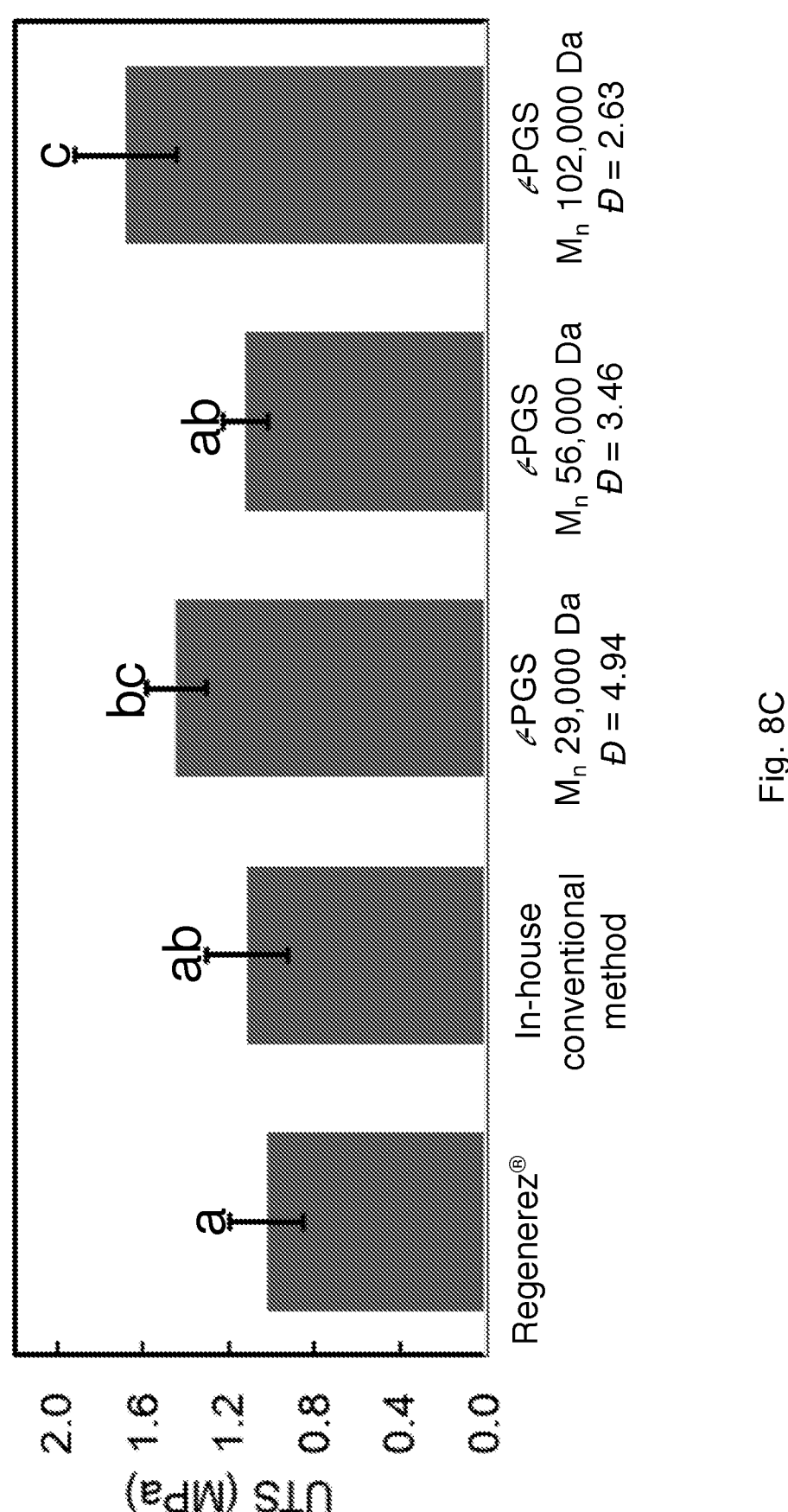
Figure 8D:
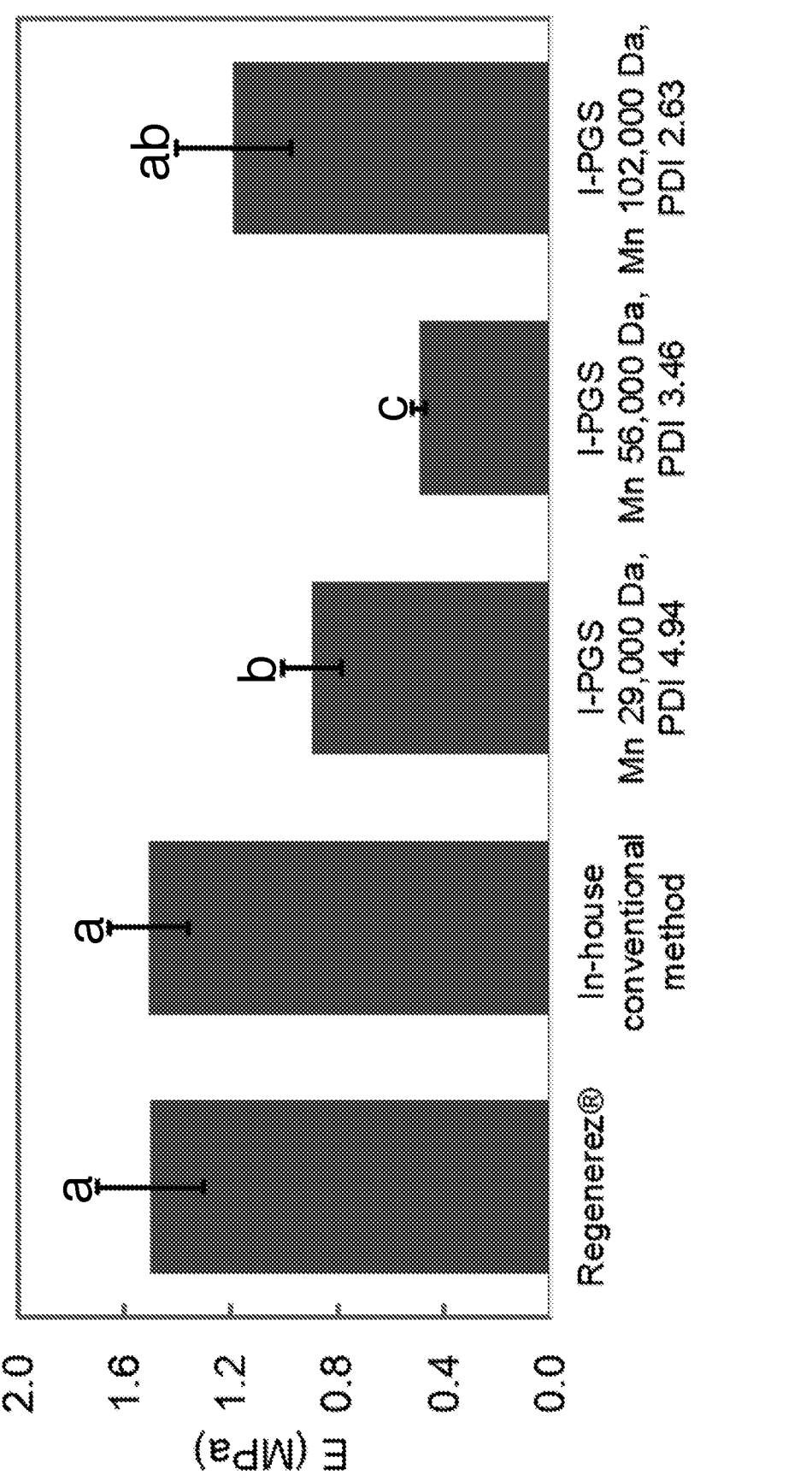

Mechanical properties are important for the function of an elastomer. Depending on synthesis parameters, the crosslinked ℓ PGS exhibited 2 to 3 times higher elongation with improved ultimate tensile stress than the controls made from conventional PGS (FIGS. 8B-8C). The most ductile crosslinked ℓ PGS ($M_n$=56,000 Da, Đ=3.46) broke at 374% strain, ~3 times as high as those made of conventional PGS (FIG. 8B). The ultimate tensile stress of the strongest crosslinked ℓ PGS ($M_n$=102,000 Da, Đ=2.63) was 1.69 MPa, ~1.5 times as higher as those of conventional PGS (FIG. 8C). Young's moduli of the crosslinked ℓ PGS were reduced by 20 to 70%, compared to the controls (FIG. 8D). Either type of the crosslinked ℓ PGS displayed the typical nonlinear stress-strain curve of elastomers and resembled those of soft tissues, such as blood vessels and myocardia. Raising CALB content from 10 to 40 wt. % decreased the Đ value of ℓ PGS from 14.74 to 3.46 (Table 2) and improved the strain at break from 127.9% to 374% (Table 7). Descending order was observed in ultimate tensile strength and Young's moduli among the ℓ PGS elastomers with increasing $M_n$ and reducing Đ, alongside the increasing CALB content for polycondensation in SC-$CO_2$ (Tables 7-8). This demonstrates the profound impact of increasing size, uniformity, and potentially linearity of the polymers on mechanical properties of the crosslinked products.

TABLE 7

Strain at fracture, ultimate tensile strength (UTS), and Young's modulus of the PGS controls and ℓ PGS with high molecular weights.

| Sample | Strain at fracture (%) | UTS (MPa) | Young's modulus (MPa) |
|---|---|---|---|
| Regenerez ® | 114.95 ± 10.57[a] | 1.02 ± 0.17[a] | 1.51 ± 0.20[a] |
| In-house conventional method | 120.87 ± 18.93[a] | 1.11 ± 0.19[ab] | 1.51 ± 0.15[a] |
| ℓ PGS[1] ($M_n$: 13,000 Da, Đ: 14.74) | 127.91 ± 26.15[a] | 2.15 ± 0.05[c] | 15.76 ± 3.26[b] |
| ℓ PGS[2] ($M_n$: 29,000 Da, Đ: 4.94) | 269.20 ± 37.02[b] | 1.45 ± 0.14[bd] | 0.90 ± 0.11[c] |
| ℓ PGS[3] ($M_n$: 56,000 Da, Đ: 3.46) | 374.03 ± 17.89[c] | 1.12 ± 0.11[ab] | 0.49 ± 0.03[d] |
| ℓ PGS[4] ($M_n$: 102,000 Da, Đ: 2.63) | 248.90 ± 51.83[b] | 1.69 ± 0.24[d] | 1.19 ± 0.21[ac] |

[1] ℓ PGS was synthesized in SC—$CO_2$ at 35 MPa and 60° C. with 10 wt. % CALB for 12 h.
[2] ℓ PGS was synthesized in SC—$CO_2$ at 35 MPa and 60° C. with 20 wt. % CALB for 12 h.
[3] ℓ PGS was synthesized in SC—$CO_2$ at 35 MPa and 60° C. with 40 wt. % CALB for 12 h.
[4] ℓ PGS was synthesized in SC—$CO_2$ at 35 MPa and 60° C. with 10 wt. % CALB for 18 h.
[5] Data represent mean ± SD.
[6] One-way ANOVA was performed with Tukey's pairwise comparison tests. Different letters denote a significant difference within a column ($p < 0.05$).

TABLE 8

Experimental data of strain at fracture, ultimate tensile strength (UTS), and Young's modulus for the PGS controls and ℓ PGS with high molecular weights.

| | Regenerez ® | In-house conventional method | ℓ PGS ($M_n$: 13,000 Da, Đ: 14.74) | ℓ PGS ($M_n$: 29,000 Da, Đ: 4.94) | ℓ PGS ($M_n$: 56,000 Da, Đ: 3.46) | ℓ PGS ($M_n$: 102,000 Da, Đ: 2.63) |
|---|---|---|---|---|---|---|
| Strain at fracture (%) | 124.25 | 100.55 | 99.88 | 235.64 | 382.26 | 173.52 |
| | 102.34 | 111.6 | 131.98 | 258.68 | 347.22 | 264.44 |
| | 110.12 | 127.36 | 161.91 | 260.41 | 382.69 | 291.97 |
| | 123.09 | 143.97 | 118.16 | 322.08 | 383.95 | 265.67 |
| Mean | 114.95 | 120.87 | 127.91 | 269.20 | 374.03 | 248.90 |
| SD | 10.57 | 18.93 | 26.15 | 37.02 | 17.89 | 51.83 |
| UTS (MPa) | 1.17 | 0.84 | 2.22 | 1.38 | 1.22 | 1.40 |
| | 0.81 | 1.14 | 2.16 | 1.30 | 0.97 | 1.69 |
| | 0.96 | 1.19 | 2.12 | 1.48 | 1.14 | 1.98 |
| | 1.15 | 1.28 | 2.11 | 1.62 | 1.16 | 1.67 |

TABLE 8-continued

| | | | | | |
|---|---|---|---|---|---|
| | | | Experimental data of strain at fracture, ultimate tensile strength (UTS), and Young's modulus for the PGS controls and ℓPGS with high molecular weights. | | |

| | Regenerez ® | In-house conventional method | ℓPGS ($M_n$: 13,000 Da, Đ: 14.74) | ℓPGS ($M_n$: 29,000 Da, Đ: 4.94) | ℓPGS ($M_n$: 56,000 Da, Đ: 3.46) | ℓPGS ($M_n$: 102,000 Da, Đ: 2.63) |
|---|---|---|---|---|---|---|
| Mean | 1.02 | 1.11 | 2.15 | 1.45 | 1.12 | 1.69 |
| SD | 0.17 | 0.19 | 0.05 | 0.14 | 0.11 | 0.24 |
| Young's modulus (MPa) | 1.66 | 1.31 | 19.36 | 1.04 | 0.53 | 1.50 |
| | 1.22 | 1.67 | 17.46 | 0.84 | 0.47 | 1.03 |
| | 1.52 | 1.52 | 12.13 | 0.92 | 0.48 | 1.08 |
| | 1.62 | 1.53 | 14.09 | 0.78 | 0.49 | 1.15 |
| Mean | 1.51 | 1.51 | 15.76 | 0.90 | 0.49 | 1.19 |
| SD | 0.20 | 0.15 | 3.26 | 0.11 | 0.03 | 0.21 |

Figure 9D:
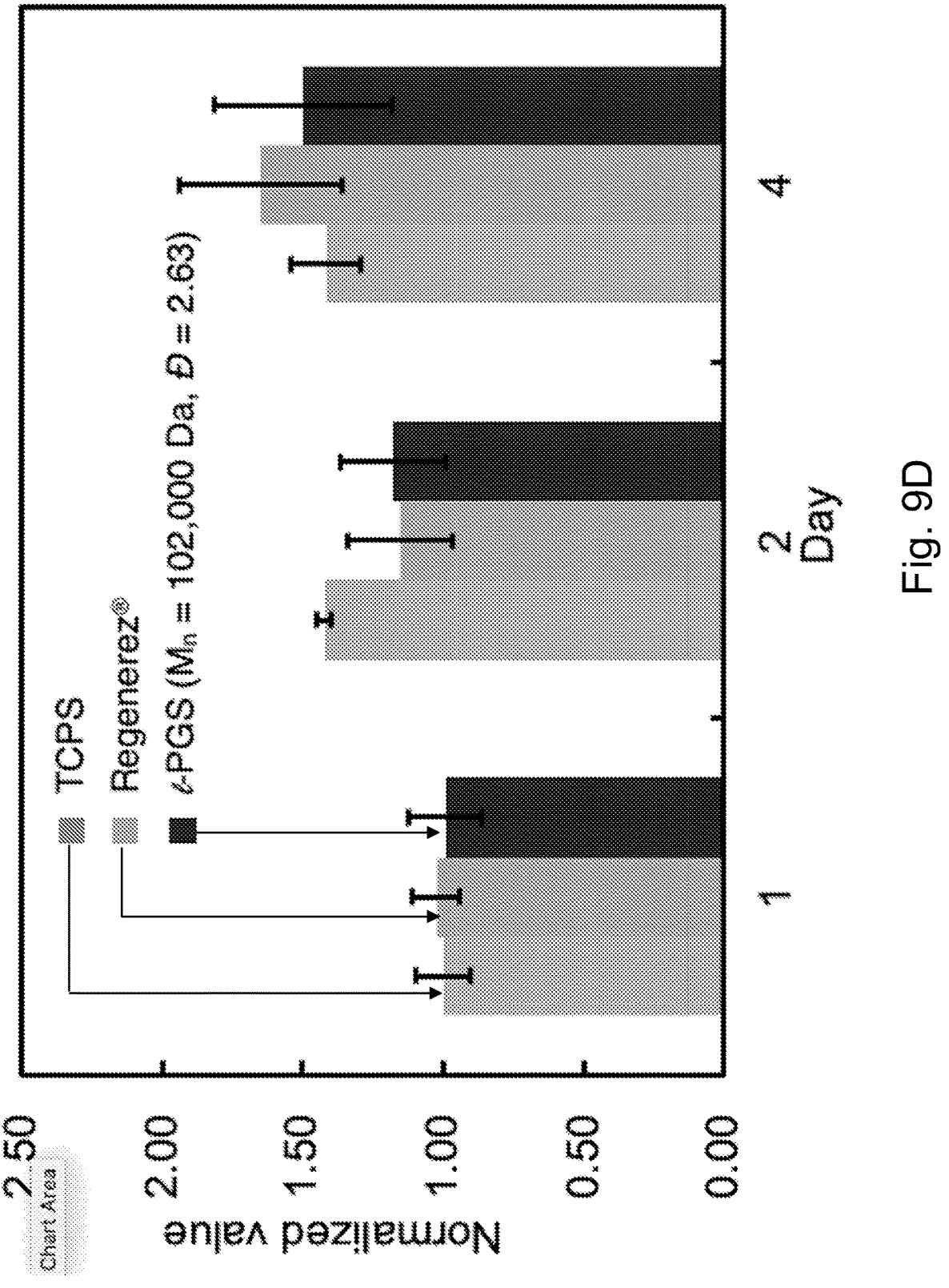
Figure 10A:
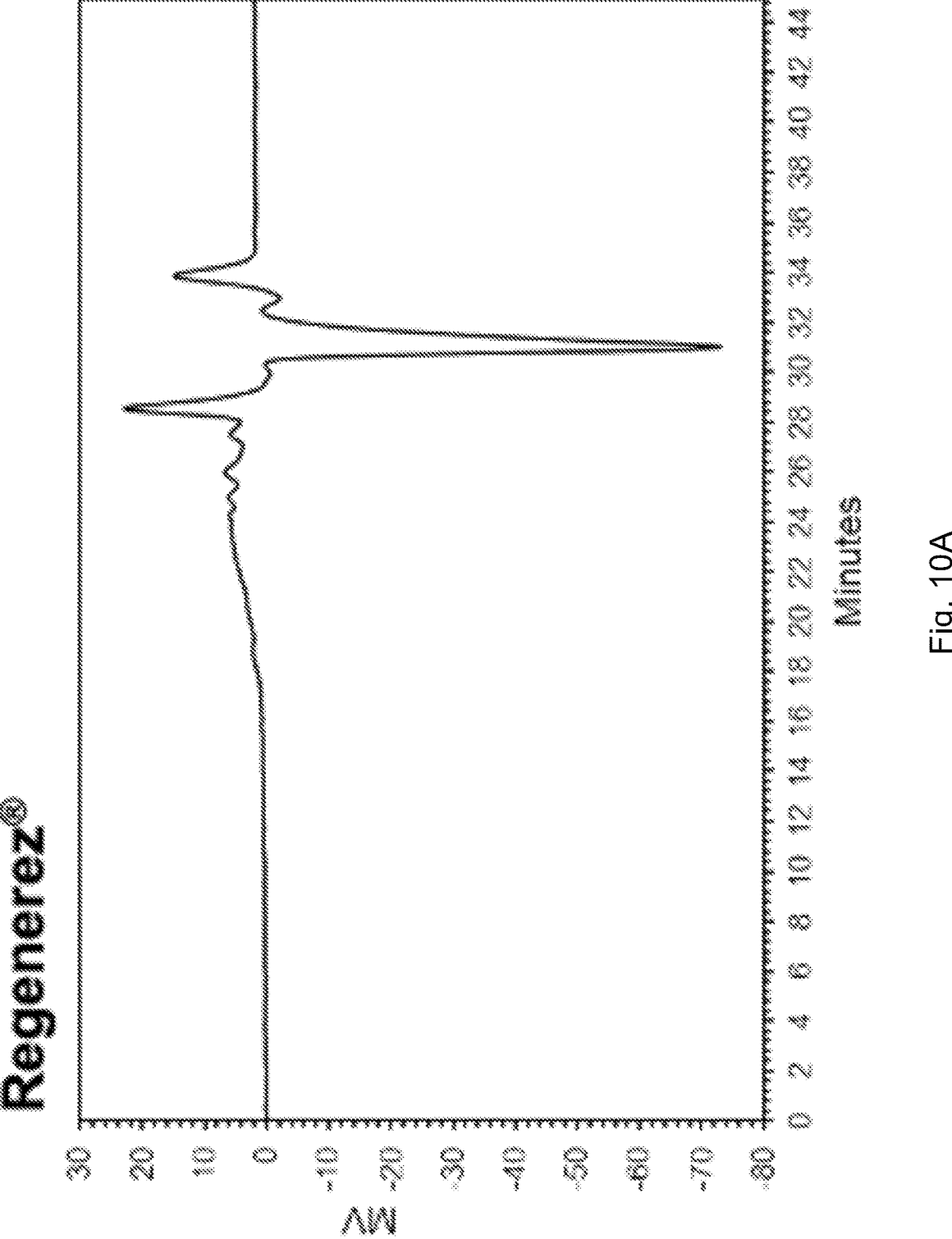
FIGS. 10A-10C illustrate molecular weight distributions of $\ell$ PGS using gel $\ell$ permeation chromatography (GPC).
Figure 10A:
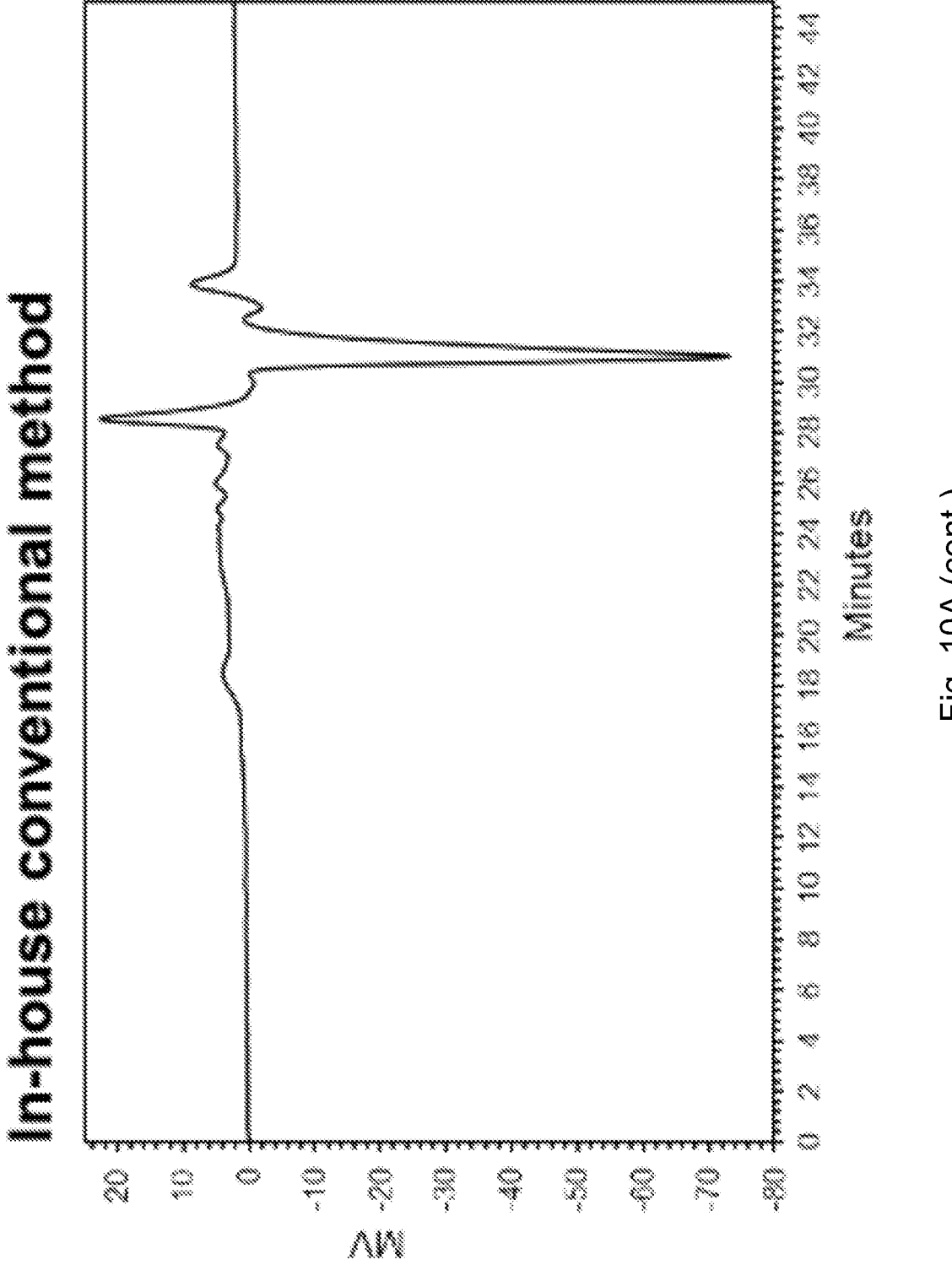
Figure 10A:
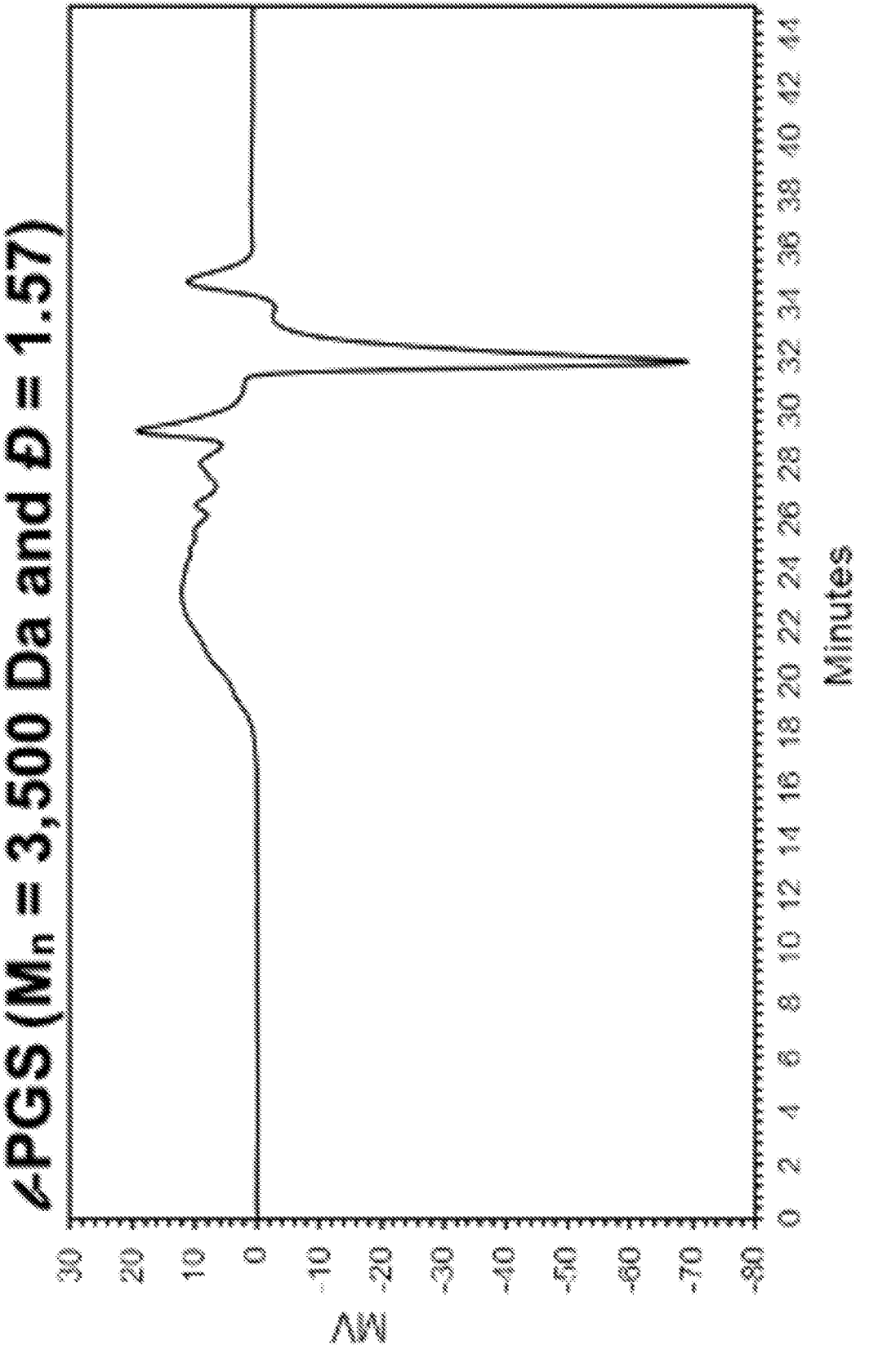
Figure 10A:
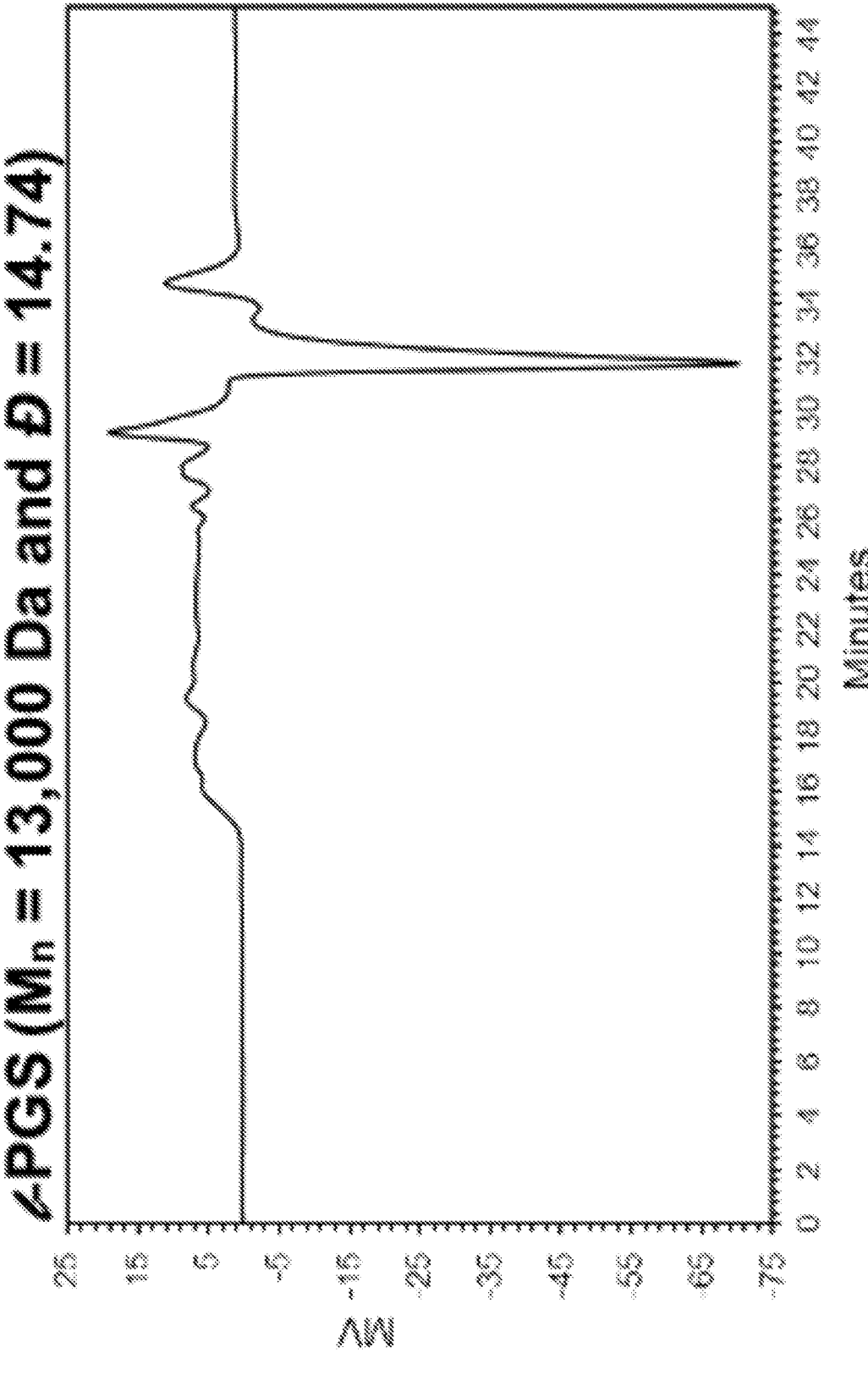
Figure 10A:
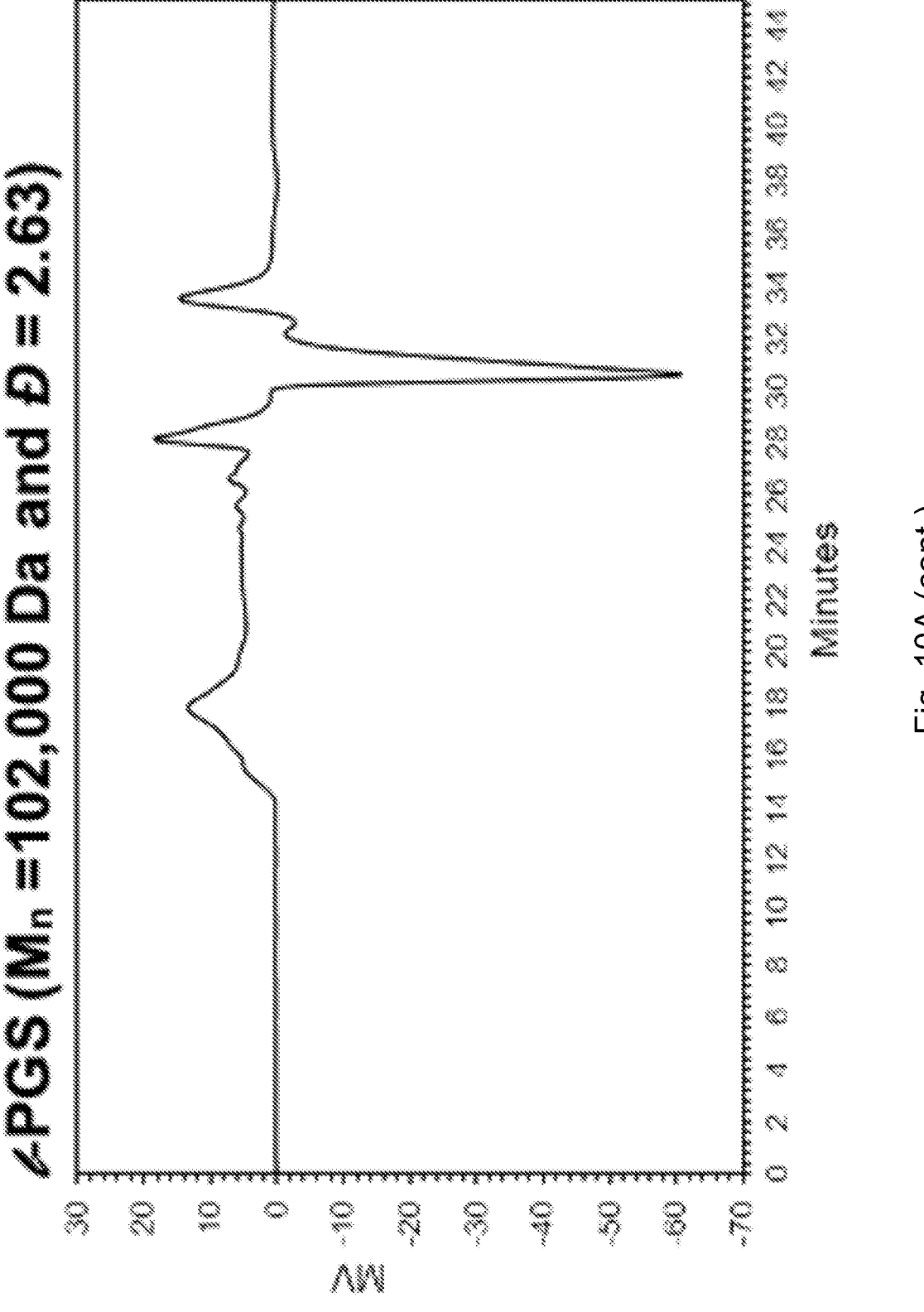
Figure 10A:
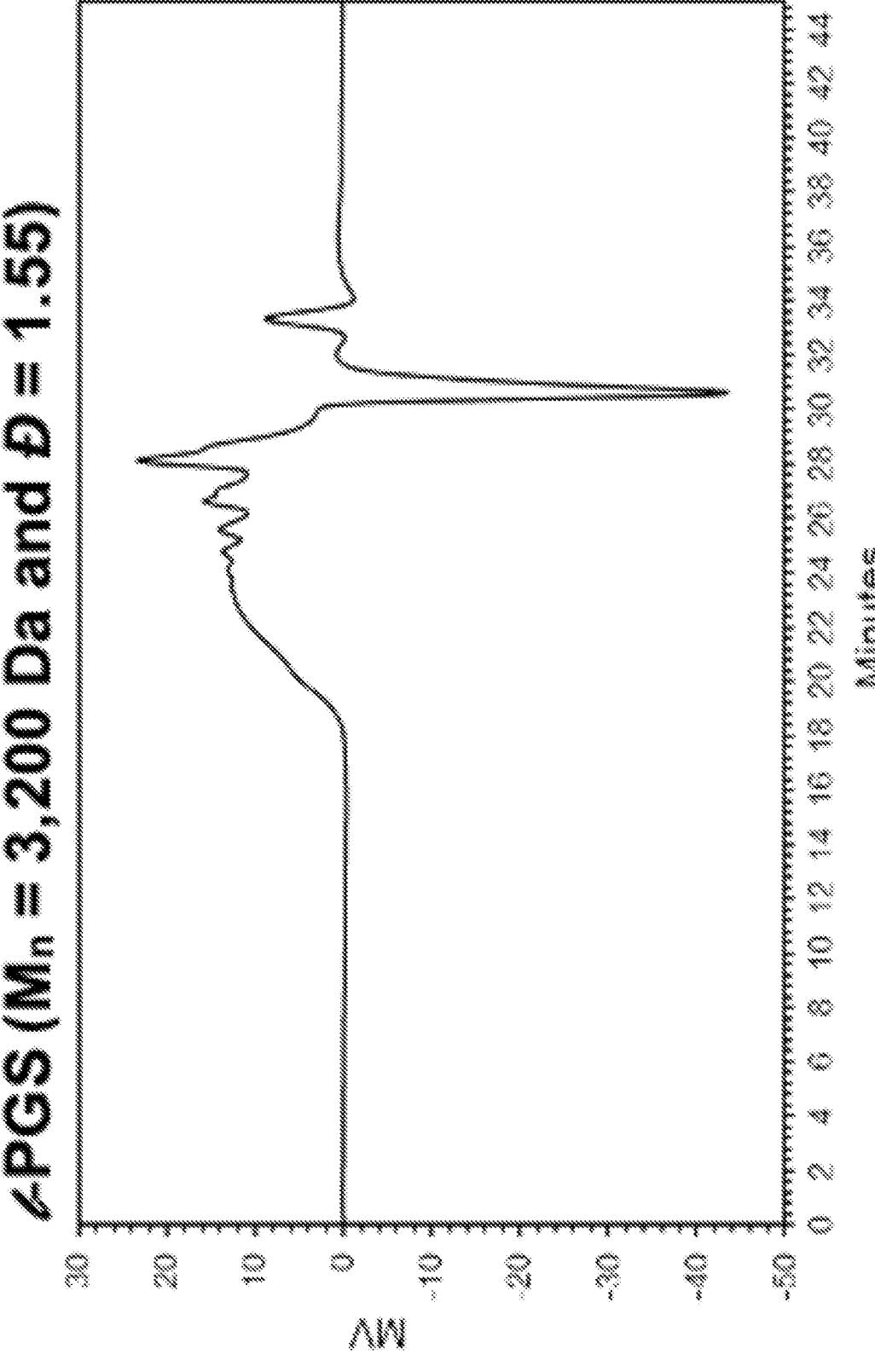
Figure 10A:
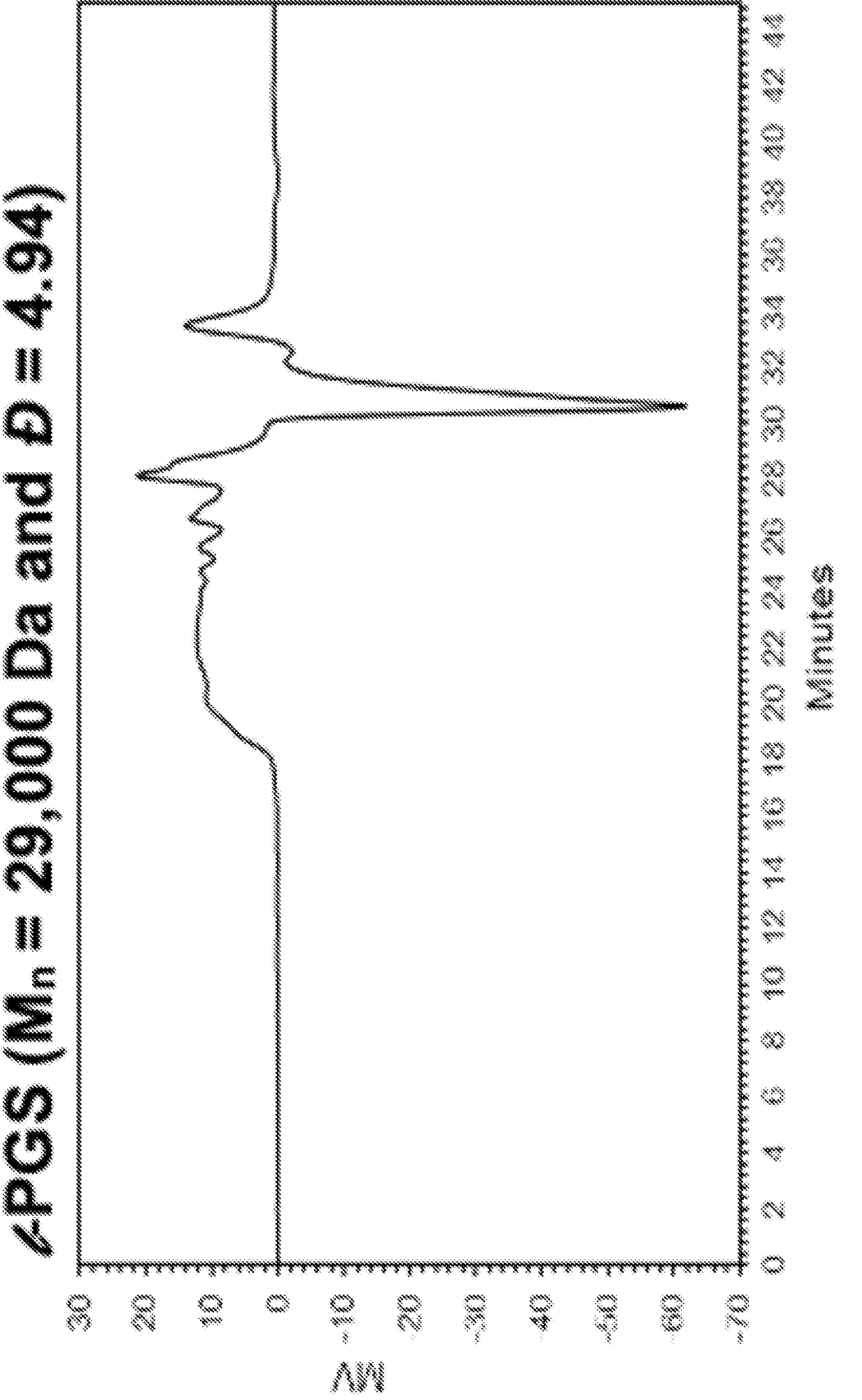
Figure 10A:
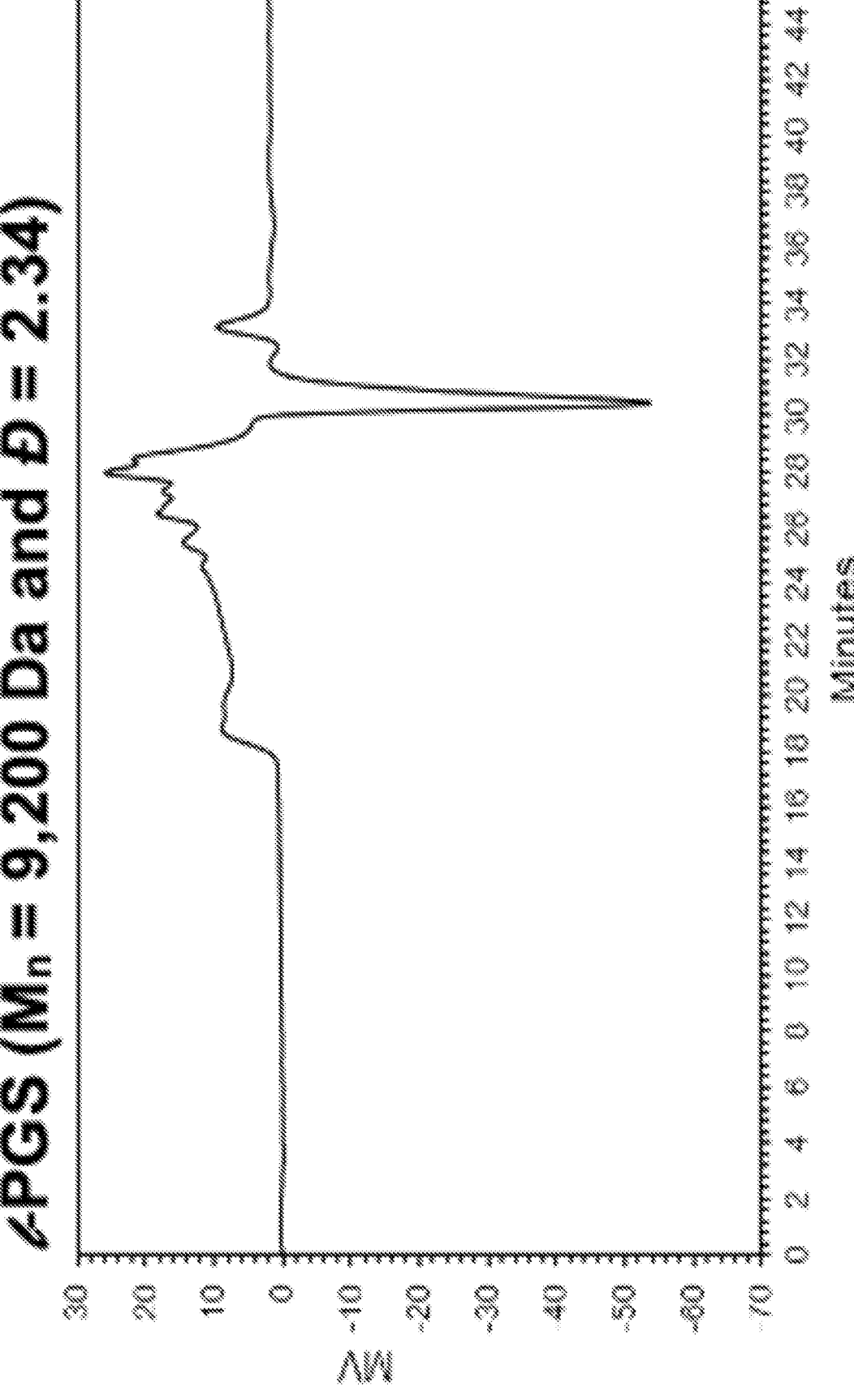
Figure 10B:
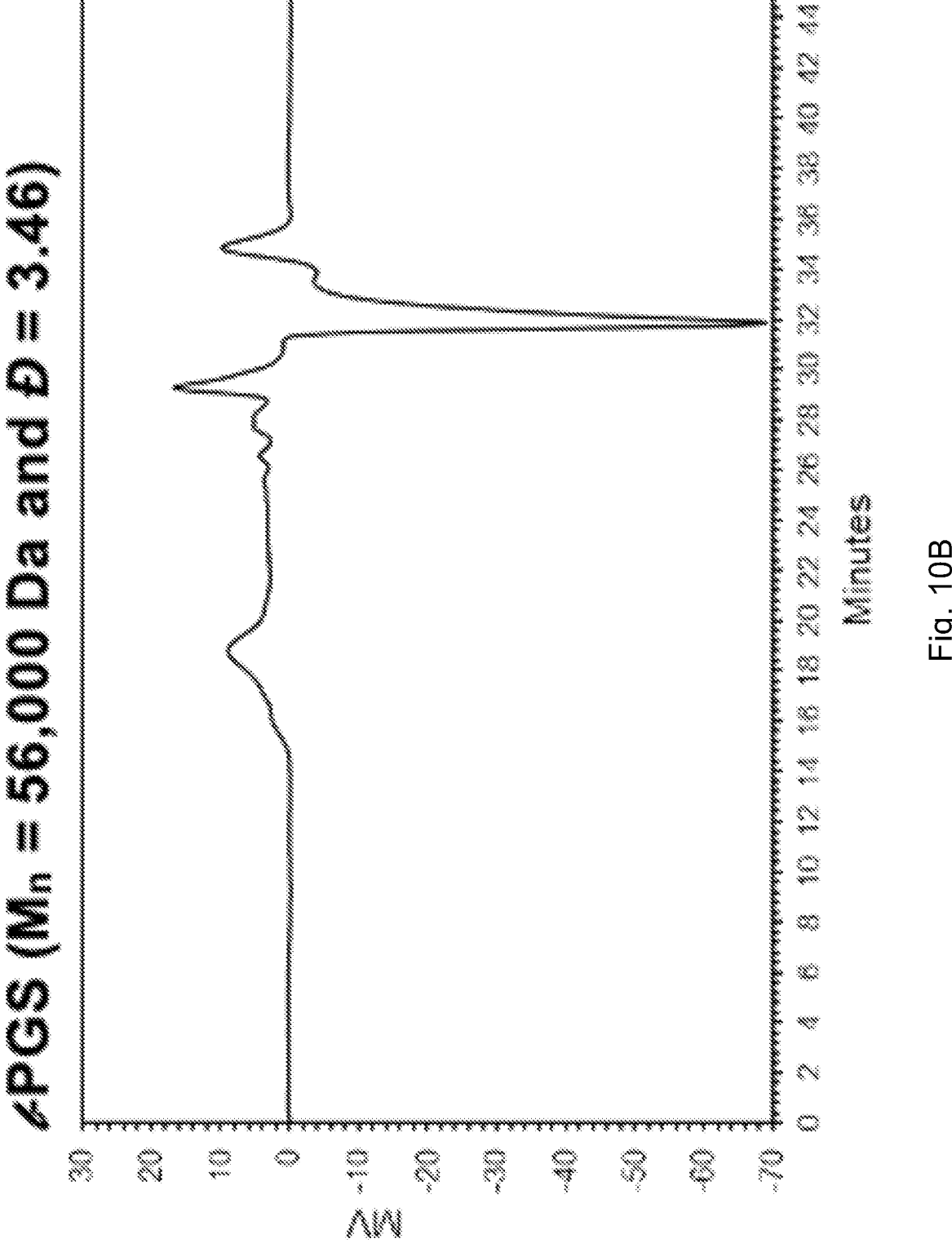
Figure 10B:
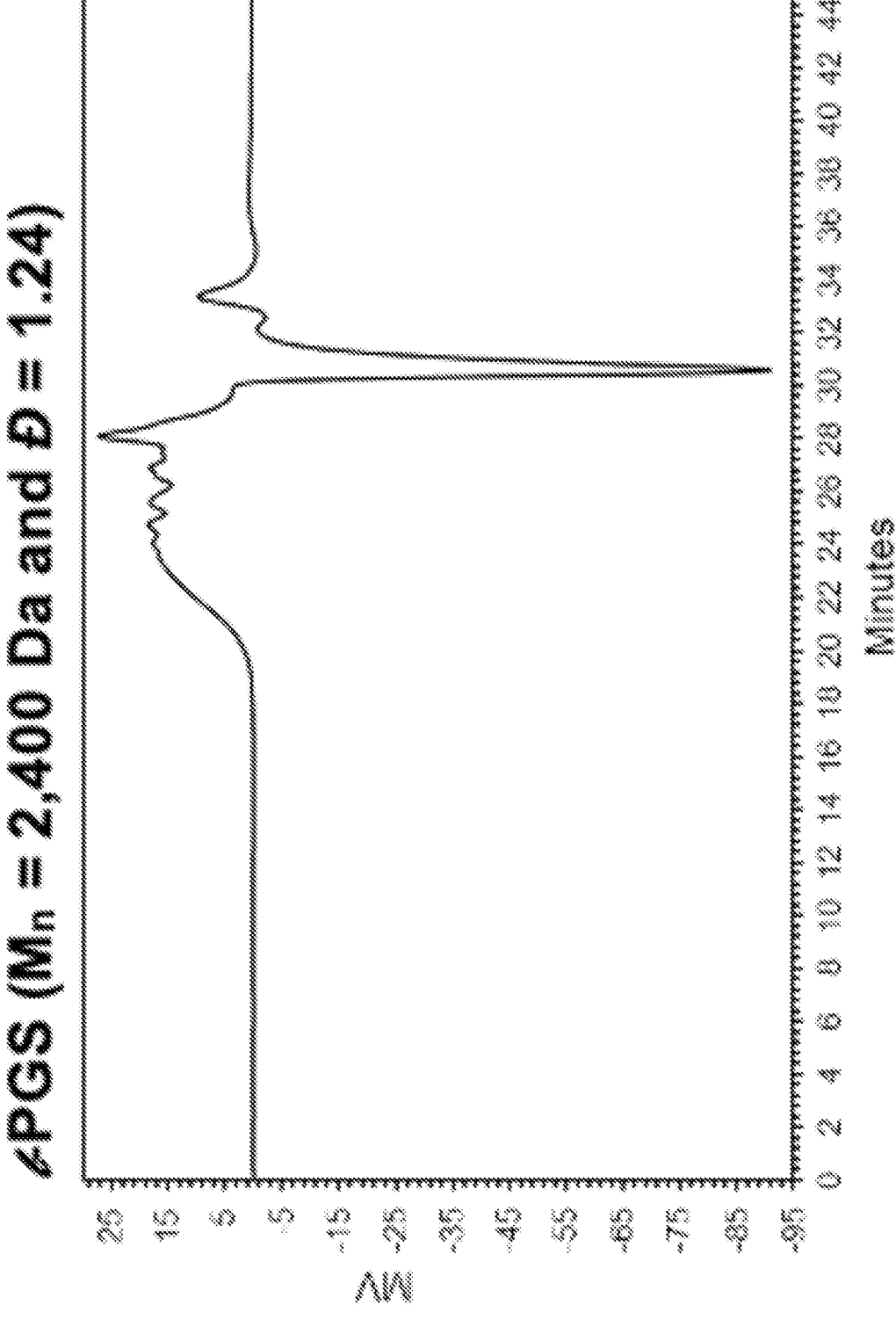
Figure 10B:
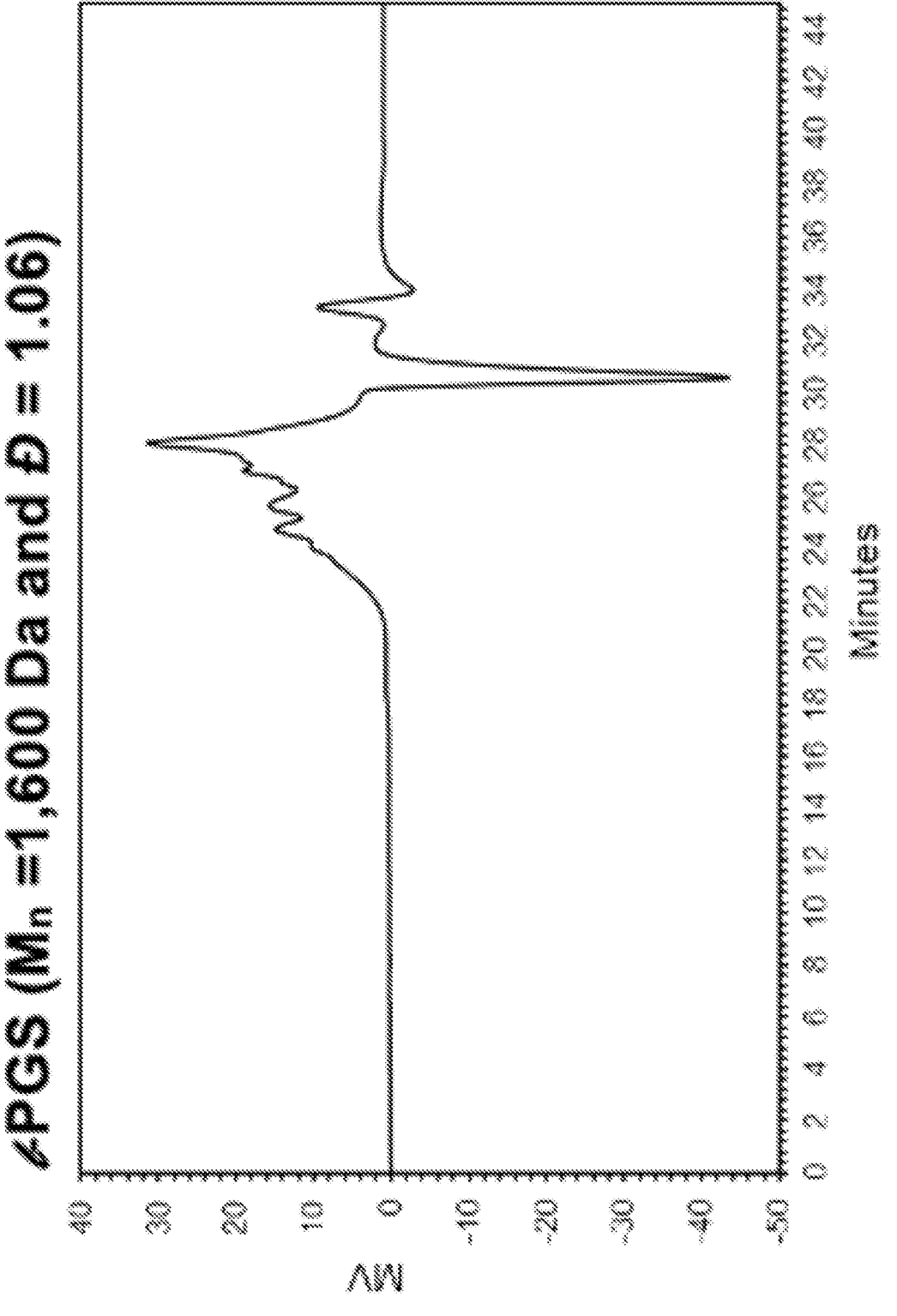
Figure 10B:
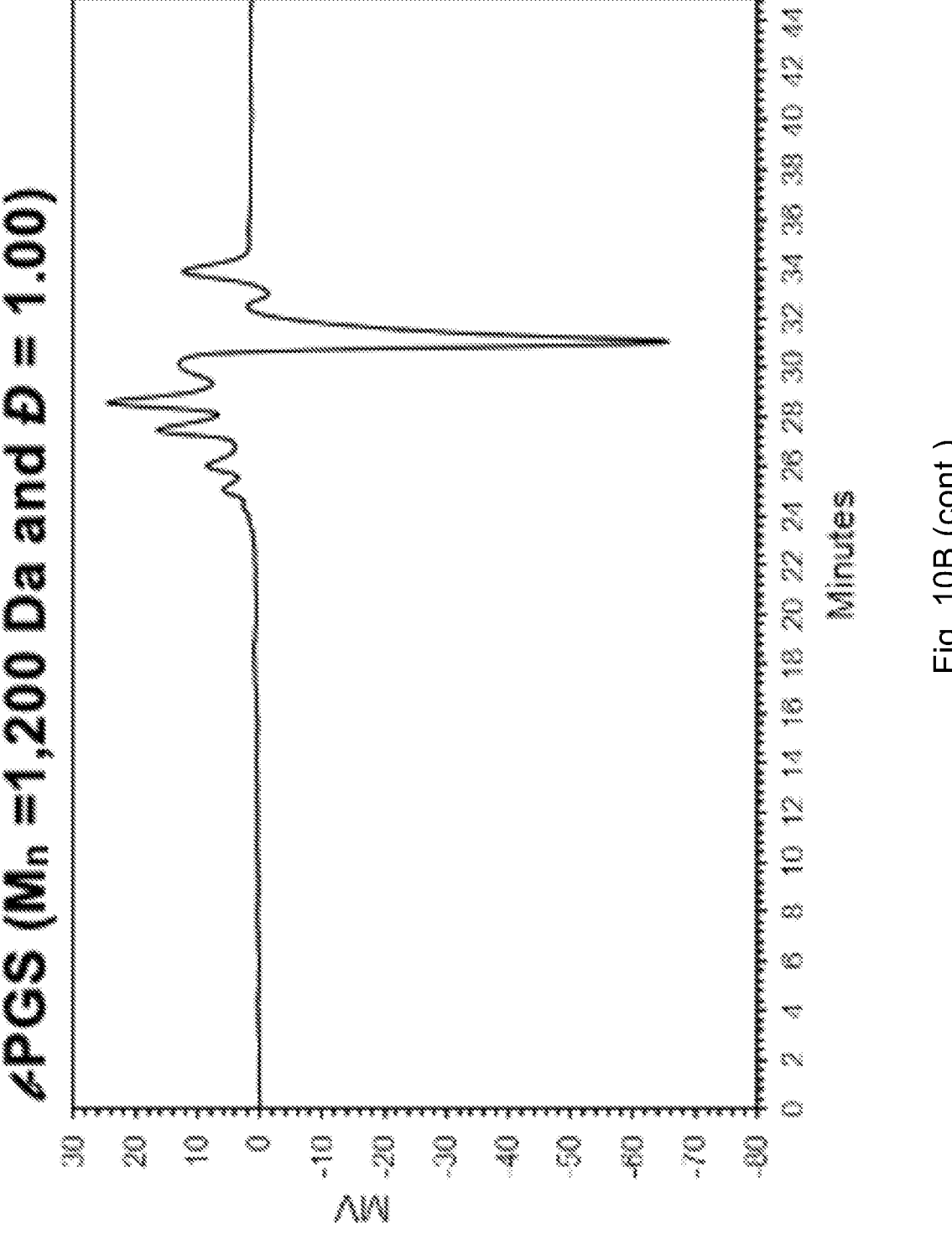
Figure 10B:
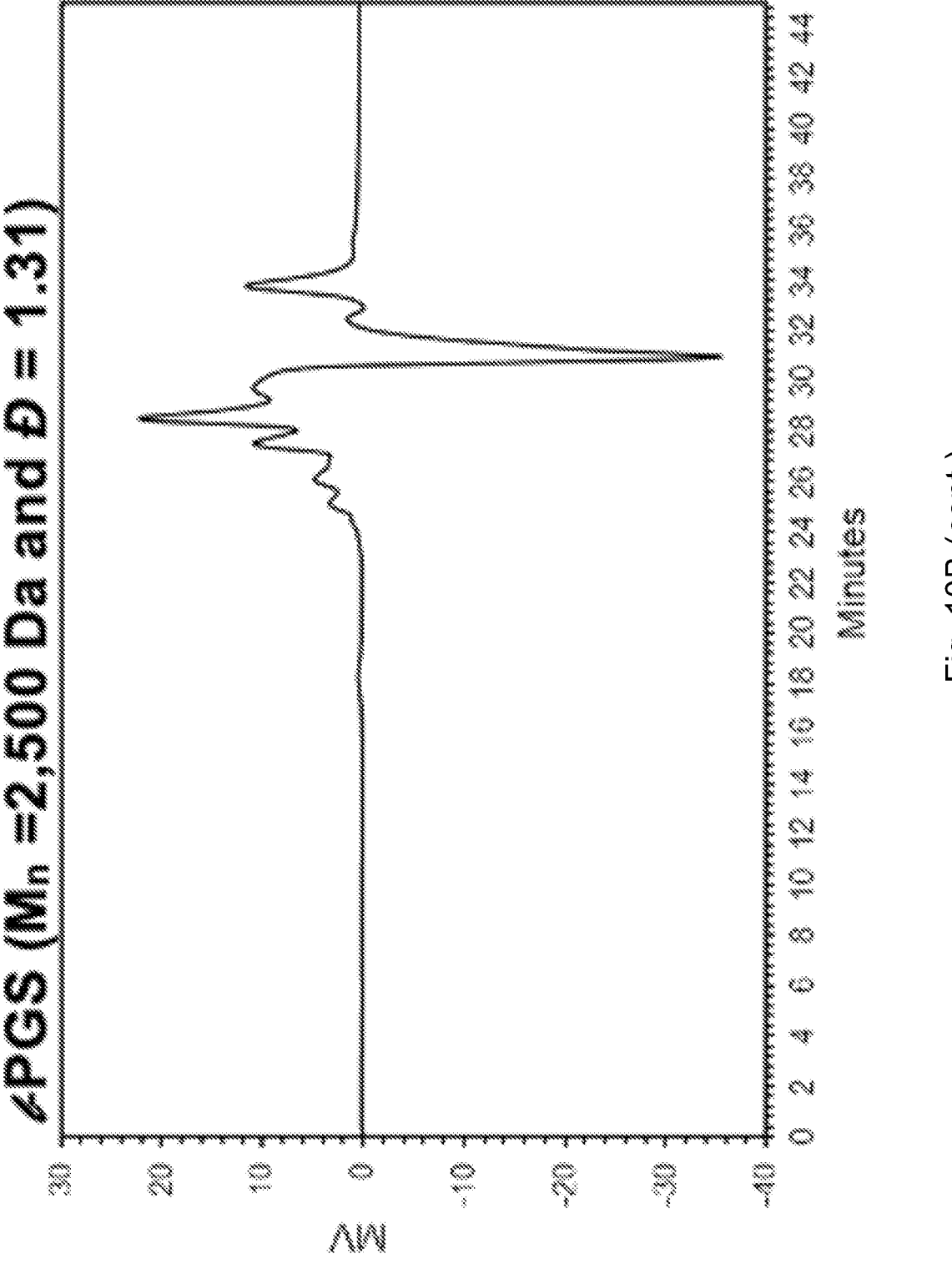
Figure 10B:
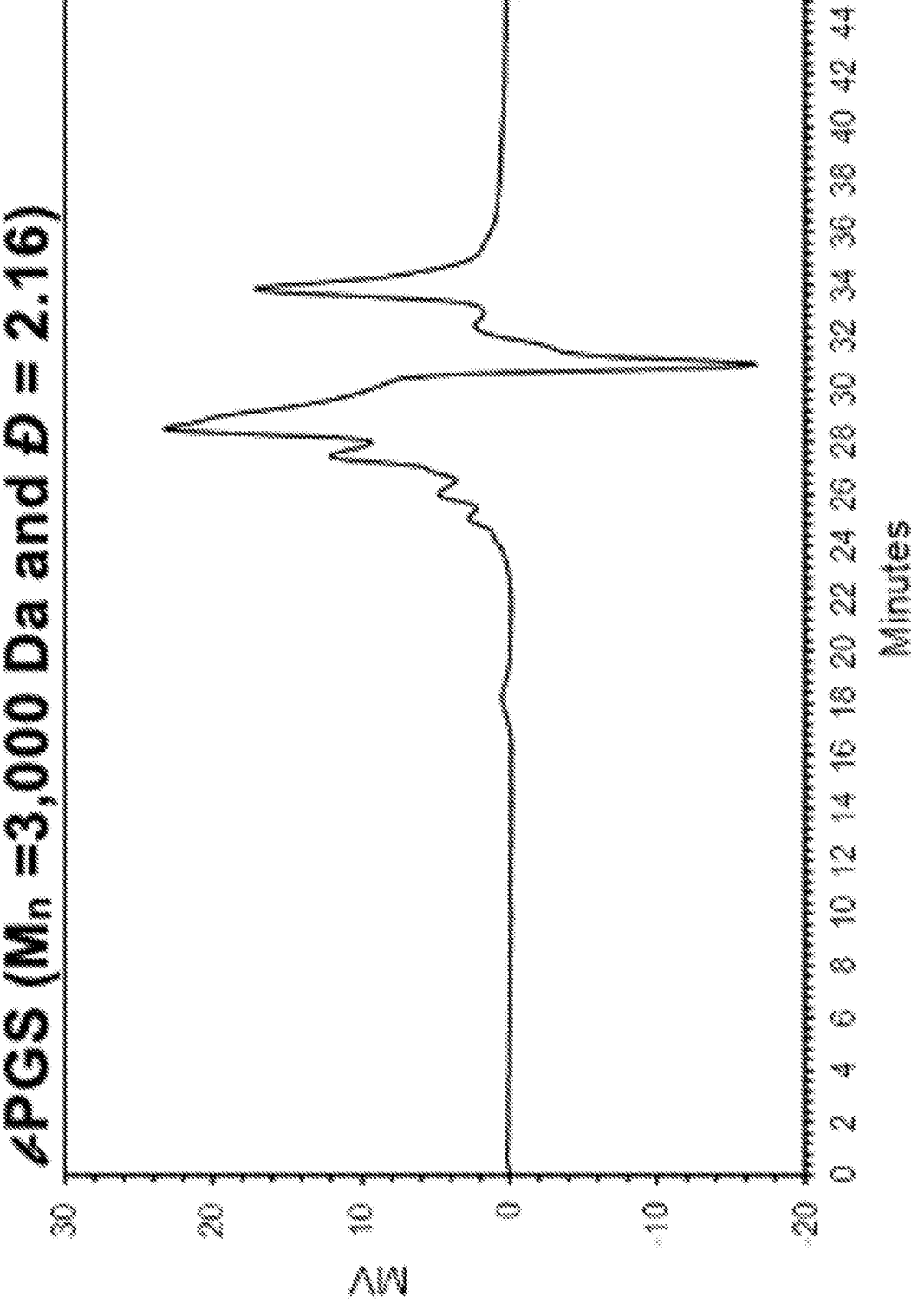
Figure 10B:
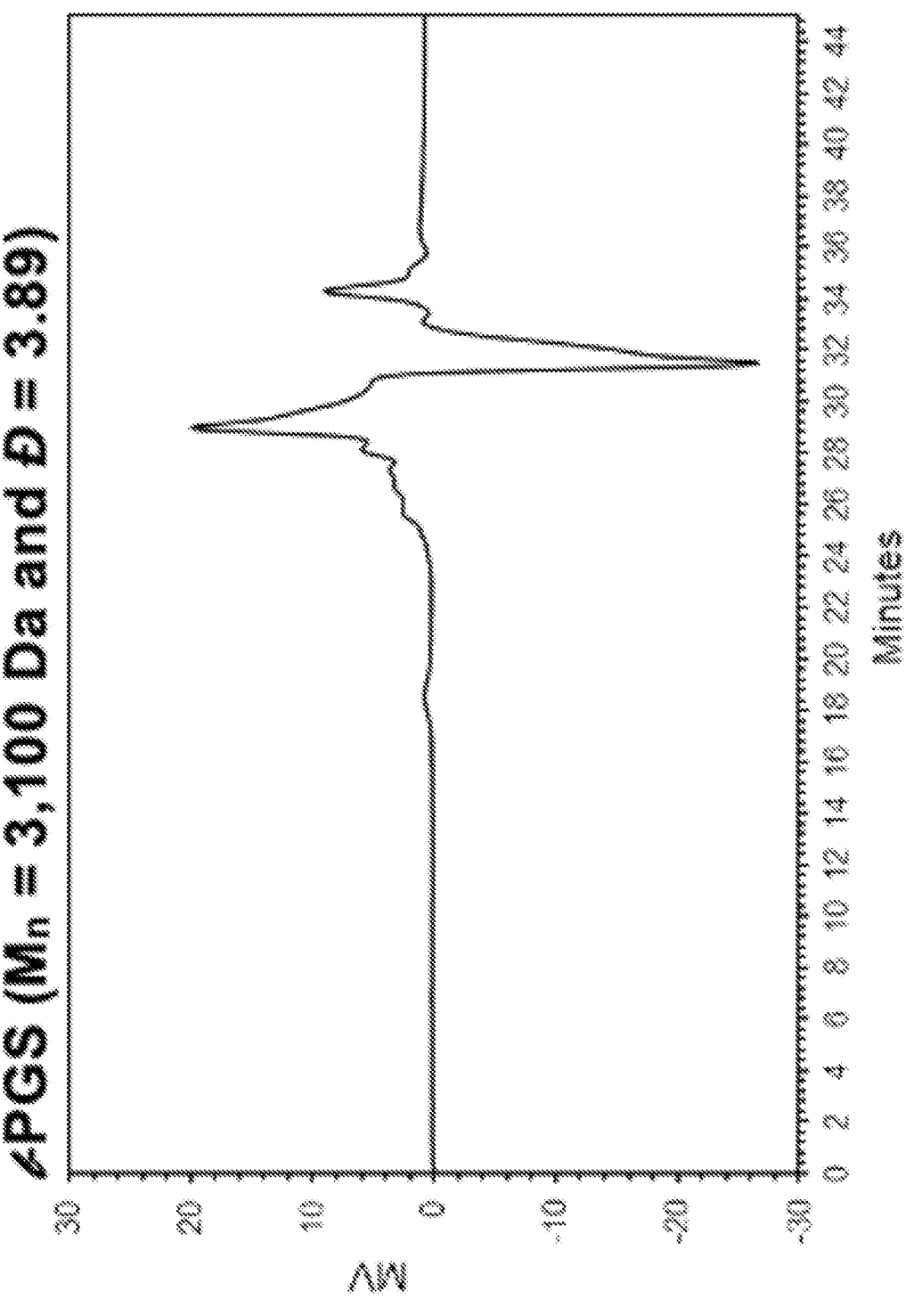
Figure 10B:
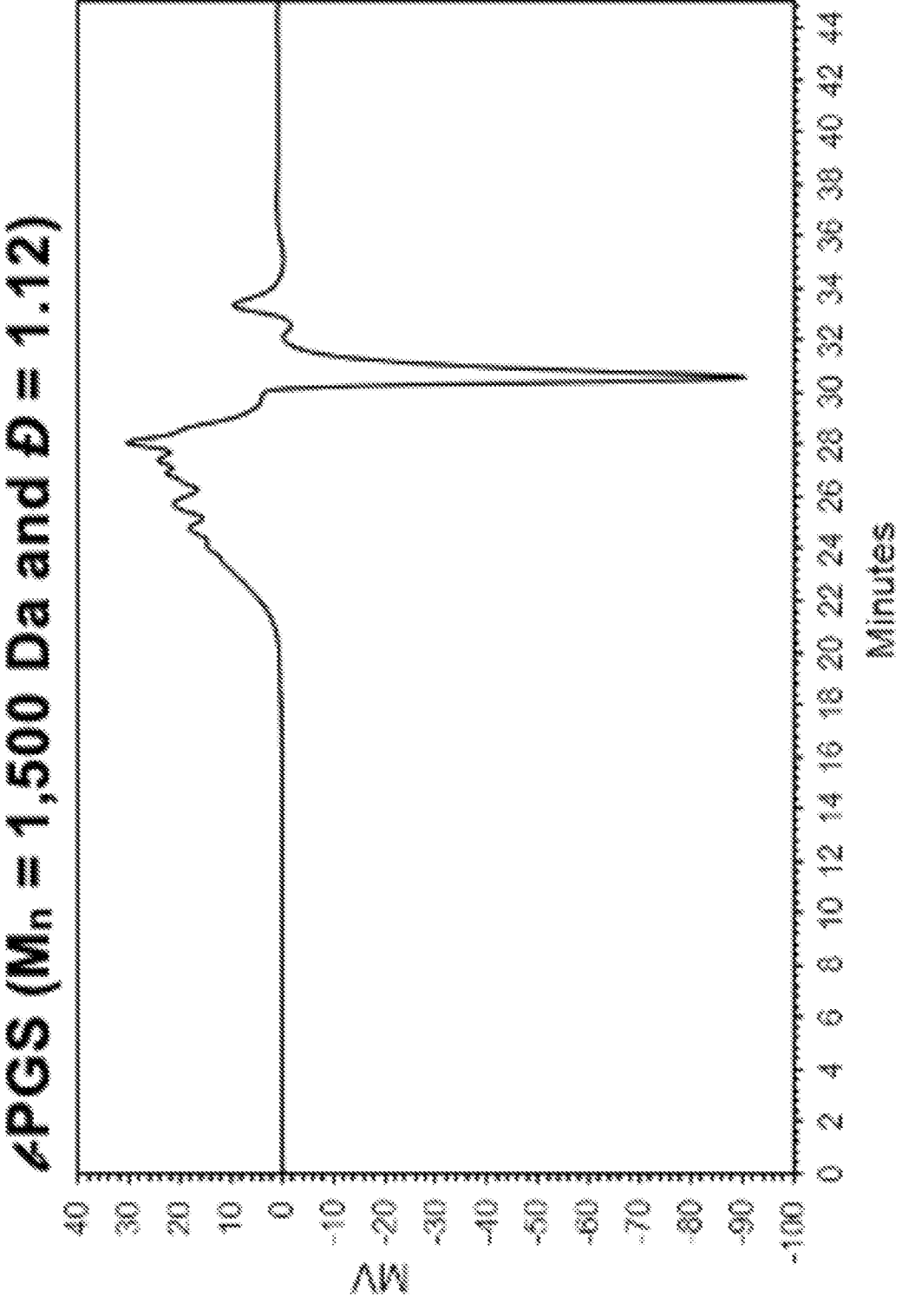
Figure 10C:
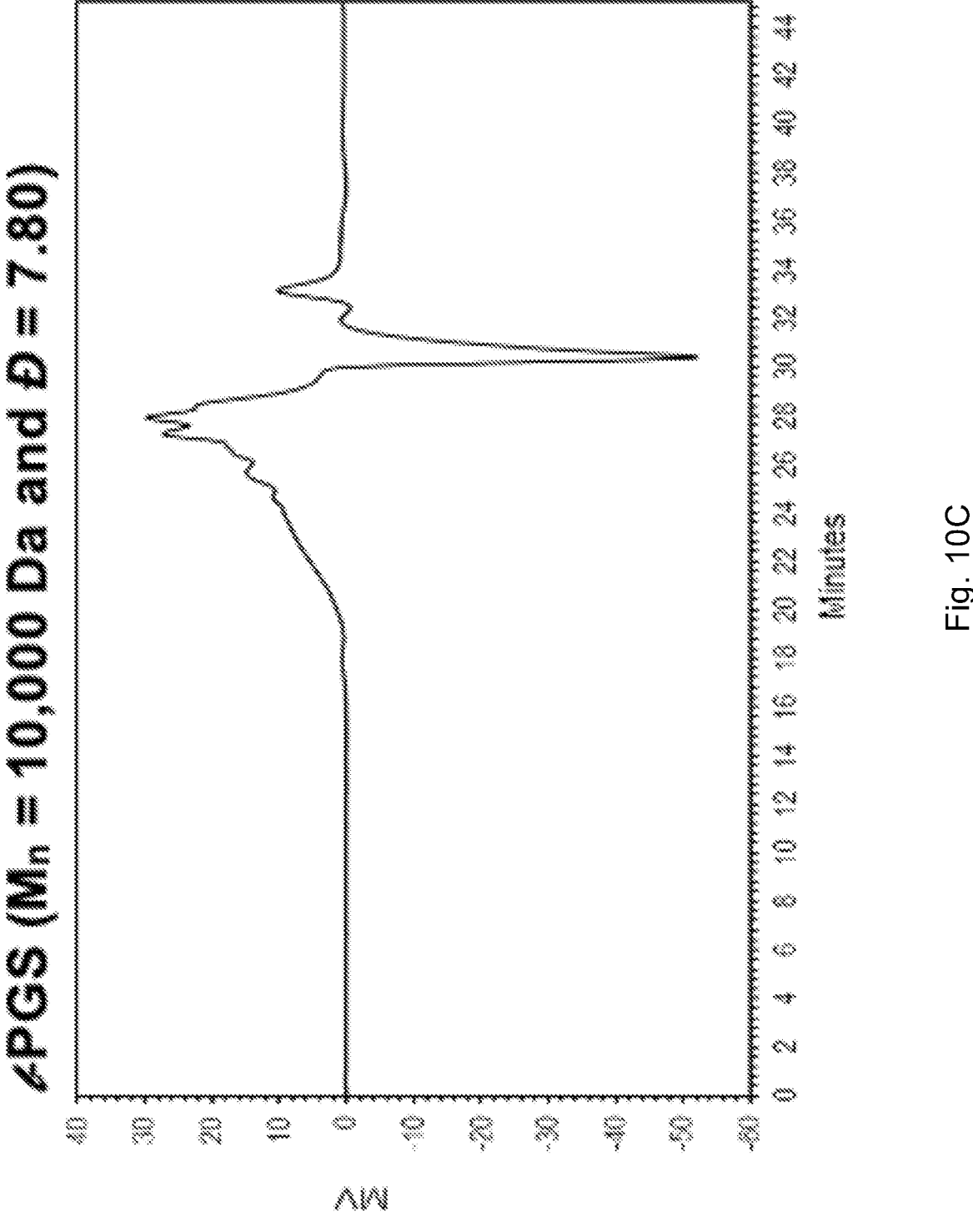
Figure 11:
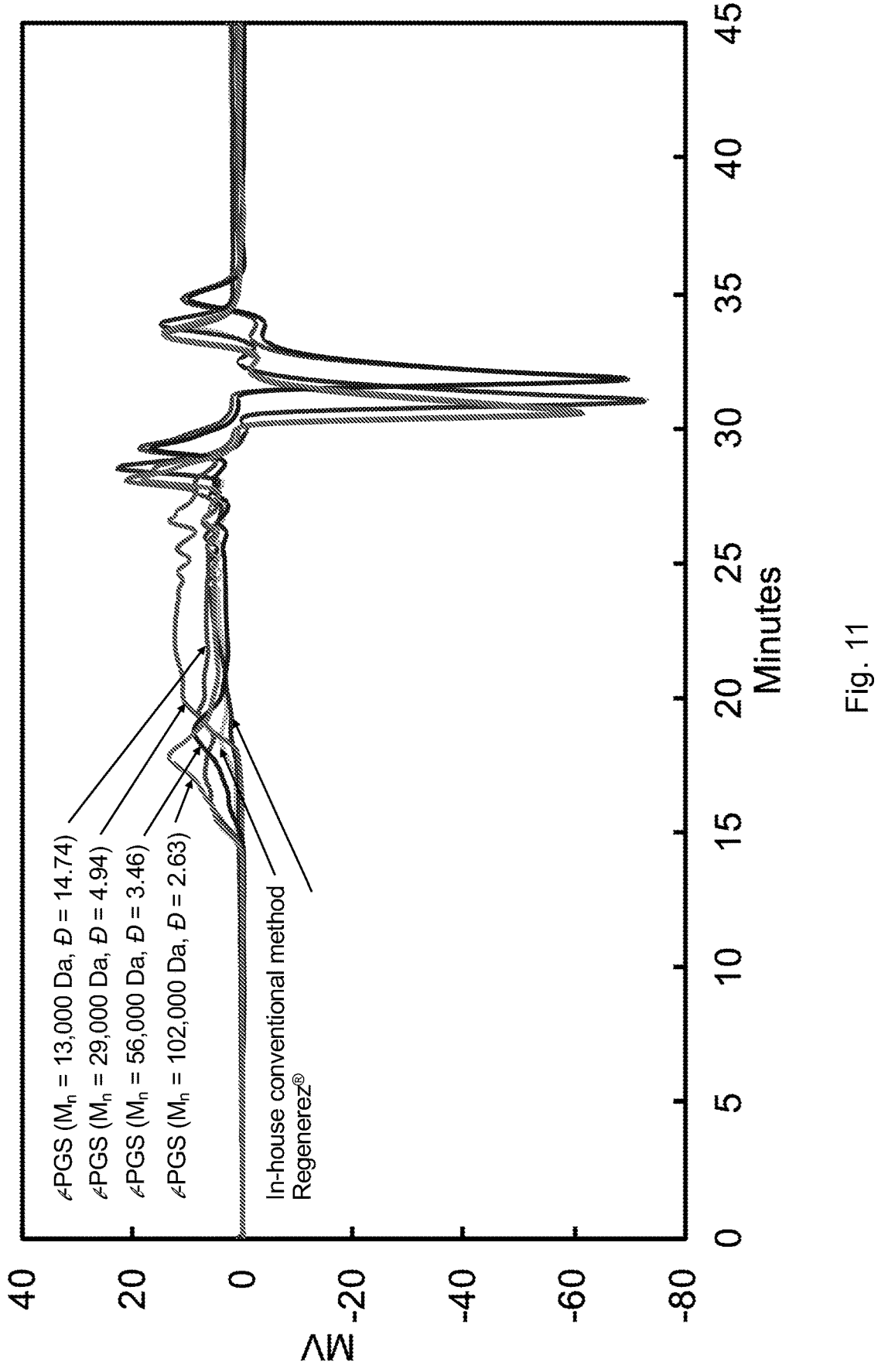
FIG. 11 illustrates a comparison of molecular weights of high MW $\ell$ PGS and controls using GPC.
Figure 12:
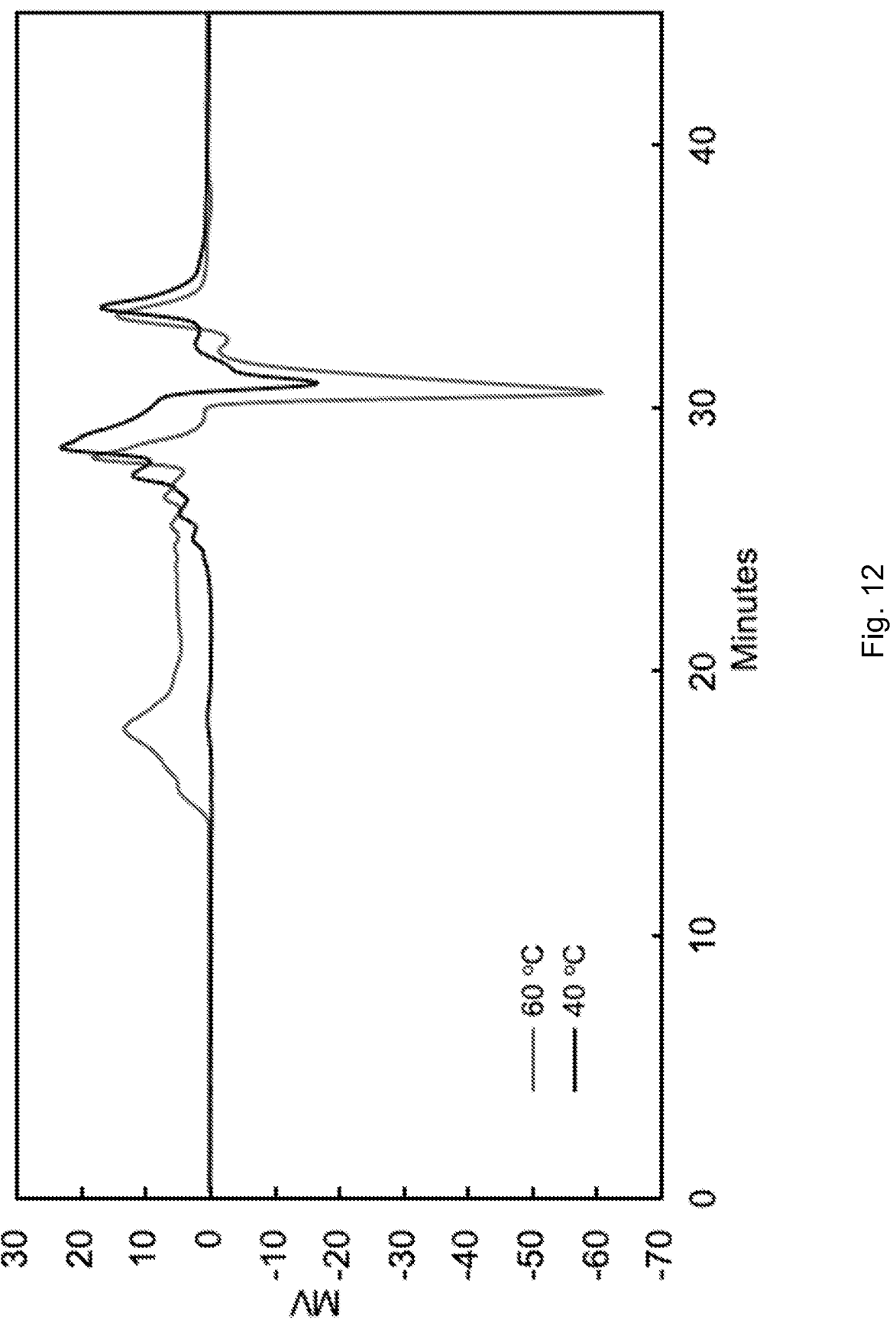
FIG. 12 illustrates a comparison of the molecular weights of PGS synthesized at 40 and 60° C. using GPC. Samples of PGS were synthesized in SC-CO$_2$ at 35 MPa and 18 h with 10 wt. % CALB.
Figure 13:
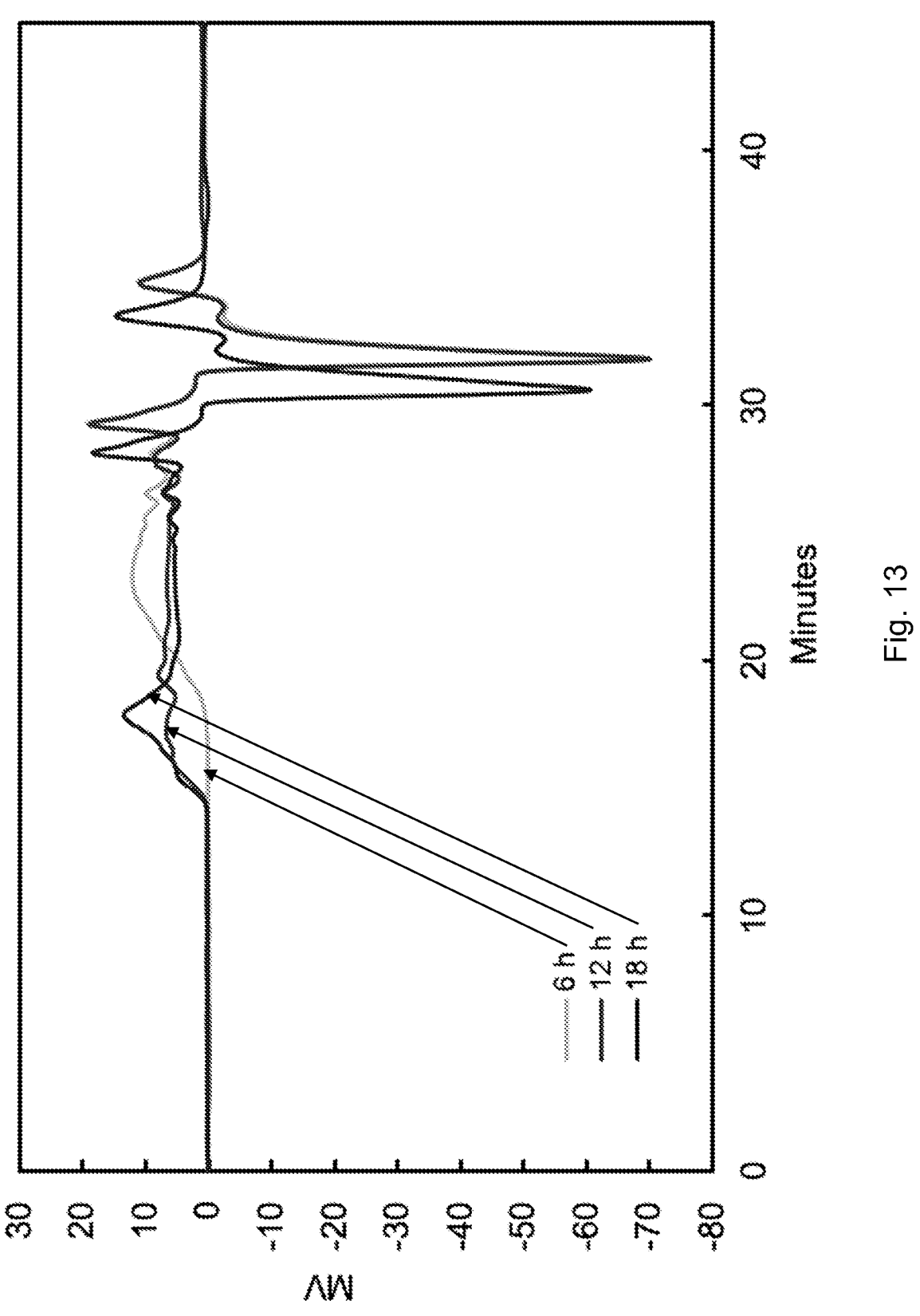
FIG. 13 illustrates a comparison of molecular weights of $\ell$ PGS synthesized at different reaction times using GPC. Samples of $\ell$ PGS were synthesized in SC-CO$_2$ at 35 MPa and 60° C. with 10 wt. % CALB.
Figure 14:
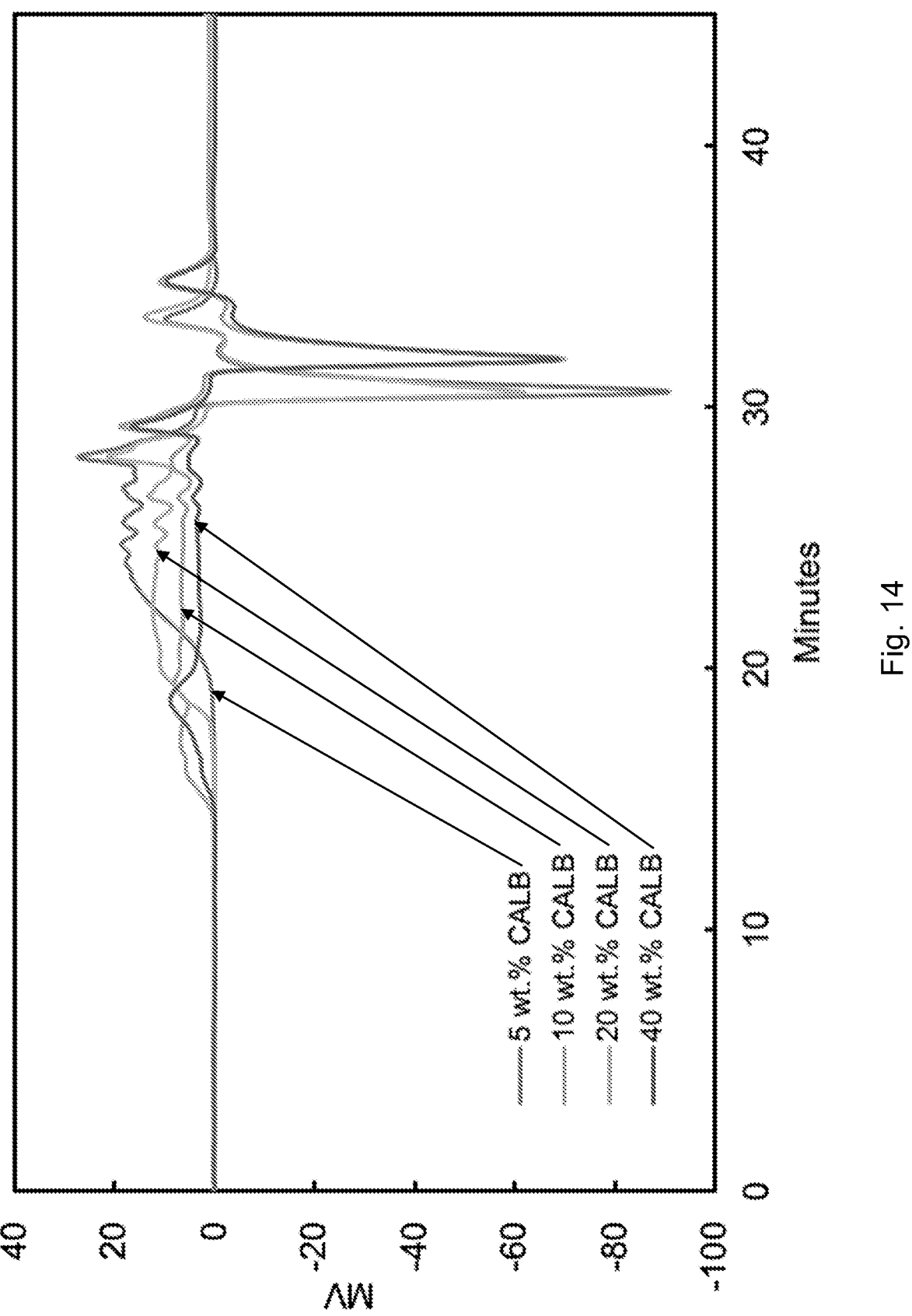
FIG. 14 illustrates a comparison of the molecular weights of PGS synthesized with different lipase contents using GPC. Samples of $\ell$ PGS were synthesized in SC-CO$_2$ at 35 MPa and 60° C. for 12 h.
Figure 15:
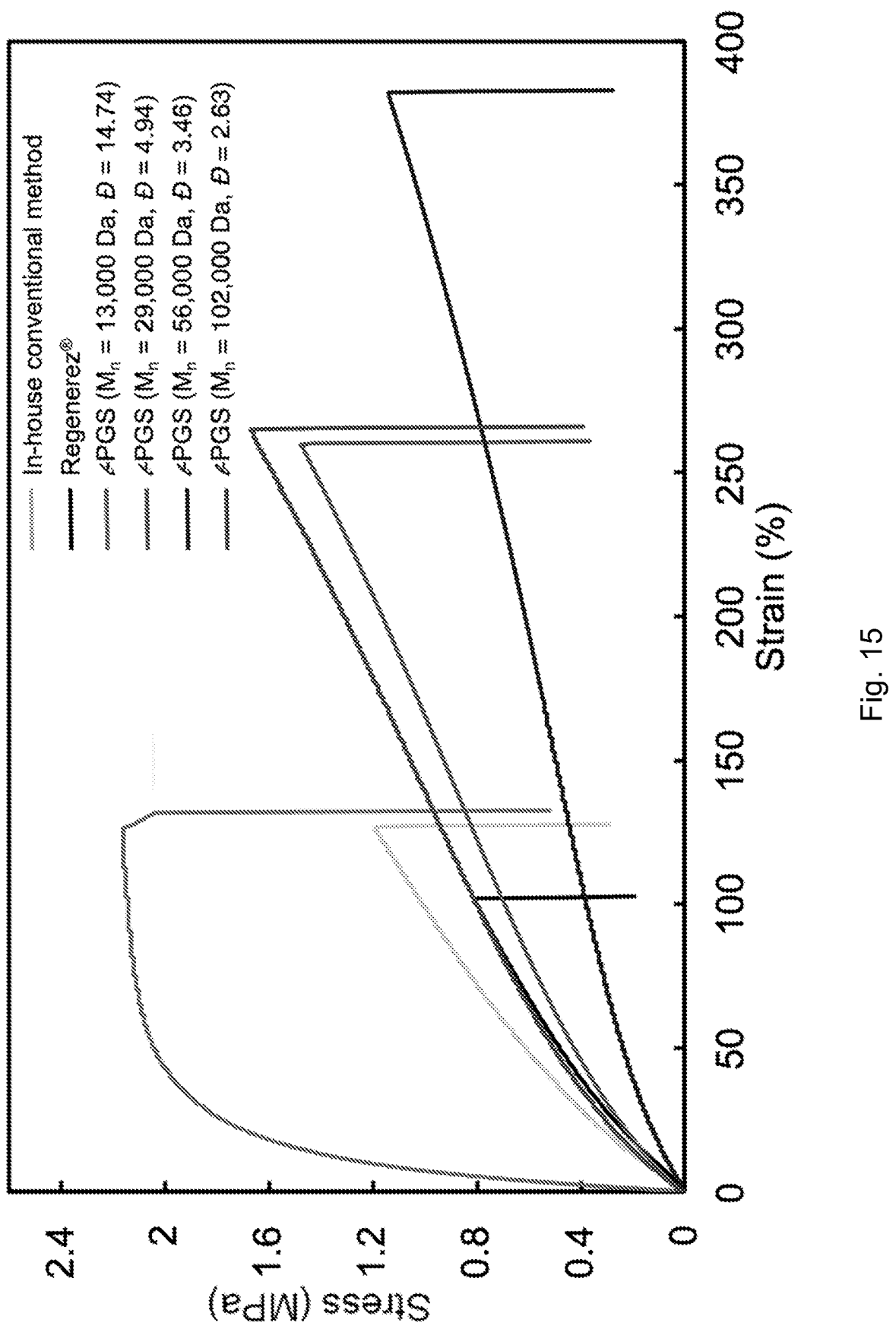
FIG. 15 illustrates examples of original stress-strain curves from tensile tests of PGS controls and $\ell$ PGS generated with different synthesis conditions. Each sample was replicated four times for tensile tests and one representative stress-strain curve for each sample is shown here.

Cytocompatibility. PGS has been widely used in biomedical engineering. Therefore, it is essential for ℓPGS to maintain the excellent cytocompatibility of conventional ones. Human umbilical vein endothelial cells (HUVECs) provide an optimal model system for the study of regulating endothelial cells and their different responses to physical, biochemical and environmental stimuli. The cytocompatibility was evaluated by directly seeding and proliferating HUVECs on a ℓPGS-coated glass. Cultures of HUVECs were tracked for 4 days of observation using live/dead and MTT assays. The microscopic images of live/dead assay on Day 4 showed similar cytocompatibility of ℓPGS and the controls: Regenerez® and tissue culture polystyrene (TCPS) (FIGS. 9A-9C). MTT assay demonstrated that HUVEC metabolic activity on ℓPGS was as good as those on the controls, indicating good cytocompatibility (FIG. 9D and Table 9).

TABLE 9

Experimental data of the MTT assay on
HUVECs for the cytocompatibility study
of the controls and ℓPGS.

| | | Fluorescence absorbance (590 nm) | |
|---|---|---|---|
| | Regenerez ® | Tissue culture polystyrene | ℓPGS ($M_n$: 102,000 Da, Đ = 2.63) |
| Day 1 | 0.76 | 0.99 | 1.06 |
| | 0.68 | 0.70 | 0.82 |
| | 0.84 | 0.86 | 0.58 |
| | 1.00 | 0.65 | 0.71 |
| Mean | 0.82 | 0.80 | 0.79 |
| SD | 0.14 | 0.16 | 0.21 |

| | | Fluorescence absorbance (590 nm) | |
|---|---|---|---|
| | Regenerez ® | tissue culture polystyrene | ℓPGS ($M_n$: 102,000 Da, Đ = 2.63) |
| Day 2 | 0.81 | 1.18 | 1.22 |
| | 0.94 | 1.08 | 0.62 |
| | 0.62 | 1.15 | 0.77 |
| | 1.32 | 1.14 | 1.17 |
| Mean | 0.92 | 1.14 | 0.94 |
| SD | 0.30 | 0.04 | 0.29 |

| | | Fluorescence absorbance (590 nm) | |
|---|---|---|---|
| | Regenerez ® | tissue culture polystyrene | ℓPGS (Mn: 102,000 Da, Đ = 2.63) |
| Day 4 | 1.68 | 0.98 | 1.93 |
| | 1.14 | 0.95 | 0.88 |

TABLE 9-continued

Experimental data of the MTT assay on
HUVECs for the cytocompatibility study
of the controls and ℓPGS.

| | | | |
|---|---|---|---|
| | 0.74 | 1.24 | 0.82 |
| | 1.71 | 1.36 | 1.16 |
| Mean | 1.32 | 1.13 | 1.20 |
| SD | 0.46 | 0.20 | 0.51 |

*n = 4

This reaction design employs SC-$CO_2$ and an immobilized enzyme to synthesize linear high MW polyesters directly from a trifunctional alcohol and a difunctional acid. The larger size and defined structure of synthesized polyesters are very difficult to produce by conventional polycondensation. Existing methods of obtaining large condensation polymers rely on sophisticated catalysts and specialized monomers under extreme synthesis conditions. The reported design is simpler and minimizes environmental impact. It is expected to enable new polyester structures from other natural polyols and diacids, bringing previously inaccessible functions and possibilities.

Methods. Materials. Sebacic acid (98% purity) and glycerol (99.5% minimum purity) were purchased from Alfa Aesar (Ward Hill, MA, USA). Before the polycondensation, sebacic acid was purified by recrystallization from 95% ethanol three times and dried under vacuum as previously described. *Candida antarctica* lipase B (CALB, Novozym® 435, immobilized on acrylic resin, 10,000 PLU/g) was purchased from Strem Chemicals (Newburyport, MA, USA). Commercial poly(glycerol sebacate) (Regenerez®) was purchased from the Secant Group (Quakertown, PA, USA). Carbon dioxide (99.9999% minimum purity) was purchased from Airgas (Radnor, PA, USA).

The supercritical fluid (SCF) system for polymerization. The SCF polymerization system (FIG. 1B) consisted of a high pressure pump (HPP, L100-VES-NBR air driven head pump with 1:113 pressure ratio, Maxpro Technologies, Fairview, PA, USA), SC-$CO_2$ reservoir (316 SS, 1 liter, Maxpro Technologies, Fairview, PA, USA), and reaction vessel (304SS, 50 ml, custom built at Cornell Laboratory of Atomic and Solid State Physics, Ithaca, NY, USA). The SC-$CO_2$ reservoir was equipped with a forward pressure regulator (FPR, Tescom 26-1000 series, Northeast Engineering, Bourne, MA, USA) and connected to the reaction vessel, in order to maintain constant pressure during SC-$CO_2$ venting for water removal while polycondensation proceeds. A metering vale (MV, SS-4-VH, Swagelok, Solon, OH, USA) was installed with a ball valve (BV, SS-1R-S4, Swagelok, Solon, OH, USA) on the outlet of the vessel to maintain constant $CO_2$ flow rate during polycondensation and depressurization steps. Temperatures of the SC-$CO_2$ reservoir, reaction vessel, and MV were respectively controlled with the PID controllers and J-type thermocouples (Omega Engineering Inc., Norwalk, CT, USA).

Synthesis of poly(glycerol sebacate) (PGS) using SC-$CO_2$-mediated polycondensation. Equimolar amounts of glycerol, sebacic acid with 5 to 40 wt. % CALB were premixed thoroughly and loaded in the 50-ml reaction vessel, followed by pressurization to the pressure ranging from 25 MPa to 35 MPa. During pressurization, $CO_2$ filled in the reservoir was pressurized and heated to supercritical state at desired temperature and pressure. Then, SC-$CO_2$ was controllably introduced into the reaction vessel until the operating condition was reached. Operating temperature of the vessel was maintained between 40 and 60° C. in a water bath with variation of 1° C. The pressure was controlled by HPP and FPR with minimal variation of 0.3 MPa. Stirring at 60 rpm was applied during oligomerization of glycerol and sebacic acid for 2 h and continued in polycondensation with SC-$CO_2$ venting, as a driven force for water removal. After the reaction time of 6 to 18 h, SC-$CO_2$ was released from the reaction vessel at a depressurization rate of 0.1 MPa min$^{-1}$. The synthesized ⨍ PGS with CALB beads was directly collected after depressurization. Dissolved in adequate amount of THF, ⨍ PGS was separated from CALB beads by simple filtration, followed by vacuum evaporation to remove the residual solvent.

In-house conventional method. PGS was produced using melt polycondensation as the control of in-house conventional method. Briefly, PGS was synthesized by equimolar amounts of glycerol and sebacic acid at 120° C. under nitrogen for 24 h. Then, the pressure was reduced from ~0.1 MPa (ambient pressure) to 4 Pa (>99.999% vacuum) over 5 h. The reaction mixture was kept at 4 Pa and 120° C. for 48 h to obtain the resultant polymers.

Polymer characterization and cytocompatibility. The methods applied in this study were detailed in the supplementary information for the physical, thermal, and mechanical properties of the synthesized ⨍ PGS. The live/dead and MTT assays were performed to evaluate the cytocompatibility of ⨍ PGS.

Gel permeation chromatography (GPC). The control and synthesized ⨍ PGS dissolved in THF at a concentration of 3 mg ml$^{-1}$ were prepared at ambient temperature and agitated on the orbit shaker at 140 rpm overnight. The molecular weight was determined using a Waters Breeze GPC system (Waters Corp., Milford, MA, USA) equipped with a Waters 1515 Isocratic HPLC pump, Waters 410 differential refractive index detector, and PSS SDV® gel columns (8 mm ID×300 mm Length with average pore size of 5 μm, Polymer Standards Services, Amherst, MA, USA). (FIGS. 2, 10A-10C, and 11-14). The elution time was set at 45 min using THF as the eluent at a flow rate of 1 ml min$^{-1}$ and 40° C. Polystyrene standards with MW ranging from 1,000 Da to 1,000,000 Da were applied to generate the calibration curve.

Nuclear magnetic resonance (NMR) spectroscopy. Chemical structure and composition of the control and ⨍ PGS were analyzed with a Varian INOVA 400 MHz spectrometer (Varian Inc., Palo Alto, CA, USA). (FIGS. 4A-4B, and 5A-5B). Acetone-$d_6$ was used as the solvent for proton NMR spectroscopy. $^1$H spectra were determined with four scans at 30 s relaxation delay and 90-degree excitation pulse. The solvent residual peak appeared at 2.08 ppm in $^1$H NMR spectra. Comparing the integral ($H_{b'}$) of the methine peaks on the glycerol moiety between 4.8 and 5.5 ppm to the integral ($H_c$) of the methylene peak on the sebacoyl moiety at 2.35 ppm, the degree of branching (DB) for PGS was calculated using Equation (1), and the results were presented in FIGS. 4A-4B.

$$DB=4 \times (\text{integral area } H_{b'}/\text{integral area } H_c) \qquad (1)$$

Where $H_{b'}$ indicates the integral area of esterification on the secondary hydroxyl group (b') of glycerol. $H_e$ is the integral area of methylene groups (c) adjacent to a carboxylic acid ester (O=C—O) and normalized as 1.

Figure 6A:
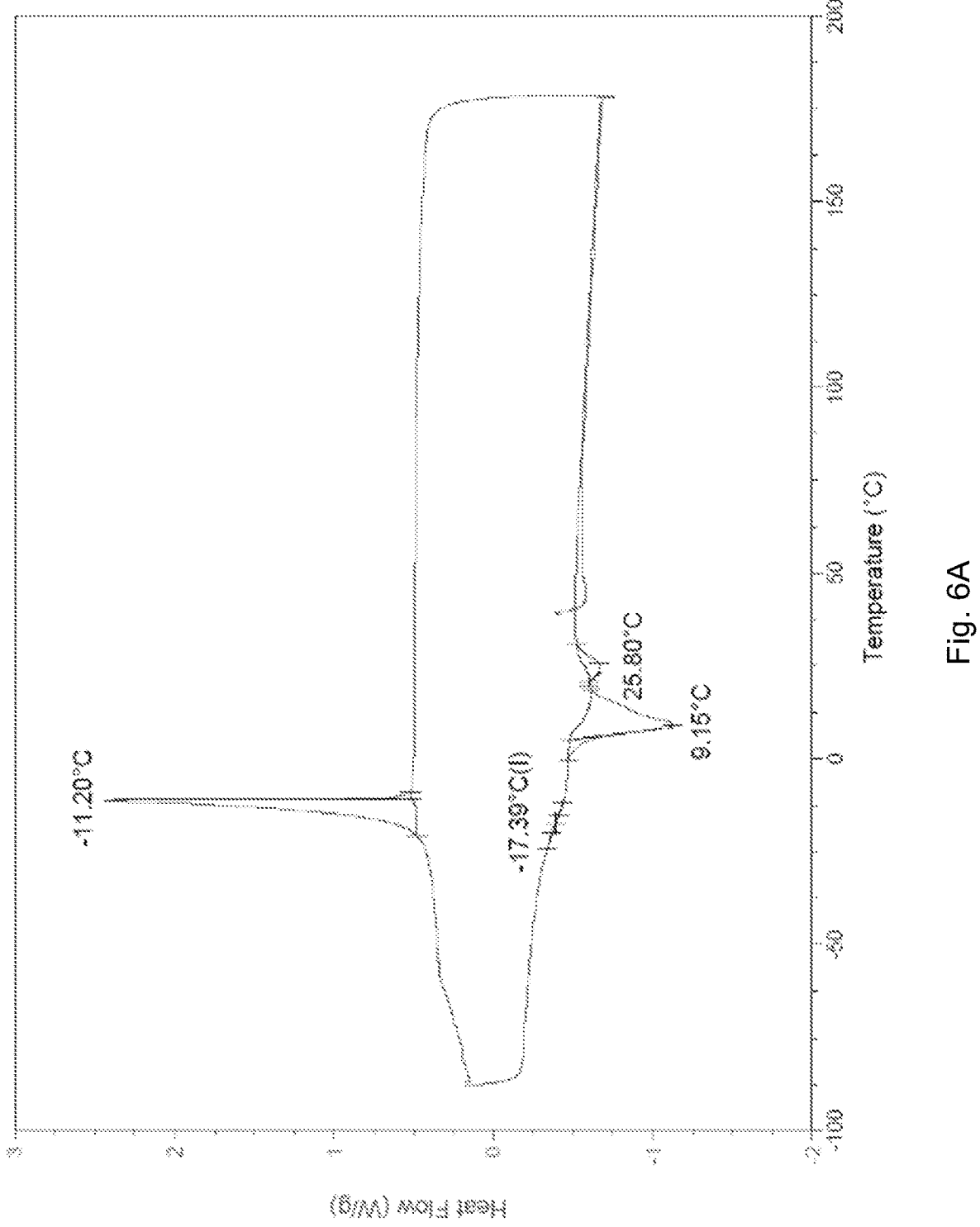
FIGS. 6A-6B illustrate differential scanning calorimetry (DSC) analyses for (6A) Regenerez® as a control and (6B) a $\ell$ PGS (M$_n$=102,000 Da and Đ=2.63). The $\ell$ PGS was synthesized using lipase-catalyzed polycondensation in SC-CO$_2$ at 35 MPa and 60° C. for 18 h with 10 wt. % CALB.
Figure 6B:
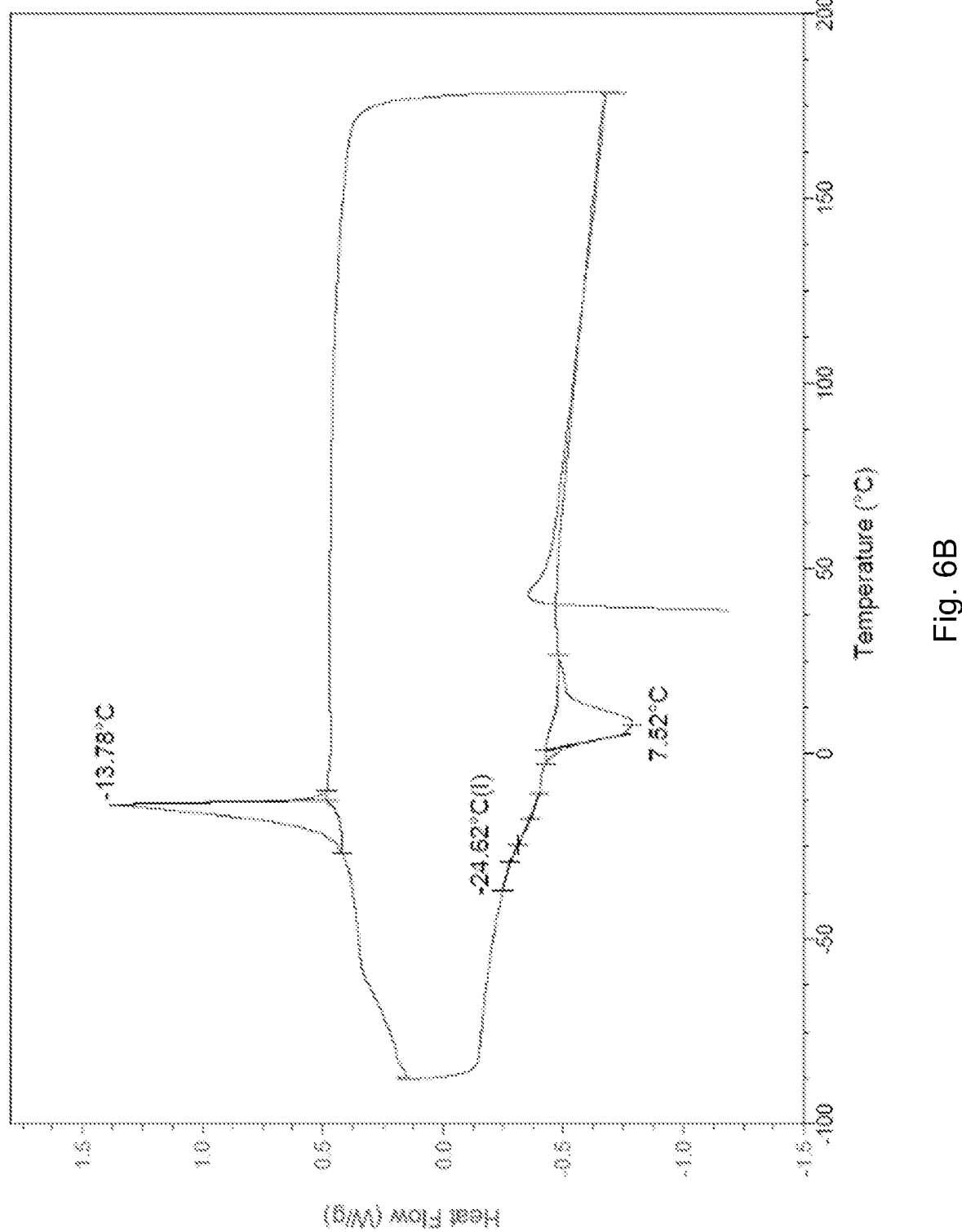

Differential scanning calorimetry (DSC). Thermal properties of the control and ⨍ PGS were determined using Q1000 Modulated Differential Scanning Calorimeter (TA Instruments, New Castle, DE, USA) equipped with a three-stage refrigerated cooling system for optimum temperature control and stability. (FIGS. 6A-6B). The sample (10 mg) was loaded and sealed in a Tzero® Hermetic aluminum pan (TA Instruments, New Castle, DE, USA) and put in the DSC cell, followed by the heating/cooling/heating cycle under a dry nitrogen atmosphere at a heating/cooling rate of 10° C. min$^{-1}$ from −90 to 180° C. The phase transitions were analyzed using TA Universal Analysis 2000.

Fourier transform infrared (FTIR) spectroscopy. The FTIR spectra were recorded using on a Bruker Vertex V80V Vacuum FTIR system (Bruker Corp., Billerica, MA, USA) with a deuterated triglycine sulfate (DTGS) detector. (FIG. 4C) The PGS sample (10 mg) was scanned from 400 to 4,000 cm$^{-1}$ for 16 times at ambient temperature. Transmittance data were plotted as a function of wavenumbers.

Characterization of mechanical properties. The controls and ⨍ PGS were respectively dissolved in THF at the concentration of 20 wt. % with orbital shaking at 140 rpm overnight to assure complete dissolution. The solution was poured into a casting mold made of a silicone sheet on a glass slide (length×width×thickness; 50 mm×20 mm×0.8 mm). The PGS solutions were air dried in a fume hood under the ambient condition overnight, followed by vacuum drying at 60° C. for 24 h to completely remove the residual solvent and bubbles formed within the viscous films. Then, the samples were cured at 150° C. under 4 Pa (>99.999% vacuum) for 20 h to yield crosslinked PGS elastomers.

Tensile testing was conducted using an Instron Universal Testing system (Instron Corp., Norwood, MA, USA) equipped with a 50 N load cell, following the ASTM D412 standard for elastomers. Dog bone-shaped samples of crosslinked PGS elastomers were made using the ASTM D412 dog-bone cutting die (length×width×thickness; 14.75 mm×3 mm×1.3 mm). The tensile properties of PGS elastomers were evaluated with a strain rate of 125 mm min$^{-1}$. (FIGS. 8B-8D, and 15). For cyclic tensile tests, the PGS elastomers were pulled to the strains of 30% and 70% respectively, and then allowed to recover to 1% strain before immediately stretched for 500 cycles. (FIGS. 7-8A).

In vitro cytocompatibility study. Cytotoxicity assays were performed on the PGS coating using human umbilical vein endothelial cells (HUVECs, No. CC-2517, Lonza, Morristown, NJ, USA). HUVECs were cultured in an endothelial cell growth medium (EGM™-2 MV Microvascular Endothelial Cell Growth Medium, Lonza, Morristown, NJ, USA) at 37° C. with 5% $CO_2$ until sufficient quantities were obtained. The HUVECs were diluted to 5×10$^4$ cells mL$^{-1}$ in the cell growth media for the assays. PGS in THF was prepared at a concentration of 1% w/v, and 20 μL of each solution was evenly spread on a 15-mm round cover glass. Dried in a fume hood overnight and further crosslinked in a vacuum oven at 150° C. under 4 Pa (>99.999% vacuum) for 20 h, a PGS coating with a thickness of ~1,000 nm was formed on the cover glass. The coated cover glasses were placed into a 24-well tissue culture polystyrene (TCPS) plate with the coating layers orientated upward.

The coatings on cover glasses in the culture plate were subsequently washed with 75, 50, and 25% w/v ethanol solutions and Dulbecco's phosphate-buffered saline, respectively. Then, HUVECs were seeded on the PGS coating for $5\times10^4$ cells per well. The plates were incubated at 37° C. with 5% $CO_2$. After incubation for 24, 48, and 96 h, cell viability (the MTT assay, n=4) was determined using a CellTiter-Blue® Cell Viability Assay kit (Promega, Madison, WI, USA). (FIG. 9D). The live/dead assay (n=4) was performed using a LIVE/DEAD Viability/Cytotoxicity kit (Invitrogen, Carlsbad, CA, USA). The polyanionic calcein was well retained within live cells, generating an intense green fluorescence (excitation/emission ~495 nm/~515 nm). Ethidium homodimer-1 (EthD-1) diffused into the cells with damaged membranes and bound to cellular nucleic acids, thereby producing a bright red fluorescence in dead cells (excitation/emission ~495 nm/~635 nm). The fluorescence microscopy images of the live/dead assay were recorded using a Nikon Eclipse Ti2-E fluorescence microscope (Nikon Instruments Inc., Melville, NY, USA). (FIGS. 9A-9C). The HUVECs cultured on the TCPS plate and commercial PGS coating (Regenerez®) were chosen as the controls.

Statistical analysis: Mechanical properties and cytocompatibility of the controls and ℓ PGS were evaluated using separate samples for each synthesis at least in triplicate and presented as mean±standard deviation (SD). Data were analyzed using JMP® Pro 14 (SAS Institute Inc., Cary, NC, USA). To compare mechanical properties among the PGS elastomers, analysis of variance (ANOVA) was performed for significant differences among means, with Tukey's pairwise comparison tests at a significance level of p<0.05. Data of the MTT assay were analyzed employing the linear mixed model, because the cell growth on each coating of PGS produced with different synthesis conditions were repeatedly measured over 24, 48, and 96 h, respectively. The samples were entered in the model as a random effect. Incubation periods, types of the crosslinked PGS elastomers, and their interaction were entered in the model as the fixed effects. A significance level of p<0.05 was selected for this data analysis.

Example 2

The following is an example of a method and polymer of the present disclosure.

In an example, poly(glycerol sebacate) (PGS) was chosen as a representative model. In an example, equimolar amounts of glycerol, sebacic acid with 5 to 40 wt. % CALB were premixed thoroughly and loaded in the 50-ml reactor, followed by pressurization to the desired pressure ranging from 25 MPa to 35 MPa. Operating temperature of the reactor was maintained in a water bath between 40 and 60° C. with variation of 1° C. During SC-$CO_2$ pressurization, the reservoir filled with $CO_2$ was pressurized and heated to supercritical status at desired temperature and pressure. Then, SC-$CO_2$ was controllably introduced into the reactor until the operating condition was reached. Stirring at 60 rpm was maintained during oligomerization of glycerol and sebacic acid for 2 hours, followed by SC-$CO_2$ venting as a driven force for water removal during polycondensation. The pressure was maintained by high pressure pump (HPP) and forward pressure regulator (FPR) with minimal variation of 0.3 MPa. After processing time of 6 to 18 h, SC-$CO_2$ was released from the reactor at a depressurization rate of 0.1 MPa/min. The synthesized PGS with CALB beads was directly collected after depressurization. Simple filtration was applied to separate the CALB beads and the polymer PGS dissolved in adequate amount of THF, followed by vacuum evaporation for complete solvent removal. In an aspect, the present disclosure provides polymers.

Example 3

The following is an example of methods and polymers of the present disclosure.

In this example, system conditions were evaluated. The molecular weight ($M_w$)>100,000 Dalton and polydispersity index (PDI, Đ)<5 of the synthesized PGS were reached at 35 MPa and 60° C. with processing time of 12 to 18 h and CALB content of 10 to 40 wt. %, as presented in Table 10.

TABLE 10

| Operating conditions, molecular weight distributions of the polymer PGS synthesized using SC—$CO_2$ polycondensation. | | | | | | | |
|---|---|---|---|---|---|---|---|
| No. | Pressure (MPa) | Temp (° C.) | time(h) | CALB (%) | $M_w$ (Dalton) | $M_n$ (Dalton) | Đ |
| 1 | 35 | 60 | 6 | 10 | 5,600 | 3,500 | 1.59 |
| 2 | 35 | 60 | 12 | 10 | 185,000 | 13,000 | 14.74 |
| 3 | 35 | 60 | 18 | 10 | 269,000 | 102,000 | 2.63 |
| 4 | 35 | 60 | 6 | 20 | 5,000 | 3,200 | 1.55 |
| 5 | 35 | 60 | 12 | 20 | 145,000 | 29,000 | 4.94 |
| 6 | 35 | 60 | 18 | 20 | 22,000 | 9,200 | 2.34 |
| 7 | 35 | 60 | 12 | 40 | 195,000 | 56,000 | 3.46 |
| 8 | 35 | 60 | 12 | 5 | 3,000 | 2,400 | 1.24 |
| 9 | 35 | 60 | 6 | 10 | 6,000 | 3,400 | 1.82 |
| 10 | 35 | 50 | 6 | 10 | 1,600 | 1,600 | 1.06 |
| 11 | 35 | 40 | 4 | 8 | 1,200 | 1,200 | 1.00 |
| 12 | 35 | 40 | 8 | 8 | 3,300 | 2,500 | 1.31 |
| 13 | 35 | 40 | 18 | 8 | 6,600 | 3,000 | 2.16 |
| 14 | 35 | 40 | 24 | 8 | 12,000 | 3,100 | 3.89 |
| 15 | 25 | 60 | 6 | 10 | 1,700 | 1,500 | 1.12 |
| 16 | 25 | 60 | 12 | 20 | 80,000 | 10,000 | 7.88 |

Example 4

The following is an example of methods and polymers of the present disclosure.

Variables for controlling physicochemical and mechanical properties of synthesized poly(glycerol sebacate) (PGS) were evaluated. The polymers produced using this SC-CO2 polycondensation is effectively linear, thus referred to as ℓ PGS. Molecular weights and polydispersity index (PDI) of synthesized 1-PGS can be controlled with operating temperature, enzyme content (lipase), operating pressure, and reaction time.

Molecular weight and PDI of ℓ PGS can also be controlled by operating pressure. SC-$CO_2$ with higher pressure enhances its density, resulting in improved plasticization and diffusivity in polymer matrix to facilitate lipase-catalyzed polycondensation. As shown in Table 4, increasing pressure from 25 to 35 MPa improves MW of ℓ PGS. With extending reaction time from 6 to 12 h and increasing lipase content to 20 wt. %, the increase in MW of ℓ PGS was pronounced while PDI was maintained.

Molecular weight and PDI of PGS can be controlled by varying enzyme content for polycondensation in SC-$CO_2$. In Table 5, raising lipase content from 5 to 40 wt. % improves MW of ℓ PGS and reduces PDI. PDI is defined as $M_w/M_n$. Therefore, ℓ PGS produced using 10 wt. % CALB exhibits relatively high MW with high PDI of 14.74. Ascending order of $M_n$ was correspondent to rising CALB content.

Molecular weight and PDI of PGS can be controlled by varying reaction time. As shown in Table 6, MW of l-PGS is improved with reaction time increasing from 6 to 18 h. PDI of ⨍PGS is significantly reduced when the reaction time was extended from 12 to 18 h, consistent with the increase in number average molar mass ($M_n$). PDI increases from 1.59 to 14.74 while the reaction time increases from 6 to 12 h, when high MW PGS begins to form amid smaller MW oligo-esters. Extending to 18 h, PDI reduces to 2.63 while the majority of ⨍PGS possesses high MW.

Summarized in Table 11, ⨍PGS with high molecular weight and controlled PDI can be achieved with polycondensation in SC-$CO_2$. The optimized operating condition is found to be 35 MPa and 60° C. for 12 to 18 h, with the lipase content ≥ 10 wt. %. High MW, uniformity (reduced PDI), and linearity would make a profound effect on controlling mechanical properties of crosslinked PGS elastomers.

TABLE 11

Molecular weight distribution and PDI of ⨍PGS synthesized in SC—$CO_2$ polycondensation with optimized operating conditions.

| Synthesis of l-PGS | $M_w$ (Dalton, Da) | $M_n$ (Dalton, Da) | PDI |
|---|---|---|---|
| Regenerez ® | 7,200 | 2,700 | 2.63 |
| In-house conventional method[a] | 22,000 | 4,100 | 5.31 |
| l-PGS with 10 wt. % CALB[b] | 185,000 | 13,000 | 14.74 |
| l-PGS with 20 wt. % CALB[b] | 145,000 | 29,000 | 4.94 |
| l-PGS with 40 wt. % CALB[b] | 195,000 | 56,000 | 3.46 |
| l-PGS with 10 wt. % CALB for 18 h[c] | 269,000 | 102,000 | 2.63 |

[a]Melt polycondensation at 120° C. for 72 h under absolute vacuum
[b]35 MPa, 60° C. and the reaction time of 12 h in SC—$CO_2$
[c]35 MPa, 60° C. and the reaction time of 18 h in SC—$CO_2$ A commercial PGS (Regenerez®; Secant Group, Quakertown, PA, USA) and a PGS from in-house conventional method (melt polycondensation at 120° C. for 72 h under absolute vacuum) arechosen to compared mechanical properties with ⨍PGS made by SC-$CO_2$ polycondensation. The molecular weight and PDI of the selected PSG are presented in Table 11. ⨍PGS and conventional PGS controls were cured under identical conditions: 150° C., 30 mTorr, and 20 h. Cyclic tensile tests of the crosslinked ⨍PGS and controls were performed at a 70% strain for 500 cycles under identical tensile elongation. As shown in FIG. 8A, three types of elastomers made of ⨍PGS ($M_n$=29,000 Da, PDI=4.94; $M_1$=56,000 Da, PDI=3.46; $M_n$=102,000 Da, PDI=2.63) can sustain 500 cycles of 70% tensile strain. Samples of the two conventional PGS controls and one ⨍PGS (Mn=13,000 Da, PDI=14.74) snapped within the first 100 cycles when subjected to 70% strain. Therefore, larger and more uniform ⨍PGS produces more resilient elastomers, likely because of the more regular crosslinked network.

Figure 16A:
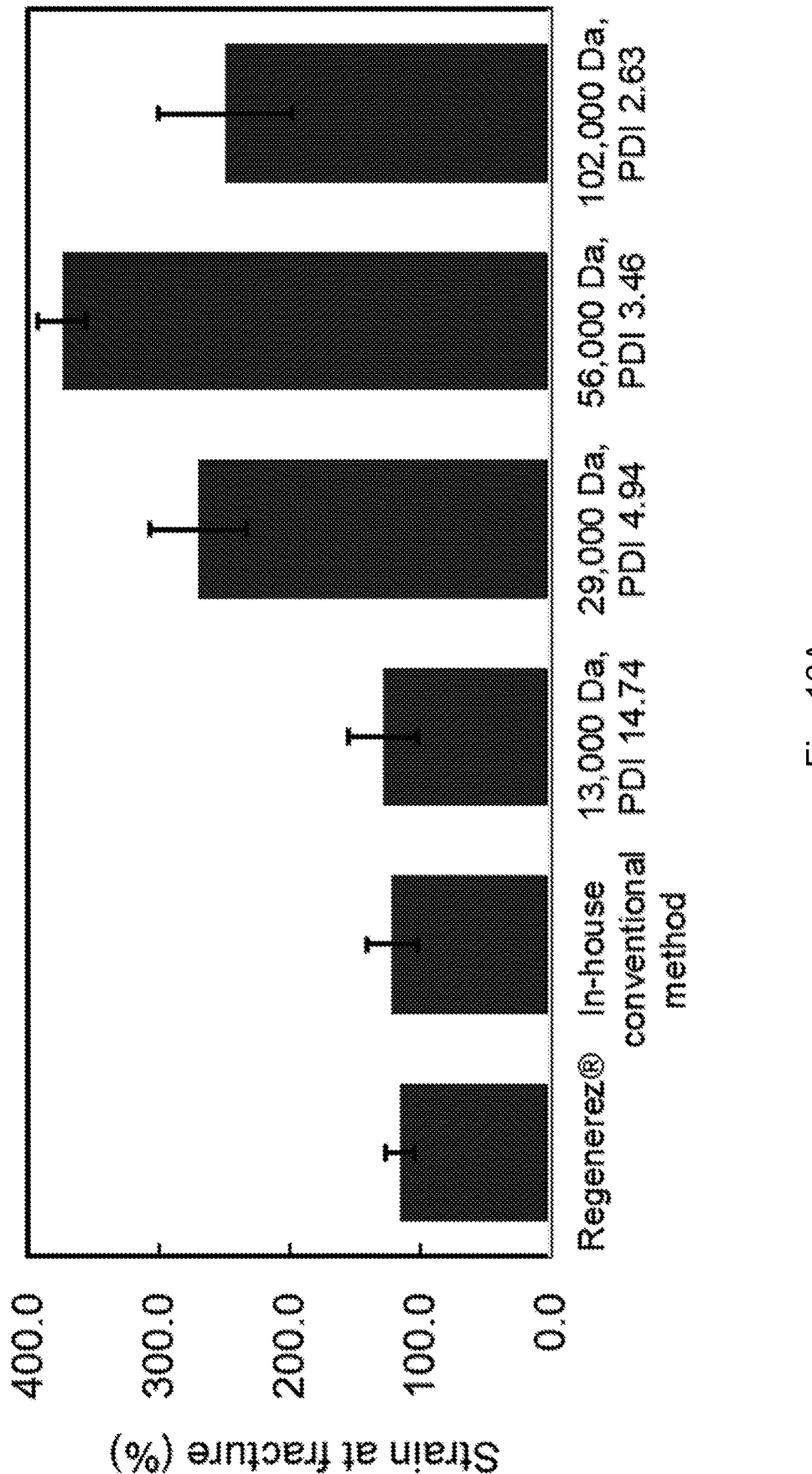
FIGS. 16A-16B illustrate comparisons of mechanical properties of crosslinked PGS elastomers for a SC-CO$_2$ and a conventional melt polycondensation. (16A) Strain at fracture (n=4), (16B) Ultimate tensile stress (UTS, MPa; n=4).
Figure 16B:
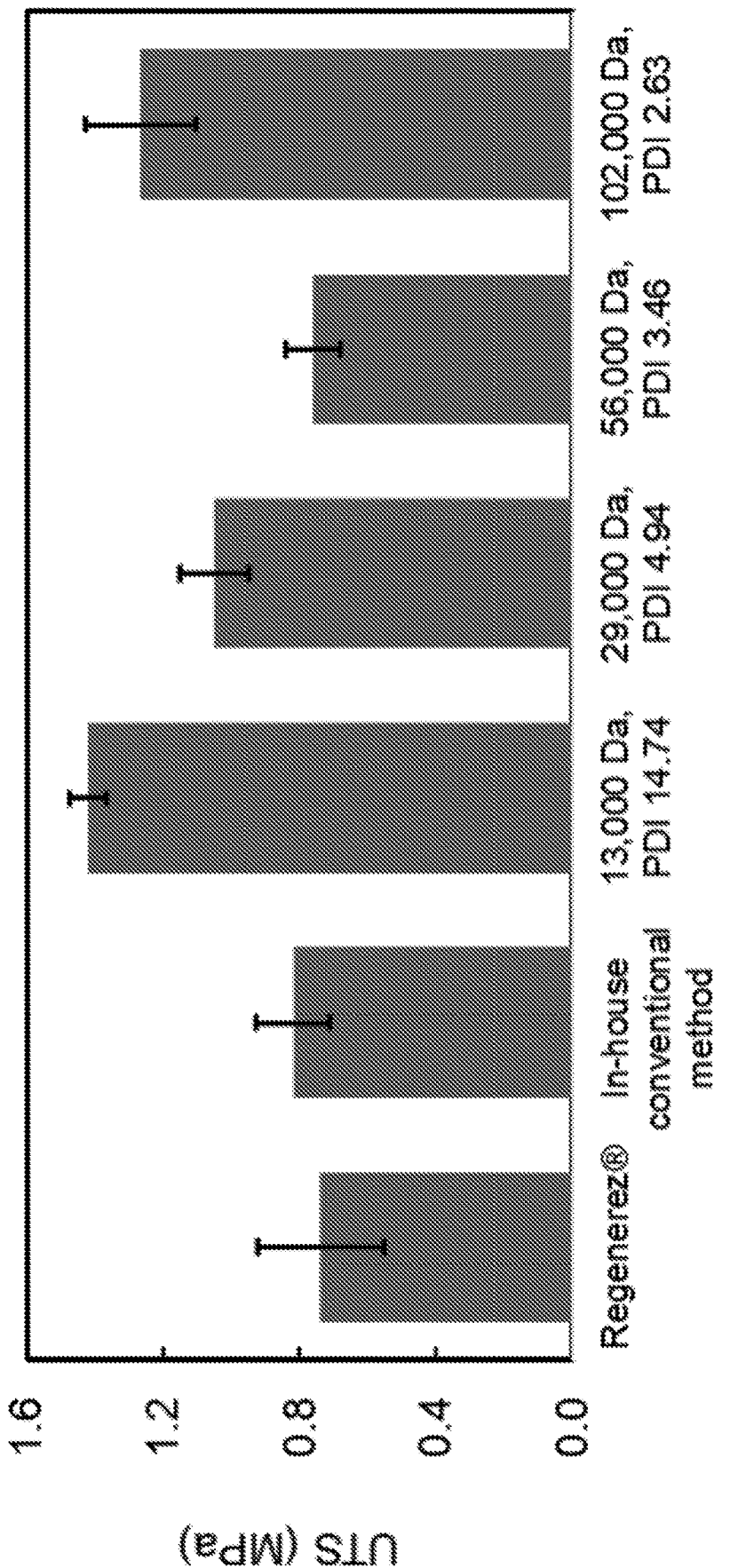

Depending on synthesis parameters, the crosslinked ⨍PGS exhibits 2 to 3 times higher elongation with improved ultimate tensile stress than controls made from conventional PGS, as shown in FIGS. 16A-16B. In FIG. 16A, elongation is improved with Mn of ⨍PGS from 13,000 Da to 56,000 Da while PDI is reduced from 14.74 to 3.46. The results correspond to ⨍PGS synthesized with the lipase content raised from 10 wt. % to 40 wt. % in SC-$CO_2$ at 35 MPa and 60° C. for 12 h; a reverse order of ultimate tensile stress is observed for ⨍PGS made with the lipase content raised from 10 wt. % to 40 wt. % (FIG. 16B). To meet the demand of biomedical applications, a ductile and soft elastomeric biomaterial can be generated and controlled using enzyme-catalyzed polycondensation in SC-$CO_2$ by an integrated condition of operating parameters-pressure, temperature, lipase content, and reaction time. Breakthroughs in high molecular weight, uniformity, and linearity of synthesized biodegradable polyesters can be achieved with this sustainable cost-effective strategy of polycondensation in SC-$CO_2$.

Alternative choices of lipases employed in polymerization. Based on literature research, the lipases listed in Table 1 have been attempted for polymerization or esterification in the solid state (bulk), organic solvents, and supercritical carbon dioxide. More types of lipases and esterases can be evaluated for catalytic specificity and efficiency.

Figure 17:
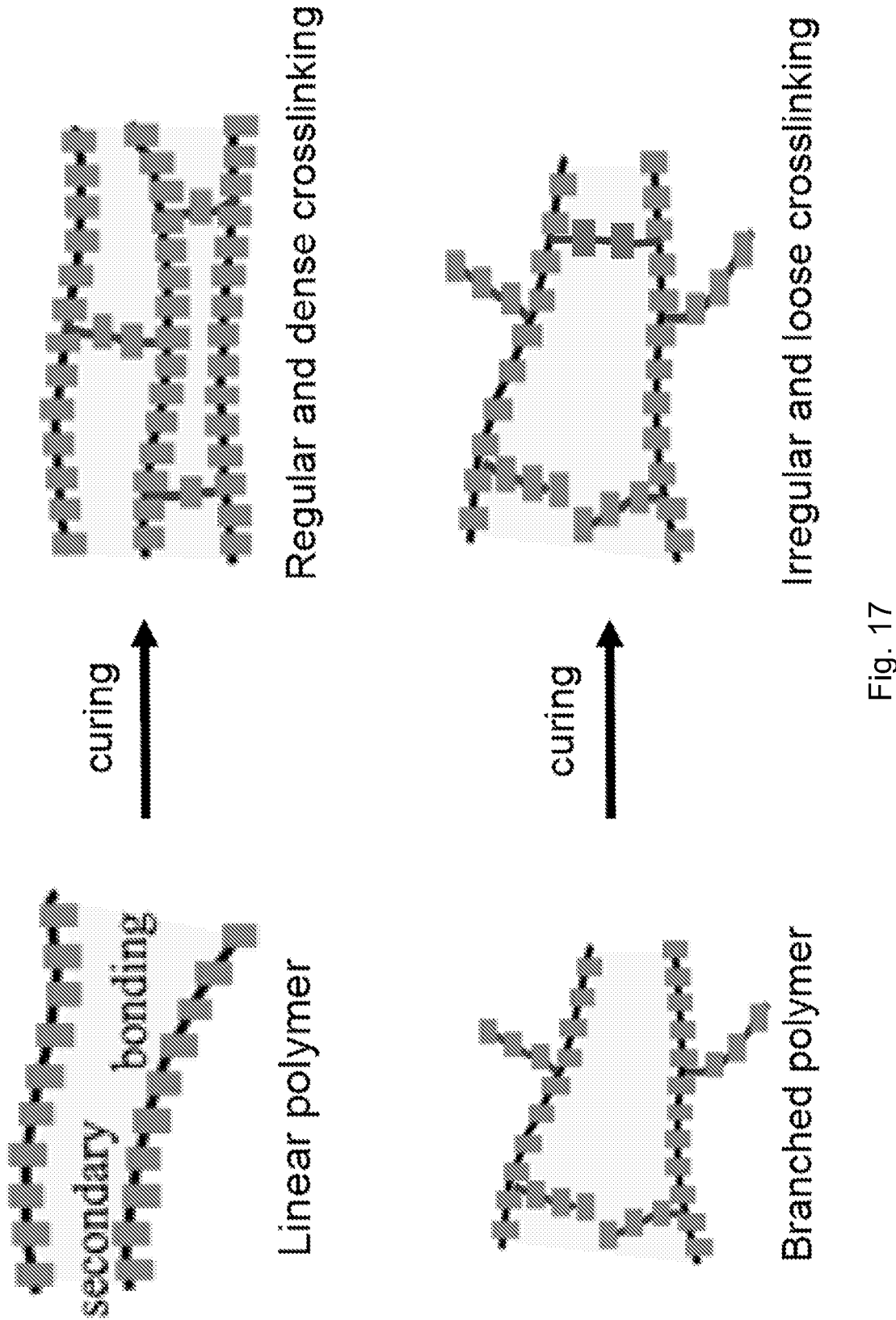
FIG. 17 illustrates crosslinked structures of linear and branched polymers.

FIG. 17 illustrates the crosslinking structure of the elastomers generated with linear and branched PGS. Linear polymer forms regular and dense crosslinked elastomers, imparting improved stretchability and durability. Branched polymers with shorter chains hanging from the backbone can interfere with efficient packing of the polymers. Irregular and loose crosslinked elastomers are generated with fragile and inflexible structure.

SC-$CO_2$ polycondensation is suitable for different monomers. The SC-$CO_2$ polymerization is developed as an innovative platform for polycondensation of simple and readily available monomers consisting of polyols (such as glycerol, butanediol and sorbitol) and diacids (such as sebacic acid, succinic acid, and adipic acid). Naturally sourced polyols and diacids cab be tested using this technique for synthesis of new biomaterials. This process also can be applied for ring-opening polymerization using cyclic monomers, such as lactide, lactone, and caprolactone. This flow-through process of SC-$CO_2$ with biocatalysts can be applied to synthesize the majority of existing biodegradable polymers or create new polymers, with an amenable and efficient strategy as well as environmental protection.

Although the present disclosure has been described with respect to one or more particular examples, it will be understood that other examples of the present disclosure may be made without departing from the scope of the present disclosure.

The invention claimed is:

1. A method of forming a polymer comprising:
   forming a mixture comprising:
      one or more monomer(s),
      wherein the monomer(s) is/are chosen from diacid monomers, polyol monomers, amino alcohol monomers, and combinations thereof;
      one or more biocatalyst(s); and
      supercritical carbon dioxide fluid or subcritical carbon dioxide liquid,
   wherein the mixture does not initially contain water, organic solvent(s), metal catalyst(s), metal(s) thereof, or combinations thereof, and
   continuously venting carbon dioxide out of the mixture,
      wherein continuously venting carbon dioxide out of the mixture maintains a total water content of the mixture at less than 3 wt. %,
   wherein the polymer is formed.

2. The method of claim 1, wherein the monomer(s) are independently present at equimolar amounts based on the total mixture.

3. The method of claim 1, wherein the biocatalyst(s) selectively catalyze(s) a primary hydroxyl group over a secondary hydroxyl group in an esterification reaction with a carboxylic acid group.

4. The method of claim 1, wherein the biocatalyst(s) is/are chosen from enzymes and combinations thereof.

5. The method of claim 4, wherein the biocatalyst(s) is/are chosen from lipases and combinations thereof.

6. The method of claim 5, wherein the biocatalyst(s) is/are chosen from *Candida antarctica* lipase B, *Candida antarctica* Lipase A, *Thermomyces lanuginosus* lipase, *Aspergillus oryzae* Lipase, *Rhizomucor miehei* lipase, Porcine pancreatic lipase, *Pseudomonas cepacia* lipase, *Burkholderia cepacia* lipase, *Aspergillus niger* lipase, *Mucor miehei* lipase, *Pseudomonas fluorescens* lipase, *Burkholderia cepacia* lipase, *Candida rugosa* lipase, and combinations thereof.

7. The method of claim 1, wherein the biocatalyst(s) is/are chosen from homogeneous biocatalyst(s), heterogeneous biocatalyst(s), and combinations thereof.

8. The method of claim 1, wherein the biocatalyst(s) is/are present at 1 to 60 wt. %, based on the weight of the monomer(s).

9. The method of claim 1, wherein the monomer(s) are not initially molten.

10. The method of claim 1, further comprising heating and/or pressurizing a carbon dioxide gas, thus forming the supercritical carbon dioxide fluid or the subcritical carbon dioxide liquid prior to forming the mixture.

11. The method of claim 10, wherein the supercritical carbon dioxide fluid or the subcritical carbon dioxide liquid has a density of 0.47 $g/m^3$ or more.

12. The method of claim 1, wherein the monomer(s) and the biocatalyst(s) are contacted in the mixture prior to continuously venting carbon dioxide out of the mixture.

13. The method of claim 1, further comprising separating the polymer from at least a portion of unreacted monomer(s), if unreacted monomer(s) is/are present, the biocatalyst(s), and/or the supercritical carbon dioxide fluid or the subcritical carbon dioxide liquid in the mixture.

14. The method of claim 1, further comprising crosslinking at least a portion of the polymer.

15. The method of claim 1, wherein the polymer has:
a molecular weight of 20,000 g/mol or more; and/or
a polydispersity index of 5 or less.

16. The method of claim 1, wherein the polymer is a linear polymer comprising 40% or less branching.

17. The method of claim 1, wherein the polymer is formed by a condensation polymerization reaction or a ring-opening polymerization reaction.

18. The method of claim 1, wherein the polymer is substantially free of metal and metal catalyst and/or organic solvent.

19. The method of claim 1, wherein:
a temperature of the mixture is 35 to 70° C.; and/or
a pressure of the mixture is 10 to 40 MPa.

20. The method of claim 19, further comprising heating and/or pressurizing the monomer(s) and biocatalyst(s) to the temperature and/or the pressure of the mixture prior to forming the mixture.

21. The method of claim 1, wherein the polymer is a polyester, a polyamide, or polyester amide.

\* \* \* \* \*